(12) United States Patent
Kock et al.

(10) Patent No.: US 9,051,553 B2
(45) Date of Patent: Jun. 9, 2015

(54) POLY(ADP-RIBOSE) POLYMERASE GENES

(75) Inventors: Michael Kock, Schifferstadt (DE); Thomas Höger, Edingen-Neckarhausen (DE); Burkhard Kröger, Limburgerhof (DE); Bernd Otterbach, Ludwigshafen (DE); Wilfried Lubisch, Heidelberg (DE); Hans-Georg Lemaire, Limburgerhof (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/778,692

(22) Filed: May 12, 2010

(65) Prior Publication Data

US 2011/0107444 A1 May 5, 2011

Related U.S. Application Data

(63) Continuation of application No. 09/701,586, filed as application No. PCT/EP99/03889 on Jun. 4, 1999, now Pat. No. 7,754,459.

(30) Foreign Application Priority Data

Jun. 5, 1998 (DE) .................. 19825213.7
Mar. 1, 1999 (DE) .................. 19908837.3

(51) Int. Cl.
| C12N 1/20 | (2006.01) |
| C12N 9/10 | (2006.01) |
| A61K 38/00 | (2006.01) |
| A61K 49/00 | (2006.01) |

(52) U.S. Cl.
CPC ........... *C12N 9/1077* (2013.01); *A01K 2217/05* (2013.01); *A61K 38/00* (2013.01); *A61K 49/00* (2013.01); *C07K 2319/00* (2013.01)

(58) Field of Classification Search
None
See application file for complete search history.

(56) References Cited

U.S. PATENT DOCUMENTS

| 5,272,057 A | 12/1993 | Smulson et al. ................ 435/6 |
| 5,534,622 A | 7/1996 | Lehn et al. |
| 6,335,009 B1 | 1/2002 | Bürkle et al. ................ 424/93.2 |

FOREIGN PATENT DOCUMENTS

| FR | 2 707 011 | 12/1994 |
| WO | WO 96/18737 | 6/1996 |

OTHER PUBLICATIONS

Thibodeau et al., FEBS Letters V 264, No. 1, pp. 81-83, 1990.*
Ngo et al. In the Protein Folding Problem and Tertiary Structure Prediction, 1994, Merz et al. (ed.), Birkhauser, Boston, MA, pp. 433 and 492-495.*
Guo et al. (H. Guo et al., "Protein Tolerance to Random Amino Acid Change", PNAS 101(25): 9205-9210, Jun. 2004).*
Helleday,T. and Curtin,N, Accession No. EA489703, GenEmbl Database Apr. 14, 2008.*
Amé et al., "RARP-2, A Novel Mammalian DNA Damage-dependent Poly(ADP-ribose) Poly-merase" J. Biol. Chem. 274(25), 17860-17868 (1999).
Beneke et al., "Isolation of cDNA Encoding Full-length Rat (*Rattus norvegicus*) Poly(ADP-Ribose) Polymerase" Biochem. Mol. Biol. Int. 43(4), 755-761 (1997).
Berghammer et al., "pA DPRT-2: a novel mammalian polymerizing (ADP-ribosyl)transferase gene re-lated to truncated pADPRT homologues in plants and *Caenorhabditis elegans*" FEBS Letters 449, 259-263 (1999).
Griffin et al., "Novel potent inhibitors of the DNA repair enzyme poly(ADP-robose)polymerase (PARP)" Anti-Cancer Drug Design 10, 507-514 (1995).
Johanson, "A human Poly(ADP) Polymerase Gene Family (ADPRTL): cDNA Cloning of Two Novel Poly(ADP-ribose)Polymerase Homologues" Genomics 57, 442-445 (1999).
Küpper et al., "Expression of the DNA-Binding Domain of Human Poly(ADP-Ribose) Polymerase as a *Trans*-Dominant Inhibitor of Poly(ADP-Ribosyl)ation in Transfected Eucariotic Cell Lines" Poirier and Moreau, Eds., Springer, New York, pp. 38-46 (1992).
Lepiniec et al., "Characterization of an *Arabidopsis thaliana* cDNA homologue to animal poly(ADP-ribose) polymerase" FEBS Letters 364, 103-108 (1995).
Pearson et al., "Improved tools for biological sequence comparison" Proc. Natl. Acad. Sci. 85, 2444-2448 (1988).
Wang et al., "PARP is important for genomic stability but dispensable in apoptosis" Genes & Development 11, 2347-2358 (1997).
XP002129091, NCII-CGAP-Ov2 *Homo sapiens* cDNA clone Image:1374175 similar to gb: J03473 NAD (+) ADP-Ribosyltransferase (Human) (1998).
XP002129092, Soares pregnant uterus NbHPU *Homo sapiens* cDNA clone 505009 5' similar to SW:PPOL-XENLA P31669 NAD ( + ) ADP-Ribosyltransferase (1996).
Aposhian H.V. and Kornberg A., "Enzymatic Synthesis of Deoxyribonucleic Acid" J. Biol. Chern., 237, 519-525 (1962).
Ausabel, F., et al., ed., Current Protocols in Molecular Biology, Wiley Interscience, New York 1997.

(Continued)

*Primary Examiner* — Richard Hutson
(74) *Attorney, Agent, or Firm* — Lisa V. Mueller; Michael Best & Friedrich LLP

(57) ABSTRACT

The invention relates to poly(ADP-ribose)polymerase (PARP) homologs which have an amino acid sequence which has
a) a functional NAD binding domain and
b) no zinc finger sequence motif of the general formula $CX_2CX_mHX_2C$ in which
m is an integral value from 28 or 30, and the X radicals are, independently of one another, any amino acid;
and the functional equivalents thereof; nucleic acids coding therefor; antibodies with specificity for the novel protein; pharmaceutical and gene therapy compositions which comprise products according to the invention; methods for the analytical determination of the proteins and nucleic acids according to the invention; methods for identifying effectors or binding partners of the proteins according to the invention; novel PARP effectors; and methods for determining the activity of such effectors.

4 Claims, 7 Drawing Sheets

(56) References Cited

OTHER PUBLICATIONS

Banasik, M., et al. "Specific Inhibitors of Poly(ADP-Ribose) Synthetase and Mono(ADP-Ribosyl)transferase" (1992) J. Biol. Chem., 267, 3, 1569-1575.

Breitling, F. and Dubel, S., "The antigen-binding domain of a human IgG-anti-F(ab*)2 autoantibody" Rekombinante Antikorper (1997), Spektrum Akademischer Verlag, Heidelberg, 1902-1907.

Burtscher et al., "Isolation of ADP-Ribosyltransferase by Affinity Chromatography" Anal Biochem 1986, 152:285-290.

Campbell, A.M., Monoclonal Antibody Technology, (1987) Elsevier Verlag, Amsterdam, New York, Oxford (8 pages).

Chen et al. "A Model of Focal Ischemic Stroke in the Rat: Reproducible Extensive Cortical Infarction" Stroke 17:738-743; 1986.

Choi, D.W., "At the scene of ischemic brain injury: Is PARP a perp?" (1997) Nature Medicine, 3, 10, 1073-1074.

De Murcia, G. et al. "Poly(ADP-ribose) polymerase: a molecular nick-senson" (1994) TIBS, 19, 172-176.

Dingledine et al., "Excitatory amino acid receptors in epilepsy" TIPS, 1990, 11, 334-338.

Fields, S. and Song, O. "A novel genetic system to detect protein-protein interactions" (1989) Nature, 340, 245-246.

Glazer, A. N., "Phycobilisomes: Structure and Dynamics" Rev. Microbial., 36, 173-198 (1982).

Harlow, E and Lane, D., 1988, Antibodies: A Laboratory Manual. Cold Spring Harbor (N.Y.) Press.

Heresco-Levy et al., "The role of N-Methyl-D-Aspartate (NMDA) receptor-mediated neurotransmission in the pathophysiology and therapeutics of psychiatric syndromes" Eur Neuropsychopharmacol 1998, 8(2):141-152.

Hicks, J.M., "Fluorescence Immunoassay" Human Pathology, 15 (2), 112-116 (1984).

Jones, J.T. and Sallenger, B.A. "Evaluating and enhancing ribozyme reaction efficiency in mammalian cells" (1997) Nat. Biotechnol. 15, 902-905.

Kanai Y et al. "Comparative studies on antibody and antibody production to poly(ADP-ribose) in mice" (1978) Immunology 34, 501-508.

Kanai Y et al. "Studies on Anti-Poly(Adenosine Diphosphate Ribose) Antibody" (1974) Biochem Biophys Res Comm 59:1, 300-306.

Kawamaitsu H et al. "Monoclonal Antibodies to Poly(adenosine diphosphate ribose) Recognize Different Structures" (1984) Biochemistry 23, 3771-3777.

Kronick, M.N. et al., "Immunoassay Techniques with Fluorescent Phycobiliprotein Conjugates" Clinical Chemistry, 29(9), 1582-1586 (1983).

Kronick, M.N., "The use of phycobiliproteins as fluorescent labels in immunoassay" J. Imm. Meth., 92, 1-13 (1986).

LabPlanet, "Pierce Supersignal Blaze 34095" found at http://www.labplanet.com/pierce-supersignal-blaze-34095.html, on Oct. 12, 2012 pp. 1-3.

Lam, T.T. "The Effect of 3-Aminobenzamide, An Inhibitory of Poly-ADP-Ribsoe Polymerase, on Ischemia/Reperfusion Damage in Rat Retina" (1997), Res. Comm. in Molecular Pathology and Pharmacology, 95, 3, 241-252.

Lehmann "The NMDA Receptor" Drugs of the Future 1989, 14, 1059-1071.

Linskens et al., "Cataloging altered gene expression in young and senescent cells using enhanced differential display" Nucleic Acids Res. 1995, 23 (16): 3244-3251.

Liu et al. "Polyethylene glycol-conjugated superoxide dismutase and catalase reduce ischemic brain injury" Am. J. Physiol. 256: H589-593; 1989.

Lopez, E. et al. "Europium(111) Trisbipyridine Cryptate Label for Time-Resolved Fluorescence Detection of Polymerase Chain Reaction Products Fixed on a Solid Support" Clin. Chem. 39/2, 196-201 (1993).

Luck, J. M., et al., "Further Studies on the Fractionation of Calf Thymus Histone" J. Biol. Chem., 233, 1407-1414 (1958).

MacColl, R. et al., "The Relationship of the Quaternary Structure of Allophycocyanin to Its Spectrum" Arch. Biochem. Biophys., 208 (1), 42-48 (1981).

MacColl, R. et al., Phycobiliproteins, CRC Press, Inc., Boca Raton, Florida (1987).

Martin et al., "Neurodegeneration in excitotoxicity, global cerebral ischemia, and target deprivation: A perspective on the contributions of apoptosis and necrosis" Brain Res Bull 1998; 46(4):281-309.

Masson, M., et al., "XRCC1 Is Specifically Associated with Poly(ADP-Ribose) Polymerase and Negatively Regulates Its Activity following DNA Damage" (1998) Molecular and Cellular Biology, 18, 6, 3563-3571.

Mohamed et al., "Phthalylglycine and phthalylalanine in heterocyclic syntheseis: Synthesis and reactions of 4-substituted-phthalazinones", Indian Journal of Chemistry, 1994, 33, 769-772.

Nellen et al., "What makes an mRNA anti-sense-itive?" (1993) TIBS 18, 419-423.

Nitrocellulose Pore size 45 flill, NOVEX LC 2001, found at http://www.invitrogen.com/1/1/12156-nitrocellulose-0-45-%CE%BCm-pore-size.html, on Oct. 12, 2012 (5 pages).

NOVEX NP 0005, found at http://products.invitrogen.com/ivgn/product/NP0005, on Oct. 12, 2012 (3 pages).

NuPAGE Transfer Buffer (20X) (125 ml) NOVEX NP 0006, found at http://products.invitrogen.com/ivgn/product/NP0006, on Oct. 12, 2012 (3 pages).

NuPAGE 4-12% BisTris, NOVEX NP 0321, found at https://products.invitrogen.com/ivgn/product/NP0321BOX?ICID=search-np0321box, on Oct. 12, 2012 (5 pages).

NuPAGE LDS Sample Buffer (4X), NOVEX NP 0007, found at http://products.invitrogen.com/ivgn/product/NP0007, on Oct. 12, 2012 (5 pages).

NuPAGE MES-Running Buffer, NOVEX NP 0002, found at http://products.invitrogen.com/ivgn/product/NP0002, on Oct. 12, 2012 (4 pages).

PBS, pH 7.4 (Phosphate buffered saline; Gibco, order No. 10010), found at http://products.invitrogen.com/ivgn/product/10010023, on Oct. 12, 2012 (5 pages).

Pierce, Signal BLAZE Chemiluminescent Substrate 34095, found at http://www.labplanet.com/pierce-supersignal-blaze-34095.html, on Oct. 12, 2012.

Pouwels P.H. et al., Ed., "Cloning Vectors" Elsevier, Amsterdam—New York—Oxford, 1985.

Puodzhyunas et al., Derivatives of 4-(Aminomethyl)-1-Phthalazone, Pharm. Chern. J. 1973, 7, 566-570.

Satake et al., "Arginine Peptides Obtained from Thymus Histone Fractions after Partial Hydrolysis with *Streptomyces griseus* Proteinase" J. Biol. Chem, 235, 2801-2809 (1960).

Shah et al., "Methods for Biochemical Study of Poly(ADP-Ribose) Metabolism in Vitro and in Vivo" Analytical Biochemistry 1995, 227, 1-13.

Strauss et al., "Concepts in Gene Therapy" (1997), Walter de Gruyter, publisher pp. 1-14.

Swanson et al. "A Semiautomated Method for Measuring Brain Infarct Volume" Journal of Cerebral Blood Flow and Metabolism, 1990 10:290-293.

Szabo, C., et al. "Endothelial Dysfunction in a Rat Model of Endotoxic Shock" (1997), Journal of Clinical Investigation, 100, 3, 723-735.

Takahashi, K., et al. "Neuroprotective Effects of Inhibiting Poly(ADP-Ribose) Synthetase on Focal Cerebral Ischemia in Rats" (1997), Journal of Cerebral Blood Flow and Metabolism 17, 1137-1142.

Thammapalerd, N. et al., "Application of Local Products R-Phycoerythrin and Monoclonal Antibody as a Flourescent Antibody Probe to Detect Entamoeba Histolytica Trophozoites" Southeast Asian Journal of Tropical Medicine & Public Health, 27(2): 297-303 (1996).

White et al. "The polymerase chain reaction" (1989), Trends Genet. 5, 185-189.

Zingarelli, B., et al., "Protection against myocardial ischemia and reperfusion injury by 3-aminobenzamide, an inhibitor of poly (ADP-ribose) synthetase" (1997) Cardiovascular Research, 36, 205-215.

\* cited by examiner

Majority - SEQ ID NO: 36
human PARP1 - SEQ ID NO: 37
human PARP2 - SEQ ID NO: 38
human PARP3 - SEQ ID NO: 39
murine PARP - SEQ ID NO: 40

Fig. 1(3)

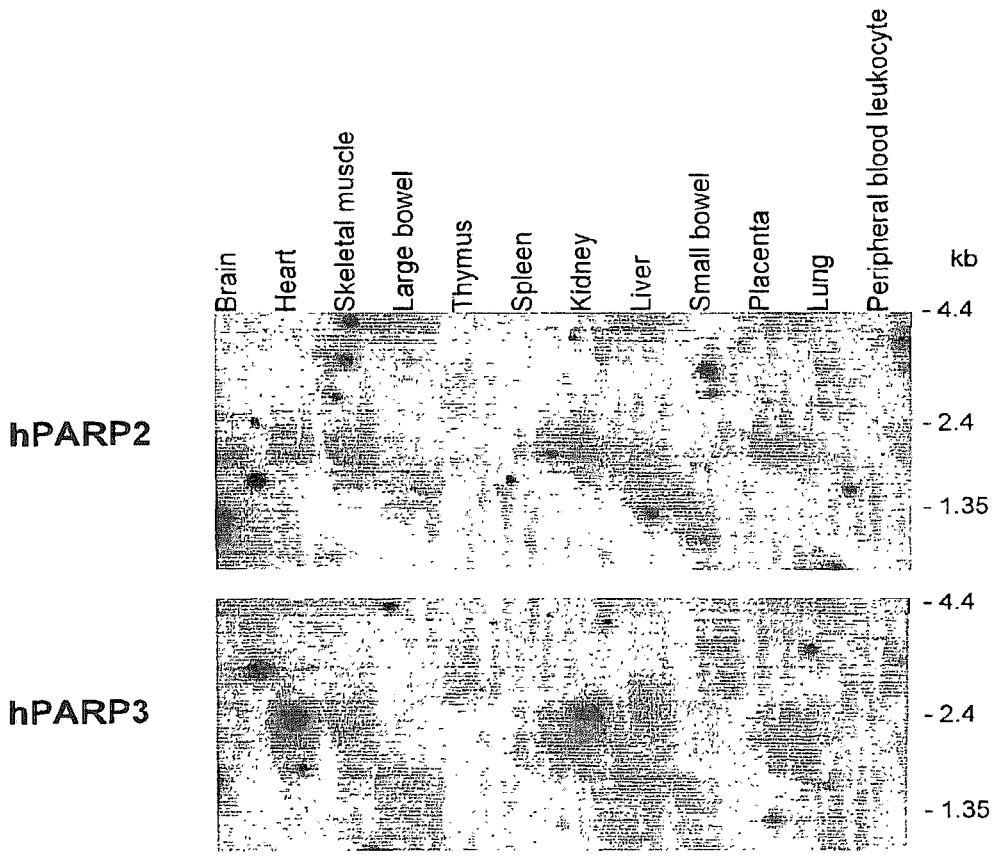
Fig. 2
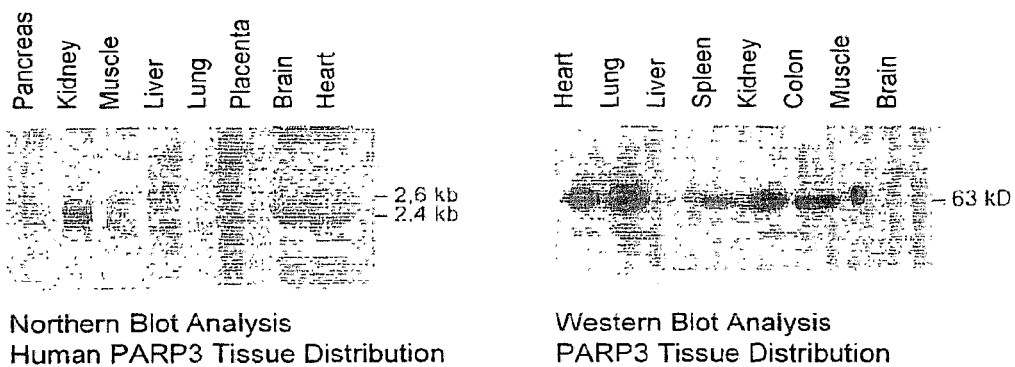
Northern Blot Analysis
Human PARP3 Tissue Distribution
Fig. 3
Western Blot Analysis
PARP3 Tissue Distribution
Fig. 4

HRP = Horseradish-Peroxidase

SEQUENCE LISTING

```
<160> NUMBER OF SEQ ID NOS: 40

<210> SEQ ID NO 1
<211> LENGTH: 1843
<212> TYPE: DNA
<213> ORGANISM: Homo sapiens
<220> FEATURE:
<221> NAME/KEY: CDS
<222> LOCATION: (3)..(1715)
<223> OTHER INFORMATION: product is Poly ADP Ribose Polymerase; from
      brain tissue

<400> SEQUENCE: 1 cc atg gcg gcg cgg cgg cga cgg agc acc ggc ggc ggc agg gcg aga         47
   Met Ala Ala Arg Arg Arg Ser Thr Gly Gly Gly Arg Ala Arg
   1               5                  10                  15 gca tta aat gaa agc aaa aga gtt aat aat ggc aac acg gct cca gaa        95
Ala Leu Asn Glu Ser Lys Arg Val Asn Asn Gly Asn Thr Ala Pro Glu
                20                  25                  30 gac tct tcc cct gcc aag aaa act cgt aga tgc cag aga cag gag tcg       143
Asp Ser Ser Pro Ala Lys Lys Thr Arg Arg Cys Gln Arg Gln Glu Ser
            35                  40                  45 aaa aag atg cct gtg gct gga gga aaa gct aat aag gac agg aca gaa       191
Lys Lys Met Pro Val Ala Gly Gly Lys Ala Asn Lys Asp Arg Thr Glu
        50                  55                  60 gac aag caa gat gaa tct gtg aag gcc ttg ctg tta aag ggc aaa gct       239
Asp Lys Gln Asp Glu Ser Val Lys Ala Leu Leu Lys Gly Lys Ala
    65                  70                  75 cct gtg gac cca gag tgt aca gcc aag gtg ggg aag gct cat gtg tat       287
Pro Val Asp Pro Glu Cys Thr Ala Lys Val Gly Lys Ala His Val Tyr
80                  85                  90                  95
```

-continued

| | |
|---|---|
| tgt gaa gga aat gat gtc tat gat gtc atg cta aat cag acc aat ctc<br>Cys Glu Gly Asn Asp Val Tyr Asp Val Met Leu Asn Gln Thr Asn Leu<br>100                      105                     110 | 335 |
| cag ttc aac aac aac aag tac tat ctg att cag cta tta gaa gat gat<br>Gln Phe Asn Asn Asn Lys Tyr Tyr Leu Ile Gln Leu Leu Glu Asp Asp<br>              115                    120                    125 | 383 |
| gcc cag agg aac ttc agt gtt tgg atg aga tgg ggc cga gtt ggg aaa<br>Ala Gln Arg Asn Phe Ser Val Trp Met Arg Trp Gly Arg Val Gly Lys<br>130                      135                     140 | 431 |
| atg gga cag cac agc ctg gtg gct tgt tca ggc aat ctc aac aag gcc<br>Met Gly Gln His Ser Leu Val Ala Cys Ser Gly Asn Leu Asn Lys Ala<br>145                      150                     155 | 479 |
| aag gaa atc ttt cag aag aaa ttc ctt gac aaa acg aaa aac aat tgg<br>Lys Glu Ile Phe Gln Lys Lys Phe Leu Asp Lys Thr Lys Asn Asn Trp<br>160                   165                   170                   175 | 527 |
| gaa gat cga gaa aag ttt gag aag gtg cct gga aaa tat gat atg cta<br>Glu Asp Arg Glu Lys Phe Glu Lys Val Pro Gly Lys Tyr Asp Met Leu<br>                            180                    185                   190 | 575 |
| cag atg gac tat gcc acc aat act cag gat gaa gag gaa aca aag aaa<br>Gln Met Asp Tyr Ala Thr Asn Thr Gln Asp Glu Glu Glu Thr Lys Lys<br>                         195                    200                    205 | 623 |
| gag gaa tct ctt aaa tct ccc ttg aag cca gag tca cag cta gat ctt<br>Glu Glu Ser Leu Lys Ser Pro Leu Lys Pro Glu Ser Gln Leu Asp Leu<br>          210                    215                    220 | 671 |
| cgg gta cag gag tta ata aag ttg atc tgt aat gtt cag gcc atg gaa<br>Arg Val Gln Glu Leu Ile Lys Leu Ile Cys Asn Val Gln Ala Met Glu<br>225                      230                     235 | 719 |
| gaa atg atg atg gaa atg aag tat aat acc aag aaa gcc cca ctt ggg<br>Glu Met Met Met Glu Met Lys Tyr Asn Thr Lys Lys Ala Pro Leu Gly<br>240                      245                    250                   255 | 767 |
| aag ctg aca gtg gca caa atc aag gca ggt tac cag tct ctt aag aag<br>Lys Leu Thr Val Ala Gln Ile Lys Ala Gly Tyr Gln Ser Leu Lys Lys<br>                            260                    265                   270 | 815 |
| att gag gat tgt att cgg gct ggc cag cat gga cga gct ctc atg gaa<br>Ile Glu Asp Cys Ile Arg Ala Gly Gln His Gly Arg Ala Leu Met Glu<br>                    275                    280                   285 | 863 |
| gca tgc aat gaa ttc tac acc agg att ccg cat gac ttt gga ctc cgt<br>Ala Cys Asn Glu Phe Tyr Thr Arg Ile Pro His Asp Phe Gly Leu Arg<br>290                      295                    300 | 911 |
| act cct cca cta atc cgg aca cag aag gaa ctg tca gaa aaa ata caa<br>Thr Pro Pro Leu Ile Arg Thr Gln Lys Glu Leu Ser Glu Lys Ile Gln<br>305                      310                    315 | 959 |
| tta cta gag gct ttg gga gac att gaa att gct att aag ctg gtg aaa<br>Leu Leu Glu Ala Leu Gly Asp Ile Glu Ile Ala Ile Lys Leu Val Lys<br>320                      325                    330                   335 | 1007 |
| aca gag cta caa agc cca gaa cac cca ttg gac caa cac tat aga aac<br>Thr Glu Leu Gln Ser Pro Glu His Pro Leu Asp Gln His Tyr Arg Asn<br>                            340                    345                   350 | 1055 |
| cta cat tgt gcc ttg cgc ccc ctt gac cat gaa agt tac gag ttc aaa<br>Leu His Cys Ala Leu Arg Pro Leu Asp His Glu Ser Tyr Glu Phe Lys<br>                    355                    360                   365 | 1103 |
| gtg att tcc cag tac cta caa tct acc cat gct ccc aca cac agc gac<br>Val Ile Ser Gln Tyr Leu Gln Ser Thr His Ala Pro Thr His Ser Asp<br>          370                    375                    380 | 1151 |
| tat acc atg acc ttg ctg gat ttg ttt gaa gtg gag aag gat ggt gag<br>Tyr Thr Met Thr Leu Leu Asp Leu Phe Glu Val Glu Lys Asp Gly Glu<br>385                      390                    395 | 1199 |
| aaa gaa gcc ttc aga gag gac ctt cat aac agg atg ctt cta tgg cat<br>Lys Glu Ala Phe Arg Glu Asp Leu His Asn Arg Met Leu Leu Trp His | 1247 |

```
                                                                -continued 400             405             410             415
ggt tcc agg atg agt aac tgg gtg gga atc ttg agc cat ggg ctt cga   1295
Gly Ser Arg Met Ser Asn Trp Val Gly Ile Leu Ser His Gly Leu Arg
            420             425             430 att gcc cca cct gaa gct ccc atc aca ggt tac atg ttt ggg aaa gga   1343
Ile Ala Pro Pro Glu Ala Pro Ile Thr Gly Tyr Met Phe Gly Lys Gly
        435             440             445 atc tac ttt gct gac atg tct tcc aag agt gcc aat tac tgc ttt gcc   1391
Ile Tyr Phe Ala Asp Met Ser Ser Lys Ser Ala Asn Tyr Cys Phe Ala
    450             455             460 tct cgc cta aag aat aca gga ctg ctc ctc tta tca gag gta gct cta   1439
Ser Arg Leu Lys Asn Thr Gly Leu Leu Leu Leu Ser Glu Val Ala Leu
465             470             475 ggt cag tgt aat gaa cta cta gag gcc aat cct aag gcc gaa gga ttg   1487
Gly Gln Cys Asn Glu Leu Leu Glu Ala Asn Pro Lys Ala Glu Gly Leu
480             485             490             495 ctt caa ggt aaa cat agc acc aag ggg ctg ggc aag atg gct ccc agt   1535
Leu Gln Gly Lys His Ser Thr Lys Gly Leu Gly Lys Met Ala Pro Ser
            500             505             510 tct gcc cac ttc gtc acc ctg aat ggg agt aca gtg cca tta gga cca   1583
Ser Ala His Phe Val Thr Leu Asn Gly Ser Thr Val Pro Leu Gly Pro
        515             520             525 gca agt gac aca gga att ctg aat cca gat ggt tat acc ctc aac tac   1631
Ala Ser Asp Thr Gly Ile Leu Asn Pro Asp Gly Tyr Thr Leu Asn Tyr
    530             535             540 aat gaa tat att gta tat aac ccc aac cag gtc cgt atg cgg tac ctt   1679
Asn Glu Tyr Ile Val Tyr Asn Pro Asn Gln Val Arg Met Arg Tyr Leu
545             550             555 tta aag gtt cag ttt aat ttc ctt cag ctg tgg tga atgttgatat        1725
Leu Lys Val Gln Phe Asn Phe Leu Gln Leu Trp
560             565             570 taaataaacc agagatctga tcttcaagca agaaaataag cagtgttgta cttgtgaatt  1785
ttgtgatatt ttatgtaata aaactgtac aggtctaaaa aaaaaaaaaa aaaaaaa      1843

<210> SEQ ID NO 2
<211> LENGTH: 570
<212> TYPE: PRT
<213> ORGANISM: Homo sapiens

<400> SEQUENCE: 2

Met Ala Ala Arg Arg Arg Ser Thr Gly Gly Arg Ala Arg Ala
1               5                   10                  15

Leu Asn Glu Ser Lys Arg Val Asn Asn Gly Asn Thr Ala Pro Glu Asp
                20                  25                  30

Ser Ser Pro Ala Lys Lys Thr Arg Arg Cys Gln Arg Gln Glu Ser Lys
            35                  40                  45

Lys Met Pro Val Ala Gly Gly Lys Ala Asn Lys Asp Arg Thr Glu Asp
        50                  55                  60

Lys Gln Asp Glu Ser Val Lys Ala Leu Leu Leu Lys Gly Lys Ala Pro
65                  70                  75                  80

Val Asp Pro Glu Cys Thr Ala Lys Val Gly Lys Ala His Val Tyr Cys
                85                  90                  95

Glu Gly Asn Asp Val Tyr Asp Val Met Leu Asn Gln Thr Asn Leu Gln
                100                 105                 110

Phe Asn Asn Asn Lys Tyr Tyr Leu Ile Gln Leu Leu Glu Asp Asp Ala
            115                 120                 125

Gln Arg Asn Phe Ser Val Trp Met Arg Trp Gly Arg Val Gly Lys Met
```

```
            130                 135                 140
Gly Gln His Ser Leu Val Ala Cys Ser Gly Asn Leu Asn Lys Ala Lys
145                 150                 155                 160

Glu Ile Phe Gln Lys Lys Phe Leu Asp Lys Thr Lys Asn Asn Trp Glu
                165                 170                 175

Asp Arg Glu Lys Phe Glu Lys Val Pro Gly Lys Tyr Asp Met Leu Gln
            180                 185                 190

Met Asp Tyr Ala Thr Asn Thr Gln Asp Glu Glu Thr Lys Lys Glu
        195                 200                 205

Glu Ser Leu Lys Ser Pro Leu Lys Pro Glu Ser Gln Leu Asp Leu Arg
    210                 215                 220

Val Gln Glu Leu Ile Lys Leu Ile Cys Asn Val Gln Ala Met Glu Glu
225                 230                 235                 240

Met Met Met Glu Met Lys Tyr Asn Thr Lys Lys Ala Pro Leu Gly Lys
                245                 250                 255

Leu Thr Val Ala Gln Ile Lys Ala Gly Tyr Gln Ser Leu Lys Lys Ile
                260                 265                 270

Glu Asp Cys Ile Arg Ala Gly Gln His Gly Arg Ala Leu Met Glu Ala
            275                 280                 285

Cys Asn Glu Phe Tyr Thr Arg Ile Pro His Asp Phe Gly Leu Arg Thr
        290                 295                 300

Pro Pro Leu Ile Arg Thr Gln Lys Glu Leu Ser Glu Lys Ile Gln Leu
305                 310                 315                 320

Leu Glu Ala Leu Gly Asp Ile Glu Ile Ala Ile Lys Leu Val Lys Thr
                325                 330                 335

Glu Leu Gln Ser Pro Glu His Pro Leu Asp Gln His Tyr Arg Asn Leu
                340                 345                 350

His Cys Ala Leu Arg Pro Leu Asp His Glu Ser Tyr Glu Phe Lys Val
            355                 360                 365

Ile Ser Gln Tyr Leu Gln Ser Thr His Ala Pro Thr His Ser Asp Tyr
        370                 375                 380

Thr Met Thr Leu Leu Asp Leu Phe Glu Val Glu Lys Asp Gly Glu Lys
385                 390                 395                 400

Glu Ala Phe Arg Glu Asp Leu His Asn Arg Met Leu Leu Trp His Gly
                405                 410                 415

Ser Arg Met Ser Asn Trp Val Gly Ile Leu Ser His Gly Leu Arg Ile
                420                 425                 430

Ala Pro Pro Glu Ala Pro Ile Thr Gly Tyr Met Phe Gly Lys Gly Ile
            435                 440                 445

Tyr Phe Ala Asp Met Ser Ser Lys Ser Ala Asn Tyr Cys Phe Ala Ser
        450                 455                 460

Arg Leu Lys Asn Thr Gly Leu Leu Leu Leu Ser Glu Val Ala Leu Gly
465                 470                 475                 480

Gln Cys Asn Glu Leu Leu Glu Ala Asn Pro Lys Ala Glu Gly Leu Leu
                485                 490                 495

Gln Gly Lys His Ser Thr Lys Gly Leu Gly Lys Met Ala Pro Ser Ser
                500                 505                 510

Ala His Phe Val Thr Leu Asn Gly Ser Thr Val Pro Leu Gly Pro Ala
            515                 520                 525

Ser Asp Thr Gly Ile Leu Asn Pro Asp Gly Tyr Thr Leu Asn Tyr Asn
        530                 535                 540

Glu Tyr Ile Val Tyr Asn Pro Asn Gln Val Arg Met Arg Tyr Leu Leu
545                 550                 555                 560
```

```
Lys Val Gln Phe Asn Phe Leu Gln Leu Trp
        565                 570

<210> SEQ ID NO 3
<211> LENGTH: 2265
<212> TYPE: DNA
<213> ORGANISM: Homo sapiens
<220> FEATURE:
<221> NAME/KEY: CDS
<222> LOCATION: (242)..(1843)
<223> OTHER INFORMATION: product is Poly ADP Ribose Polymerase; from
      uterus tissue

<400> SEQUENCE: 3
tgggactggt cgcctgactc ggcctgcccc agcctctgct tcaccccact ggtggccaaa    60
tagccgatgt ctaatccccc acacaagctc atccccggcc tctgggattg ttgggaattc   120
tctccctaat tcacgcctga ggctcatgga gagttgctag acctgggact gccctgggag   180
gcgcacacaa ccaggccggg tggcagccag gacctctccc atgtccctgc ttttcttggc   240 c atg gct cca aag ccg aag ccc tgg gta cag act gag ggc cct gag aag    289
  Met Ala Pro Lys Pro Lys Pro Trp Val Gln Thr Glu Gly Pro Glu Lys
  1               5                   10                  15 aag aag ggc cgg cag gca gga agg gag gag gac ccc ttc cgc tcc acc      337
Lys Lys Gly Arg Gln Ala Gly Arg Glu Glu Asp Pro Phe Arg Ser Thr
                20                  25                  30 gct gag gcc ctc aag gcc ata ccc gca gag aag cgc ata atc cgc gtg      385
Ala Glu Ala Leu Lys Ala Ile Pro Ala Glu Lys Arg Ile Ile Arg Val
            35                  40                  45 gat cca aca tgt cca ctc agc agc aac ccc ggg acc cag gtg tat gag      433
Asp Pro Thr Cys Pro Leu Ser Ser Asn Pro Gly Thr Gln Val Tyr Glu
        50                  55                  60 gac tac aac tgc acc ctg aac cag acc aac atc gag aac aac aac          481
Asp Tyr Asn Cys Thr Leu Asn Gln Thr Asn Ile Glu Asn Asn Asn Asn
65                  70                  75                  80 aag ttc tac atc atc cag ctg ctc caa gac agc aac cgc ttc ttc acc      529
Lys Phe Tyr Ile Ile Gln Leu Leu Gln Asp Ser Asn Arg Phe Phe Thr
                85                  90                  95 tgc tgg aac cgc tgg ggc cgt gtg gga gag gtc ggc cag tca aag atc      577
Cys Trp Asn Arg Trp Gly Arg Val Gly Glu Val Gly Gln Ser Lys Ile
                100                 105                 110 aac cac ttc aca agg cta gaa gat gca aag aag gac ttt gag aag aaa      625
Asn His Phe Thr Arg Leu Glu Asp Ala Lys Lys Asp Phe Glu Lys Lys
            115                 120                 125 ttt cgg gaa aag acc aag aac aac tgg gca gag cgg gac cac ttt gtg      673
Phe Arg Glu Lys Thr Lys Asn Asn Trp Ala Glu Arg Asp His Phe Val
        130                 135                 140 tct cac ccg ggc aag tac aca ctt atc gaa gta cag gca gag gat gag      721
Ser His Pro Gly Lys Tyr Thr Leu Ile Glu Val Gln Ala Glu Asp Glu
145                 150                 155                 160 gcc cag gaa gct gtg gtg aag gtg gac aga ggc cca gtg agg act gtg      769
Ala Gln Glu Ala Val Val Lys Val Asp Arg Gly Pro Val Arg Thr Val
                165                 170                 175 act aag cgg gtg cag ccc tgc tcc ctg gac cca gcc acg cag aag ctc      817
Thr Lys Arg Val Gln Pro Cys Ser Leu Asp Pro Ala Thr Gln Lys Leu
            180                 185                 190 atc act aac atc ttc agc aag gag atg ttc aag aac acc atg gcc ctc      865
Ile Thr Asn Ile Phe Ser Lys Glu Met Phe Lys Asn Thr Met Ala Leu
        195                 200                 205 atg gac ctg gat gtg aag aag atg ccc ctg gga aag ctg agc aag caa      913
Met Asp Leu Asp Val Lys Lys Met Pro Leu Gly Lys Leu Ser Lys Gln
```

```
                  210                 215                 220
cag att gca cgg ggt ttc gag gcc ttg gag gcg ctg gag gag gcc ctg         961
Gln Ile Ala Arg Gly Phe Glu Ala Leu Glu Ala Leu Glu Glu Ala Leu
225                 230                 235                 240 aaa ggc ccc acg gat ggt ggc caa agc ctg gag gag ctg tcc tca cac        1009
Lys Gly Pro Thr Asp Gly Gly Gln Ser Leu Glu Glu Leu Ser Ser His
                245                 250                 255 ttt tac acc gtc atc ccg cac aac ttc ggc cac agc cag ccc ccg ccc        1057
Phe Tyr Thr Val Ile Pro His Asn Phe Gly His Ser Gln Pro Pro Pro
            260                 265                 270 atc aat tcc cct gag ctt ctg cag gcc aag aag gac atg ctg ctg gtg        1105
Ile Asn Ser Pro Glu Leu Leu Gln Ala Lys Lys Asp Met Leu Leu Val
        275                 280                 285 ctg gcg gac atc gag ctg gcc cag gcc ctg cag gca gtc tct gag cag        1153
Leu Ala Asp Ile Glu Leu Ala Gln Ala Leu Gln Ala Val Ser Glu Gln
    290                 295                 300 gag aag acg gtg gag gag gtg cca cac ccc ctg gac cga gac tac cag        1201
Glu Lys Thr Val Glu Glu Val Pro His Pro Leu Asp Arg Asp Tyr Gln
305                 310                 315                 320 ctt ctc aag tgc cag ctg cag ctg cta gac tct gga gca cct gag tac        1249
Leu Leu Lys Cys Gln Leu Gln Leu Leu Asp Ser Gly Ala Pro Glu Tyr
                325                 330                 335 aag gtg ata cag acc tac tta gaa cag act ggc agc aac cac agg tgc        1297
Lys Val Ile Gln Thr Tyr Leu Glu Gln Thr Gly Ser Asn His Arg Cys
            340                 345                 350 cct aca ctt caa cac atc tgg aaa gta aac caa gaa ggg gag gaa gac        1345
Pro Thr Leu Gln His Ile Trp Lys Val Asn Gln Glu Gly Glu Glu Asp
        355                 360                 365 aga ttc cag gcc cac tcc aaa ctg ggt aat cgg aag ctg ctg tgg cat        1393
Arg Phe Gln Ala His Ser Lys Leu Gly Asn Arg Lys Leu Leu Trp His
    370                 375                 380 ggc acc aac atg gcc gtg gtg gcc gcc atc ctc act agt ggg ctc cgc        1441
Gly Thr Asn Met Ala Val Val Ala Ala Ile Leu Thr Ser Gly Leu Arg
385                 390                 395                 400 atc atg cca cat tct ggt ggg cgt gtt ggc aag ggc atc tac ttt gcc        1489
Ile Met Pro His Ser Gly Gly Arg Val Gly Lys Gly Ile Tyr Phe Ala
                405                 410                 415 tca gag aac agc aag tca gct gga tat gtt att ggc atg aag tgt ggg        1537
Ser Glu Asn Ser Lys Ser Ala Gly Tyr Val Ile Gly Met Lys Cys Gly
            420                 425                 430 gcc cac cat gtc ggc tac atg ttc ctg ggt gag gtg gcc ctg ggc aga        1585
Ala His His Val Gly Tyr Met Phe Leu Gly Glu Val Ala Leu Gly Arg
        435                 440                 445 gag cac cat atc aac acg gac aac ccc agc ttg aag agc cca cct cct        1633
Glu His His Ile Asn Thr Asp Asn Pro Ser Leu Lys Ser Pro Pro Pro
    450                 455                 460 ggc ttc gac agt gtc att gcc cga ggc cac acc gag cct gat ccg acc        1681
Gly Phe Asp Ser Val Ile Ala Arg Gly His Thr Glu Pro Asp Pro Thr
465                 470                 475                 480 cag gac act gag ttg gag ctg gat ggc cag caa gtg gtg gtg ccc cag        1729
Gln Asp Thr Glu Leu Glu Leu Asp Gly Gln Gln Val Val Val Pro Gln
                485                 490                 495 ggc cag cct gtg ccc tgc cca gag ttc agc agc tcc aca ttc tcc cag        1777
Gly Gln Pro Val Pro Cys Pro Glu Phe Ser Ser Ser Thr Phe Ser Gln
            500                 505                 510 agc gag tac ctc atc tac cag gag agc cag tgt cgc ctg cgc tac ctg        1825
Ser Glu Tyr Leu Ile Tyr Gln Glu Ser Gln Cys Arg Leu Arg Tyr Leu
        515                 520                 525 ctg gag gtc cac ctc tga gtgcccgccc tgtcccccgg ggtcctgcaa               1873
```

-continued

```
Leu Glu Val His Leu
    530 ggctggactg tgatcttcaa tcatcctgcc catctctggt accctatat cactccttt      1933 tttcaagaat acaatacgtt gttgttaact atagtcacca tgctgtacaa gatccctgaa    1993 cttatgcctc ctaactgaaa ttttgtattc tttgacacat ctgcccagtc cctctcctcc    2053 cagcccatgg taaccagcat ttgactcttt acttgtataa gggcagcttt tataggttcc    2113 acatgtaagt gagatcatgc agtgtttgtc tttctgtgcc tggcttattt cactcagcat    2173 aatgtgcacc gggttcaccc atgttttcat aaatgacaag atttcctcct taaaaaaaa    2233 aaaaaaaaa aaaaaaaaaa aaaaaaaaaa aa                                   2265

<210> SEQ ID NO 4
<211> LENGTH: 533
<212> TYPE: PRT
<213> ORGANISM: Homo sapiens

<400> SEQUENCE: 4

Met Ala Pro Lys Pro Lys Pro Trp Val Gln Thr Glu Gly Pro Glu Lys
 1               5                  10                  15

Lys Lys Gly Arg Gln Ala Gly Arg Glu Glu Asp Pro Phe Arg Ser Thr
            20                  25                  30

Ala Glu Ala Leu Lys Ala Ile Pro Ala Glu Lys Arg Ile Ile Arg Val
        35                  40                  45

Asp Pro Thr Cys Pro Leu Ser Ser Asn Pro Gly Thr Gln Val Tyr Glu
    50                  55                  60

Asp Tyr Asn Cys Thr Leu Asn Gln Thr Asn Ile Glu Asn Asn Asn Asn
65                  70                  75                  80

Lys Phe Tyr Ile Ile Gln Leu Leu Gln Asp Ser Asn Arg Phe Phe Thr
                85                  90                  95

Cys Trp Asn Arg Trp Gly Arg Val Gly Glu Val Gly Gln Ser Lys Ile
            100                 105                 110

Asn His Phe Thr Arg Leu Glu Asp Ala Lys Lys Asp Phe Glu Lys Lys
        115                 120                 125

Phe Arg Glu Lys Thr Lys Asn Asn Trp Ala Glu Arg Asp His Phe Val
    130                 135                 140

Ser His Pro Gly Lys Tyr Thr Leu Ile Glu Val Gln Ala Glu Asp Glu
145                 150                 155                 160

Ala Gln Glu Ala Val Val Lys Val Asp Arg Gly Pro Val Arg Thr Val
                165                 170                 175

Thr Lys Arg Val Gln Pro Cys Ser Leu Asp Pro Ala Thr Gln Lys Leu
            180                 185                 190

Ile Thr Asn Ile Phe Ser Lys Glu Met Phe Lys Asn Thr Met Ala Leu
        195                 200                 205

Met Asp Leu Asp Val Lys Lys Met Pro Leu Gly Lys Leu Ser Lys Gln
    210                 215                 220

Gln Ile Ala Arg Gly Phe Glu Ala Leu Glu Ala Leu Glu Glu Ala Leu
225                 230                 235                 240

Lys Gly Pro Thr Asp Gly Gly Gln Ser Leu Glu Glu Leu Ser Ser His
                245                 250                 255

Phe Tyr Thr Val Ile Pro His Asn Phe Gly His Ser Gln Pro Pro Pro
            260                 265                 270

Ile Asn Ser Pro Glu Leu Leu Gln Ala Lys Lys Asp Met Leu Leu Val
        275                 280                 285
```

```
Leu Ala Asp Ile Glu Leu Ala Gln Ala Leu Gln Ala Val Ser Glu Gln
    290                 295                 300
Glu Lys Thr Val Glu Glu Val Pro His Pro Leu Asp Arg Asp Tyr Gln
305                 310                 315                 320
Leu Leu Lys Cys Gln Leu Gln Leu Leu Asp Ser Gly Ala Pro Glu Tyr
            325                 330                 335
Lys Val Ile Gln Thr Tyr Leu Glu Gln Thr Gly Ser Asn His Arg Cys
        340                 345                 350
Pro Thr Leu Gln His Ile Trp Lys Val Asn Gln Glu Gly Glu Glu Asp
    355                 360                 365
Arg Phe Gln Ala His Ser Lys Leu Gly Asn Arg Lys Leu Leu Trp His
370                 375                 380
Gly Thr Asn Met Ala Val Val Ala Ala Ile Leu Thr Ser Gly Leu Arg
385                 390                 395                 400
Ile Met Pro His Ser Gly Gly Arg Val Gly Lys Gly Ile Tyr Phe Ala
            405                 410                 415
Ser Glu Asn Ser Lys Ser Ala Gly Tyr Val Ile Gly Met Lys Cys Gly
        420                 425                 430
Ala His His Val Gly Tyr Met Phe Leu Gly Glu Val Ala Leu Gly Arg
    435                 440                 445
Glu His His Ile Asn Thr Asp Asn Pro Ser Leu Lys Ser Pro Pro Pro
450                 455                 460
Gly Phe Asp Ser Val Ile Ala Arg Gly His Thr Glu Pro Asp Pro Thr
465                 470                 475                 480
Gln Asp Thr Glu Leu Glu Leu Asp Gly Gln Gln Val Val Val Pro Gln
            485                 490                 495
Gly Gln Pro Val Pro Cys Pro Glu Phe Ser Ser Ser Thr Phe Ser Gln
        500                 505                 510
Ser Glu Tyr Leu Ile Tyr Gln Glu Ser Gln Cys Arg Leu Arg Tyr Leu
    515                 520                 525
Leu Glu Val His Leu
    530

<210> SEQ ID NO 5
<211> LENGTH: 2265
<212> TYPE: DNA
<213> ORGANISM: Homo sapiens
<220> FEATURE:
<221> NAME/KEY: CDS
<222> LOCATION: (221)..(1843)
<223> OTHER INFORMATION: product is Poly ADP Ribose Polymerase; from
      uterus tissue

<400> SEQUENCE: 5
tgggactggt cgcctgactc ggcctgcccc agcctctgct tcaccccact ggtggccaaa      60
tagccgatgt ctaatccccc acacaagctc atccccggcc tctgggattg ttgggaattc     120
tctccctaat tcacgcctga ggctcatgga gagttgctag acctgggact gccctgggag     180
gcgcacacaa ccaggccggg tggcagccag gacctctccc atg tcc ctg ctt ttc      235
                                              Met Ser Leu Leu Phe
                                              1               5 ttg gcc atg gct cca aag ccg aag ccc tgg gta cag act gag ggc cct      283
Leu Ala Met Ala Pro Lys Pro Lys Pro Trp Val Gln Thr Glu Gly Pro
            10                  15                  20 gag aag aag aag ggc cgg cag gca gga agg gag gag gac ccc ttc cgc      331
Glu Lys Lys Lys Gly Arg Gln Ala Gly Arg Glu Glu Asp Pro Phe Arg
        25                  30                  35
```

-continued

| | | |
|---|---|---|
| tcc acc gct gag gcc ctc aag gcc ata ccc gca gag aag cgc ata atc<br>Ser Thr Ala Glu Ala Leu Lys Ala Ile Pro Ala Glu Lys Arg Ile Ile<br>        40                          45                        50 | 379 | |
| cgc gtg gat cca aca tgt cca ctc agc agc aac ccc ggg acc cag gtg<br>Arg Val Asp Pro Thr Cys Pro Leu Ser Ser Asn Pro Gly Thr Gln Val<br>   55                          60                       65 | 427 | |
| tat gag gac tac aac tgc acc ctg aac cag acc aac atc gag aac aac<br>Tyr Glu Asp Tyr Asn Cys Thr Leu Asn Gln Thr Asn Ile Glu Asn Asn<br>70                       75                     80                   85 | 475 | |
| aac aac aag ttc tac atc atc cag ctg ctc caa gac agc aac cgc ttc<br>Asn Asn Lys Phe Tyr Ile Ile Gln Leu Leu Gln Asp Ser Asn Arg Phe<br>              90                       95                    100 | 523 | |
| ttc acc tgc tgg aac cgc tgg ggc cgt gtg gga gag gtc ggc cag tca<br>Phe Thr Cys Trp Asn Arg Trp Gly Arg Val Gly Glu Val Gly Gln Ser<br>         105                     110                  115 | 571 | |
| aag atc aac cac ttc aca agg cta gaa gat gca aag aag gac ttt gag<br>Lys Ile Asn His Phe Thr Arg Leu Glu Asp Ala Lys Lys Asp Phe Glu<br>               120                     125                  130 | 619 | |
| aag aaa ttt cgg gaa aag acc aag aac aac tgg gca gag cgg gac cac<br>Lys Lys Phe Arg Glu Lys Thr Lys Asn Asn Trp Ala Glu Arg Asp His<br>135                      140                     145 | 667 | |
| ttt gtg tct cac ccg ggc aag tac aca ctt atc gaa gta cag gca gag<br>Phe Val Ser His Pro Gly Lys Tyr Thr Leu Ile Glu Val Gln Ala Glu<br>150                      155                     160                   165 | 715 | |
| gat gag gcc cag gaa gct gtg gtg aag gtg gac aga ggc cca gtg agg<br>Asp Glu Ala Gln Glu Ala Val Val Lys Val Asp Arg Gly Pro Val Arg<br>               170                     175                  180 | 763 | |
| act gtg act aag cgg gtg cag ccc tgc tcc ctg gac cca gcc acg cag<br>Thr Val Thr Lys Arg Val Gln Pro Cys Ser Leu Asp Pro Ala Thr Gln<br>                   185                     190                  195 | 811 | |
| aag ctc atc act aac atc ttc agc aag gag atg ttc aag aac acc atg<br>Lys Leu Ile Thr Asn Ile Phe Ser Lys Glu Met Phe Lys Asn Thr Met<br>               200                     205                  210 | 859 | |
| gcc ctc atg gac ctg gat gtg aag aag atg ccc ctg gga aag ctg agc<br>Ala Leu Met Asp Leu Asp Val Lys Lys Met Pro Leu Gly Lys Leu Ser<br>215                      220                     225 | 907 | |
| aag caa cag att gca cgg ggt ttc gag gcc ttg gag gcg ctg gag gag<br>Lys Gln Gln Ile Ala Arg Gly Phe Glu Ala Leu Glu Ala Leu Glu Glu<br>230                      235                     240                   245 | 955 | |
| gcc ctg aaa ggc ccc acg gat ggt ggc caa agc ctg gag gag ctg tcc<br>Ala Leu Lys Gly Pro Thr Asp Gly Gly Gln Ser Leu Glu Glu Leu Ser<br>               250                     255                  260 | 1003 | |
| tca cac ttt tac acc gtc atc ccg cac aac ttc ggc cac agc cag ccc<br>Ser His Phe Tyr Thr Val Ile Pro His Asn Phe Gly His Ser Gln Pro<br>                   265                     270                  275 | 1051 | |
| ccg ccc atc aat tcc cct gag ctt ctg cag gcc aag aag gac atg ctg<br>Pro Pro Ile Asn Ser Pro Glu Leu Leu Gln Ala Lys Lys Asp Met Leu<br>               280                     285                  290 | 1099 | |
| ctg gtg ctg gcg gac atc gag ctg gcc cag gcc ctg cag gca gtc tct<br>Leu Val Leu Ala Asp Ile Glu Leu Ala Gln Ala Leu Gln Ala Val Ser<br>295                      300                     305 | 1147 | |
| gag cag gag aag acg gtg gag gag gtg cca cac ccc ctg gac cga gac<br>Glu Gln Glu Lys Thr Val Glu Glu Val Pro His Pro Leu Asp Arg Asp<br>310                      315                     320                   325 | 1195 | |
| tac cag ctt ctc aag tgc cag ctg cag ctg cta gac tct gga gca cct<br>Tyr Gln Leu Leu Lys Cys Gln Leu Gln Leu Leu Asp Ser Gly Ala Pro<br>                   330                     335                  340 | 1243 | |
| gag tac aag gtg ata cag acc tac tta gaa cag act ggc agc aac cac<br>Glu Tyr Lys Val Ile Gln Thr Tyr Leu Glu Gln Thr Gly Ser Asn His<br>               345                     350                  355 | 1291 | |

```
agg tgc cct aca ctt caa cac atc tgg aaa gta aac caa gaa ggg gag    1339
Arg Cys Pro Thr Leu Gln His Ile Trp Lys Val Asn Gln Glu Gly Glu
        360                 365                 370 gaa gac aga ttc cag gcc cac tcc aaa ctg ggt aat cgg aag ctg ctg    1387
Glu Asp Arg Phe Gln Ala His Ser Lys Leu Gly Asn Arg Lys Leu Leu
375                 380                 385 tgg cat ggc acc aac atg gcc gtg gtg gcc gcc atc ctc act agt ggg    1435
Trp His Gly Thr Asn Met Ala Val Val Ala Ala Ile Leu Thr Ser Gly
390                 395                 400                 405 ctc cgc atc atg cca cat tct ggt ggg cgt gtt ggc aag ggc atc tac    1483
Leu Arg Ile Met Pro His Ser Gly Gly Arg Val Gly Lys Gly Ile Tyr
                410                 415                 420 ttt gcc tca gag aac agc aag tca gct gga tat gtt att ggc atg aag    1531
Phe Ala Ser Glu Asn Ser Lys Ser Ala Gly Tyr Val Ile Gly Met Lys
            425                 430                 435 tgt ggg gcc cac cat gtc ggc tac atg ttc ctg ggt gag gtg gcc ctg    1579
Cys Gly Ala His His Val Gly Tyr Met Phe Leu Gly Glu Val Ala Leu
        440                 445                 450 ggc aga gag cac cat atc aac acg gac aac ccc agc ttg aag agc cca    1627
Gly Arg Glu His His Ile Asn Thr Asp Asn Pro Ser Leu Lys Ser Pro
    455                 460                 465 cct cct ggc ttc gac agt gtc att gcc cga ggc cac acc gag cct gat    1675
Pro Pro Gly Phe Asp Ser Val Ile Ala Arg Gly His Thr Glu Pro Asp
470                 475                 480                 485 ccg acc cag gac act gag ttg gag ctg gat ggc cag caa gtg gtg gtg    1723
Pro Thr Gln Asp Thr Glu Leu Glu Leu Asp Gly Gln Gln Val Val Val
                490                 495                 500 ccc cag ggc cag cct gtg ccc tgc cca gag ttc agc agc tcc aca ttc    1771
Pro Gln Gly Gln Pro Val Pro Cys Pro Glu Phe Ser Ser Ser Thr Phe
            505                 510                 515 tcc cag agc gag tac ctc atc tac cag gag agc cag tgt cgc ctg cgc    1819
Ser Gln Ser Glu Tyr Leu Ile Tyr Gln Glu Ser Gln Cys Arg Leu Arg
        520                 525                 530 tac ctg ctg gag gtc cac ctc tga gtgcccgccc tgtccccgg ggtcctgcaa    1873
Tyr Leu Leu Glu Val His Leu
    535                 540 ggctggactg tgatcttcaa tcatcctgcc catctctggt accctatat cactcctttt    1933 tttcaagaat acaatacgtt gttgttaact atagtcacca tgctgtacaa gatccctgaa    1993
cttatgcctc ctaactgaaa ttttgtattc tttgacacat ctgcccagtc cctcctctcc    2053
cagcccatgg taaccagcat ttgactcttt acttgtataa gggcagcttt tataggttcc    2113
acatgtaagt gagatcatgc agtgtttgtc tttctgtgcc tggcttattt cactcagcat    2173
aatgtgcacc gggttcaccc atgttttcat aaatgacaag atttcctcct ttaaaaaaaa    2233 aaaaaaaaa aaaaaaaaaa aaaaaaaaaa aa                                  2265

<210> SEQ ID NO 6
<211> LENGTH: 540
<212> TYPE: PRT
<213> ORGANISM: Homo sapiens

<400> SEQUENCE: 6

Met Ser Leu Leu Phe Leu Ala Met Ala Pro Lys Pro Lys Pro Trp Val
1               5                   10                  15

Gln Thr Glu Gly Pro Glu Lys Lys Gly Arg Gln Ala Gly Arg Glu
            20                  25                  30

Glu Asp Pro Phe Arg Ser Thr Ala Glu Ala Leu Lys Ala Ile Pro Ala
        35                  40                  45
```

```
Glu Lys Arg Ile Ile Arg Val Asp Pro Thr Cys Pro Leu Ser Ser Asn
 50                  55                  60

Pro Gly Thr Gln Val Tyr Glu Asp Tyr Asn Cys Thr Leu Asn Gln Thr
 65                  70                  75                  80

Asn Ile Glu Asn Asn Asn Lys Phe Tyr Ile Ile Gln Leu Leu Gln
                     85                  90                  95

Asp Ser Asn Arg Phe Phe Thr Cys Trp Asn Arg Trp Gly Arg Val Gly
                100                 105                 110

Glu Val Gly Gln Ser Lys Ile Asn His Phe Thr Arg Leu Glu Asp Ala
            115                 120                 125

Lys Lys Asp Phe Glu Lys Lys Phe Arg Glu Lys Thr Lys Asn Asn Trp
130                 135                 140

Ala Glu Arg Asp His Phe Val Ser His Pro Gly Lys Tyr Thr Leu Ile
145                 150                 155                 160

Glu Val Gln Ala Glu Asp Glu Ala Gln Glu Ala Val Val Lys Val Asp
                165                 170                 175

Arg Gly Pro Val Arg Thr Val Thr Lys Arg Val Gln Pro Cys Ser Leu
            180                 185                 190

Asp Pro Ala Thr Gln Lys Leu Ile Thr Asn Ile Phe Ser Lys Glu Met
        195                 200                 205

Phe Lys Asn Thr Met Ala Leu Met Asp Leu Asp Val Lys Lys Met Pro
210                 215                 220

Leu Gly Lys Leu Ser Lys Gln Gln Ile Ala Arg Gly Phe Glu Ala Leu
225                 230                 235                 240

Glu Ala Leu Glu Glu Ala Leu Lys Gly Pro Thr Asp Gly Gly Gln Ser
                245                 250                 255

Leu Glu Glu Leu Ser Ser His Phe Tyr Thr Val Ile Pro His Asn Phe
            260                 265                 270

Gly His Ser Gln Pro Pro Ile Asn Ser Pro Glu Leu Leu Gln Ala
        275                 280                 285

Lys Lys Asp Met Leu Leu Val Leu Ala Asp Ile Glu Leu Ala Gln Ala
290                 295                 300

Leu Gln Ala Val Ser Glu Gln Glu Lys Thr Val Glu Glu Val Pro His
305                 310                 315                 320

Pro Leu Asp Arg Asp Tyr Gln Leu Leu Lys Cys Gln Leu Gln Leu Leu
                325                 330                 335

Asp Ser Gly Ala Pro Glu Tyr Lys Val Ile Gln Thr Tyr Leu Glu Gln
            340                 345                 350

Thr Gly Ser Asn His Arg Cys Pro Thr Leu Gln His Ile Trp Lys Val
        355                 360                 365

Asn Gln Glu Gly Glu Glu Asp Arg Phe Gln Ala His Ser Lys Leu Gly
370                 375                 380

Asn Arg Lys Leu Leu Trp His Gly Thr Asn Met Ala Val Val Ala Ala
385                 390                 395                 400

Ile Leu Thr Ser Gly Leu Arg Ile Met Pro His Ser Gly Gly Arg Val
                405                 410                 415

Gly Lys Gly Ile Tyr Phe Ala Ser Glu Asn Ser Lys Ser Ala Gly Tyr
            420                 425                 430

Val Ile Gly Met Lys Cys Gly Ala His His Val Gly Tyr Met Phe Leu
        435                 440                 445

Gly Glu Val Ala Leu Gly Arg Glu His His Ile Asn Thr Asp Asn Pro
450                 455                 460
```

```
Ser Leu Lys Ser Pro Pro Gly Phe Asp Ser Val Ile Ala Arg Gly
465                 470                 475                 480

His Thr Glu Pro Asp Pro Thr Gln Asp Thr Glu Leu Glu Leu Asp Gly
                485                 490                 495

Gln Gln Val Val Val Pro Gln Gly Gln Pro Val Pro Cys Pro Glu Phe
            500                 505                 510

Ser Ser Ser Thr Phe Ser Gln Ser Glu Tyr Leu Ile Tyr Gln Glu Ser
            515                 520                 525

Gln Cys Arg Leu Arg Tyr Leu Leu Glu Val His Leu
530                 535                 540

<210> SEQ ID NO 7
<211> LENGTH: 1740
<212> TYPE: DNA
<213> ORGANISM: Mus musculus
<220> FEATURE:
<221> NAME/KEY: CDS
<222> LOCATION: (112)..(1710)

<400> SEQUENCE: 7
cccggctttc acttttctg ctgcctcggg aacacctcg agccaactgc ttcctaactc      60
agggtgggca gaactgacgg gatctaagct tctgcatctc tgaggagaac c atg gct    117
                                                          Met Ala
                                                          1 cca aaa cga aag gcc tct gtg cag act gag ggc tcc aag aag cag cga    165
Pro Lys Arg Lys Ala Ser Val Gln Thr Glu Gly Ser Lys Lys Gln Arg
        5                   10                  15 caa ggg aca gag gag gag gac agc ttc cgg tcc act gcc gag gct ctc    213
Gln Gly Thr Glu Glu Glu Asp Ser Phe Arg Ser Thr Ala Glu Ala Leu
    20                  25                  30 aga gca gca cct gct gat aat cgg gtc atc cgt gtg gac ccc tca tgt    261
Arg Ala Ala Pro Ala Asp Asn Arg Val Ile Arg Val Asp Pro Ser Cys
35                  40                  45                  50 cca ttc agc cgg aac ccc ggg ata cag gtc cac gag gac tat gac tgt    309
Pro Phe Ser Arg Asn Pro Gly Ile Gln Val His Glu Asp Tyr Asp Cys
                55                  60                  65 acc ctg aac cag acc aac atc ggc aac aac aac aag ttc tat att       357
Thr Leu Asn Gln Thr Asn Ile Gly Asn Asn Asn Lys Phe Tyr Ile
            70                  75                  80 atc caa ctg ctg gag gag ggt agt cgc ttc ttc tgc tgg aat cgc tgg    405
Ile Gln Leu Leu Glu Glu Gly Ser Arg Phe Phe Cys Trp Asn Arg Trp
        85                  90                  95 ggc cgc gtg gga gag gtg ggc cag agc aag atg aac cac ttc acc tgc    453
Gly Arg Val Gly Glu Val Gly Gln Ser Lys Met Asn His Phe Thr Cys
    100                 105                 110 ctg gaa gat gca aag aag gac ttt aag aag aaa ttt tgg gag aag act    501
Leu Glu Asp Ala Lys Lys Asp Phe Lys Lys Lys Phe Trp Glu Lys Thr
115                 120                 125                 130 aaa aac aaa tgg gag gag cgg gac cgt ttt gtg gcc cag ccc aac aag    549
Lys Asn Lys Trp Glu Glu Arg Asp Arg Phe Val Ala Gln Pro Asn Lys
                135                 140                 145 tac aca ctt ata gaa gtc cag gga gaa gca gag agc caa gag gct gta    597
Tyr Thr Leu Ile Glu Val Gln Gly Glu Ala Glu Ser Gln Glu Ala Val
            150                 155                 160 gtg aag gcc tta tct ccc cag gtg gac agc ggc cct gtg agg acc gtg    645
Val Lys Ala Leu Ser Pro Gln Val Asp Ser Gly Pro Val Arg Thr Val
        165                 170                 175 gtc aag ccc tgc tcc cta gac cct gcc acc cag aac ctt atc acc aac    693
Val Lys Pro Cys Ser Leu Asp Pro Ala Thr Gln Asn Leu Ile Thr Asn
    180                 185                 190
```

```
atc ttc agc aaa gag atg ttc aag aac gca atg acc ctc atg aac ctg        741
Ile Phe Ser Lys Glu Met Phe Lys Asn Ala Met Thr Leu Met Asn Leu
195                 200                 205                 210 gat gtg aag aag atg ccc ttg gga aag ctg acc aag cag cag att gcc        789
Asp Val Lys Lys Met Pro Leu Gly Lys Leu Thr Lys Gln Gln Ile Ala
            215                 220                 225 cgt ggc ttc gag gcc ttg gaa gct cta gag gag gcc atg aaa aac ccc        837
Arg Gly Phe Glu Ala Leu Glu Ala Leu Glu Glu Ala Met Lys Asn Pro
        230                 235                 240 aca ggg gat ggc cag agc ctg gaa gag ctc tcc tcc tgc ttc tac act        885
Thr Gly Asp Gly Gln Ser Leu Glu Glu Leu Ser Ser Cys Phe Tyr Thr
    245                 250                 255 gtc atc cca cac aac ttc ggc cgc agc cga ccc ccg ccc atc aac tcc        933
Val Ile Pro His Asn Phe Gly Arg Ser Arg Pro Pro Pro Ile Asn Ser
260                 265                 270 cct gat gtg ctt cag gcc aag aag gac atg ctg ctg gtg cta gcg gac        981
Pro Asp Val Leu Gln Ala Lys Lys Asp Met Leu Leu Val Leu Ala Asp
275                 280                 285                 290 atc gag ttg gcg cag acc ttg cag gca gcc cct ggg gag gag gag gag       1029
Ile Glu Leu Ala Gln Thr Leu Gln Ala Ala Pro Gly Glu Glu Glu Glu
            295                 300                 305 aaa gtg gaa gag gtg cca cac cca ctg gat cga gac tac cag ctc ctc       1077
Lys Val Glu Glu Val Pro His Pro Leu Asp Arg Asp Tyr Gln Leu Leu
        310                 315                 320 agg tgc cag ctt caa ctg ctg gac tcc ggg gag tcc gag tac aag gca       1125
Arg Cys Gln Leu Gln Leu Leu Asp Ser Gly Glu Ser Glu Tyr Lys Ala
    325                 330                 335 ata cag acc tac ctg aaa cag act ggc aac agc tac agg tgc cca aac       1173
Ile Gln Thr Tyr Leu Lys Gln Thr Gly Asn Ser Tyr Arg Cys Pro Asn
340                 345                 350 ctg cgg cat gtt tgg aaa gtg aac cga gaa ggg gag gga gac agg ttc       1221
Leu Arg His Val Trp Lys Val Asn Arg Glu Gly Glu Gly Asp Arg Phe
355                 360                 365                 370 cag gcc cac tcc aaa ctg ggc aat cgg agg ctg ctg tgg cac ggc acc       1269
Gln Ala His Ser Lys Leu Gly Asn Arg Arg Leu Leu Trp His Gly Thr
            375                 380                 385 aat gtg gcc gtg gtg gct gcc atc ctc acc agt ggg ctc cga atc atg       1317
Asn Val Ala Val Val Ala Ala Ile Leu Thr Ser Gly Leu Arg Ile Met
        390                 395                 400 cca cac tcg ggt ggt cgt gtt ggc aag ggt att tat ttt gcc tct gag       1365
Pro His Ser Gly Gly Arg Val Gly Lys Gly Ile Tyr Phe Ala Ser Glu
    405                 410                 415 aac agc aag tca gct ggc tat gtt acc acc atg cac tgt ggg ggc cac       1413
Asn Ser Lys Ser Ala Gly Tyr Val Thr Thr Met His Cys Gly Gly His
420                 425                 430 cag gtg ggc tac atg ttc ctg ggc gag gtg gcc ctc ggc aaa gag cac       1461
Gln Val Gly Tyr Met Phe Leu Gly Glu Val Ala Leu Gly Lys Glu His
435                 440                 445                 450 cac atc acc atc gat gac ccc agc ttg aag agt cca ccc cct ggc ttt       1509
His Ile Thr Ile Asp Asp Pro Ser Leu Lys Ser Pro Pro Pro Gly Phe
            455                 460                 465 gac agc gtc atc gcc cga ggc caa acc gag ccg gat ccc gcc cag gac       1557
Asp Ser Val Ile Ala Arg Gly Gln Thr Glu Pro Asp Pro Ala Gln Asp
        470                 475                 480 att gaa ctt gaa ctg gat ggg cag ccg gtg gtg gtg ccc caa ggc ccg       1605
Ile Glu Leu Glu Leu Asp Gly Gln Pro Val Val Val Pro Gln Gly Pro
    485                 490                 495 cct gtg cag tgc ccg tca ttc aaa agc tcc agc ttc agc cag agt gaa       1653
Pro Val Gln Cys Pro Ser Phe Lys Ser Ser Ser Phe Ser Gln Ser Glu
```

```
                500                 505                 510
tac ctc ata tac aag gag agc cag tgt cgc ctg cgc tac ctg ctg gag       1701
Tyr Leu Ile Tyr Lys Glu Ser Gln Cys Arg Leu Arg Tyr Leu Leu Glu
515                 520                 525                 530 att cac ctc taagctgctt gccctcccta ggtccaagcc                          1740
Ile His Leu
```

<210> SEQ ID NO 8
<211> LENGTH: 533
<212> TYPE: PRT
<213> ORGANISM: Mus musculus

<400> SEQUENCE: 8

```
Met Ala Pro Lys Arg Lys Ala Ser Val Gln Thr Glu Gly Ser Lys Lys
1               5                   10                  15

Gln Arg Gln Gly Thr Glu Glu Asp Ser Phe Arg Ser Thr Ala Glu
            20                  25                  30

Ala Leu Arg Ala Ala Pro Ala Asp Asn Arg Val Ile Arg Val Asp Pro
        35                  40                  45

Ser Cys Pro Phe Ser Arg Asn Pro Gly Ile Gln Val His Glu Asp Tyr
    50                  55                  60

Asp Cys Thr Leu Asn Gln Thr Asn Ile Gly Asn Asn Asn Lys Phe
65                  70                  75                  80

Tyr Ile Ile Gln Leu Leu Glu Glu Gly Ser Arg Phe Phe Cys Trp Asn
                85                  90                  95

Arg Trp Gly Arg Val Gly Glu Val Gly Gln Ser Lys Met Asn His Phe
            100                 105                 110

Thr Cys Leu Glu Asp Ala Lys Lys Asp Phe Lys Lys Phe Trp Glu
        115                 120                 125

Lys Thr Lys Asn Lys Trp Glu Glu Arg Asp Arg Phe Val Ala Gln Pro
130                 135                 140

Asn Lys Tyr Thr Leu Ile Glu Val Gln Gly Glu Ala Glu Ser Gln Glu
145                 150                 155                 160

Ala Val Val Lys Ala Leu Ser Pro Gln Val Asp Ser Gly Pro Val Arg
                165                 170                 175

Thr Val Val Lys Pro Cys Ser Leu Asp Pro Ala Thr Gln Asn Leu Ile
            180                 185                 190

Thr Asn Ile Phe Ser Lys Glu Met Phe Lys Asn Ala Met Thr Leu Met
        195                 200                 205

Asn Leu Asp Val Lys Lys Met Pro Leu Gly Lys Leu Thr Lys Gln Gln
    210                 215                 220

Ile Ala Arg Gly Phe Glu Ala Leu Glu Ala Leu Glu Glu Ala Met Lys
225                 230                 235                 240

Asn Pro Thr Gly Asp Gly Gln Ser Leu Glu Glu Leu Ser Ser Cys Phe
                245                 250                 255

Tyr Thr Val Ile Pro His Asn Phe Gly Arg Ser Arg Pro Pro Ile
            260                 265                 270

Asn Ser Pro Asp Val Leu Gln Ala Lys Lys Asp Met Leu Leu Val Leu
        275                 280                 285

Ala Asp Ile Glu Leu Ala Gln Thr Leu Gln Ala Ala Pro Gly Glu Glu
    290                 295                 300

Glu Glu Lys Val Glu Glu Val Pro His Pro Leu Asp Arg Asp Tyr Gln
305                 310                 315                 320

Leu Leu Arg Cys Gln Leu Gln Leu Leu Asp Ser Gly Glu Ser Glu Tyr
                325                 330                 335
```

-continued

```
Lys Ala Ile Gln Thr Tyr Leu Lys Gln Thr Gly Asn Ser Tyr Arg Cys
                340                 345                 350

Pro Asn Leu Arg His Val Trp Lys Val Asn Arg Glu Gly Glu Gly Asp
                355                 360                 365

Arg Phe Gln Ala His Ser Lys Leu Gly Asn Arg Leu Leu Trp His
    370                 375                 380

Gly Thr Asn Val Ala Val Val Ala Ala Ile Leu Thr Ser Gly Leu Arg
385                 390                 395                 400

Ile Met Pro His Ser Gly Arg Val Gly Lys Gly Ile Tyr Phe Ala
                405                 410                 415

Ser Glu Asn Ser Lys Ser Ala Gly Tyr Val Thr Thr Met His Cys Gly
                420                 425                 430

Gly His Gln Val Gly Tyr Met Phe Leu Gly Glu Val Ala Leu Gly Lys
                435                 440                 445

Glu His His Ile Thr Ile Asp Asp Pro Ser Leu Lys Ser Pro Pro Pro
    450                 455                 460

Gly Phe Asp Ser Val Ile Ala Arg Gly Gln Thr Glu Pro Asp Pro Ala
465                 470                 475                 480

Gln Asp Ile Glu Leu Glu Leu Asp Gly Gln Pro Val Val Pro Gln
                485                 490                 495

Gly Pro Pro Val Gln Cys Pro Ser Phe Lys Ser Ser Ser Phe Ser Gln
                500                 505                 510

Ser Glu Tyr Leu Ile Tyr Lys Glu Ser Gln Cys Arg Leu Arg Tyr Leu
                515                 520                 525

Leu Glu Ile His Leu
    530

<210> SEQ ID NO 9
<211> LENGTH: 1587
<212> TYPE: DNA
<213> ORGANISM: Mus musculus
<220> FEATURE:
<221> NAME/KEY: CDS
<222> LOCATION: (1)..(1584)

<400> SEQUENCE: 9 atg gct cca aaa cga aag gcc tct gtg cag act gag ggc tcc aag aag      48
Met Ala Pro Lys Arg Lys Ala Ser Val Gln Thr Glu Gly Ser Lys Lys
1               5                   10                  15 cag cga caa ggg aca gag gag gag gac agc ttc cgg tcc act gcc gag      96
Gln Arg Gln Gly Thr Glu Glu Glu Asp Ser Phe Arg Ser Thr Ala Glu
                20                  25                  30 gct ctc aga gca gca cct gct gat aat cgg gtc atc cgt gtg gac ccc     144
Ala Leu Arg Ala Ala Pro Ala Asp Asn Arg Val Ile Arg Val Asp Pro
            35                  40                  45 tca tgt cca ttc agc cgg aac ccc ggg ata cag gtc cac gag gac tat     192
Ser Cys Pro Phe Ser Arg Asn Pro Gly Ile Gln Val His Glu Asp Tyr
        50                  55                  60 gac tgt acc ctg aac cag acc aac atc ggc aac aac aac aac aag ttc     240
Asp Cys Thr Leu Asn Gln Thr Asn Ile Gly Asn Asn Asn Asn Lys Phe
65                  70                  75                  80 tat att atc caa ctg ctg gag gag ggt agt cgc ttc ttc tgc tgg aat     288
Tyr Ile Ile Gln Leu Leu Glu Glu Gly Ser Arg Phe Phe Cys Trp Asn
                85                  90                  95 cgc tgg ggc cgc gtg gga gag gtg ggc cag agc aag atg aac cac ttc     336
Arg Trp Gly Arg Val Gly Glu Val Gly Gln Ser Lys Met Asn His Phe
                100                 105                 110
```

-continued

| | | |
|---|---|---|
| acc tgc ctg gaa gat gca aag aag gac ttt aag aag aaa ttt tgg gag<br>Thr Cys Leu Glu Asp Ala Lys Lys Asp Phe Lys Lys Lys Phe Trp Glu<br>　　　115　　　　　　　120　　　　　　　125 | | 384 |
| aag act aaa aac aaa tgg gag gag cgg gac cgt ttt gtg gcc cag ccc<br>Lys Thr Lys Asn Lys Trp Glu Glu Arg Asp Arg Phe Val Ala Gln Pro<br>130　　　　　　　135　　　　　　　140 | | 432 |
| aac aag tac aca ctt ata gaa gtc cag gga gaa gca gag agc caa gag<br>Asn Lys Tyr Thr Leu Ile Glu Val Gln Gly Glu Ala Glu Ser Gln Glu<br>145　　　　　　　150　　　　　　　155　　　　　　　160 | | 480 |
| gct gta gtg aag gtg gac agc ggc cct gtg agg acc gtg gtc aag ccc<br>Ala Val Val Lys Val Asp Ser Gly Pro Val Arg Thr Val Val Lys Pro<br>　　　165　　　　　　　170　　　　　　　175 | | 528 |
| tgc tcc cta gac cct gcc acc cag aac ctt atc acc aac atc ttc agc<br>Cys Ser Leu Asp Pro Ala Thr Gln Asn Leu Ile Thr Asn Ile Phe Ser<br>　　　　　180　　　　　　　185　　　　　　　190 | | 576 |
| aaa gag atg ttc aag aac gca atg acc ctc atg aac ctg gat gtg aag<br>Lys Glu Met Phe Lys Asn Ala Met Thr Leu Met Asn Leu Asp Val Lys<br>　　　　　　195　　　　　　　200　　　　　　　205 | | 624 |
| aag atg ccc ttg gga aag ctg acc aag cag cag att gcc cgt ggc ttc<br>Lys Met Pro Leu Gly Lys Leu Thr Lys Gln Gln Ile Ala Arg Gly Phe<br>210　　　　　　　215　　　　　　　220 | | 672 |
| gag gcc ttg gaa gct cta gag gag gcc atg aaa aac ccc aca ggg gat<br>Glu Ala Leu Glu Ala Leu Glu Glu Ala Met Lys Asn Pro Thr Gly Asp<br>225　　　　　　　230　　　　　　　235　　　　　　　240 | | 720 |
| ggc cag agc ctg gaa gag ctc tcc tcc tgc ttc tac act gtc atc cca<br>Gly Gln Ser Leu Glu Glu Leu Ser Ser Cys Phe Tyr Thr Val Ile Pro<br>　　　　　　245　　　　　　　250　　　　　　　255 | | 768 |
| cac aac ttc ggc cgc agc cga ccc ccg ccc atc aac tcc cct gat gtg<br>His Asn Phe Gly Arg Ser Arg Pro Pro Pro Ile Asn Ser Pro Asp Val<br>　　　　260　　　　　　　265　　　　　　　270 | | 816 |
| ctt cag gcc aag aag gac atg ctg ctg gtg cta gcg gac atc gag ttg<br>Leu Gln Ala Lys Lys Asp Met Leu Leu Val Leu Ala Asp Ile Glu Leu<br>　　　275　　　　　　　280　　　　　　　285 | | 864 |
| gcg cag acc ttg cag gca gcc cct ggg gag gag gag gag aaa gtg gaa<br>Ala Gln Thr Leu Gln Ala Ala Pro Gly Glu Glu Glu Glu Lys Val Glu<br>290　　　　　　　295　　　　　　　300 | | 912 |
| gag gtg cca cac cca ctg gat cga gac tac cag ctc ctc agg tgc cag<br>Glu Val Pro His Pro Leu Asp Arg Asp Tyr Gln Leu Leu Arg Cys Gln<br>305　　　　　　　310　　　　　　　315　　　　　　　320 | | 960 |
| ctt caa ctg ctg gac tcc ggg gag tcc gag tac aag gca ata cag acc<br>Leu Gln Leu Leu Asp Ser Gly Glu Ser Glu Tyr Lys Ala Ile Gln Thr<br>　　　　　　325　　　　　　　330　　　　　　　335 | | 1008 |
| tac ctg aaa cag act ggc aac agc tac agg tgc cca aac ctg cgg cat<br>Tyr Leu Lys Gln Thr Gly Asn Ser Tyr Arg Cys Pro Asn Leu Arg His<br>　　　　340　　　　　　　345　　　　　　　350 | | 1056 |
| gtt tgg aaa gtg aac cga gaa ggg gag gga gac agg ttc cag gcc cac<br>Val Trp Lys Val Asn Arg Glu Gly Glu Gly Asp Arg Phe Gln Ala His<br>　　　355　　　　　　　360　　　　　　　365 | | 1104 |
| tcc aaa ctg ggc aat cgg agg ctg ctg tgg cac ggc acc aat gtg gcc<br>Ser Lys Leu Gly Asn Arg Arg Leu Leu Trp His Gly Thr Asn Val Ala<br>370　　　　　　　375　　　　　　　380 | | 1152 |
| gtg gtg gct gcc atc ctc acc agt ggg ctc cga atc atg cca cac tcg<br>Val Val Ala Ala Ile Leu Thr Ser Gly Leu Arg Ile Met Pro His Ser<br>385　　　　　　　390　　　　　　　395　　　　　　　400 | | 1200 |
| ggt ggt cgt gtt ggc aag ggt att tat ttt gcc tct gag aac agc aag<br>Gly Gly Arg Val Gly Lys Gly Ile Tyr Phe Ala Ser Glu Asn Ser Lys<br>　　　　　　405　　　　　　　410　　　　　　　415 | | 1248 |
| tca gct ggc tat gtt acc acc atg cac tgt ggg ggc cac cag gtg ggc<br>Ser Ala Gly Tyr Val Thr Thr Met His Cys Gly Gly His Gln Val Gly<br>　　　　420　　　　　　　425　　　　　　　430 | | 1296 |

```
tac atg ttc ctg ggc gag gtg gcc ctc ggc aaa gag cac cac atc acc      1344
Tyr Met Phe Leu Gly Glu Val Ala Leu Gly Lys Glu His His Ile Thr
        435                 440                 445 atc gat gac ccc agc ttg aag agt cca ccc cct ggc ttt gac agc gtc      1392
Ile Asp Asp Pro Ser Leu Lys Ser Pro Pro Pro Gly Phe Asp Ser Val
450                 455                 460 atc gcc cga ggc caa acc gag ccg gat ccc gcc cag gac att gaa ctt      1440
Ile Ala Arg Gly Gln Thr Glu Pro Asp Pro Ala Gln Asp Ile Glu Leu
465                 470                 475                 480 gaa ctg gat ggg cag ccg gtg gtg gtg ccc caa ggc ccg cct gtg cag      1488
Glu Leu Asp Gly Gln Pro Val Val Val Pro Gln Gly Pro Pro Val Gln
                485                 490                 495 tgc ccg tca ttc aaa agc tcc agc ttc agc cag agt gaa tac ctc ata      1536
Cys Pro Ser Phe Lys Ser Ser Ser Phe Ser Gln Ser Glu Tyr Leu Ile
            500                 505                 510 tac aag gag agc cag tgt cgc ctg cgc tac ctg ctg gag att cac ctc      1584
Tyr Lys Glu Ser Gln Cys Arg Leu Arg Tyr Leu Leu Glu Ile His Leu
        515                 520                 525 taa                                                                   1587
```

<210> SEQ ID NO 10
<211> LENGTH: 528
<212> TYPE: PRT
<213> ORGANISM: Mus musculus

<400> SEQUENCE: 10

```
Met Ala Pro Lys Arg Lys Ala Ser Val Gln Thr Glu Gly Ser Lys Lys
1               5                   10                  15

Gln Arg Gln Gly Thr Glu Glu Asp Ser Phe Arg Ser Thr Ala Glu
            20                  25                  30

Ala Leu Arg Ala Ala Pro Ala Asp Asn Arg Val Ile Arg Val Asp Pro
        35                  40                  45

Ser Cys Pro Phe Ser Arg Asn Pro Gly Ile Gln Val His Glu Asp Tyr
    50                  55                  60

Asp Cys Thr Leu Asn Gln Thr Asn Ile Gly Asn Asn Asn Lys Phe
65                  70                  75                  80

Tyr Ile Ile Gln Leu Leu Glu Glu Gly Ser Arg Phe Phe Cys Trp Asn
                85                  90                  95

Arg Trp Gly Arg Val Gly Glu Val Gly Gln Ser Lys Met Asn His Phe
            100                 105                 110

Thr Cys Leu Glu Asp Ala Lys Lys Asp Phe Lys Lys Phe Trp Glu
        115                 120                 125

Lys Thr Lys Asn Lys Trp Glu Glu Arg Asp Arg Phe Val Ala Gln Pro
    130                 135                 140

Asn Lys Tyr Thr Leu Ile Glu Val Gln Gly Glu Ala Glu Ser Gln Glu
145                 150                 155                 160

Ala Val Val Lys Val Asp Ser Gly Pro Val Arg Thr Val Val Lys Pro
                165                 170                 175

Cys Ser Leu Asp Pro Ala Thr Gln Asn Leu Ile Thr Asn Ile Phe Ser
            180                 185                 190

Lys Glu Met Phe Lys Asn Ala Met Thr Leu Met Asn Leu Asp Val Lys
        195                 200                 205

Lys Met Pro Leu Gly Lys Leu Thr Lys Gln Gln Ile Ala Arg Gly Phe
    210                 215                 220

Glu Ala Leu Glu Ala Leu Glu Glu Ala Met Lys Asn Pro Thr Gly Asp
225                 230                 235                 240
```

```
Gly Gln Ser Leu Glu Glu Leu Ser Ser Cys Phe Tyr Thr Val Ile Pro
                245                 250                 255
His Asn Phe Gly Arg Ser Arg Pro Pro Ile Asn Ser Pro Asp Val
            260                 265                 270
Leu Gln Ala Lys Lys Asp Met Leu Leu Val Leu Ala Asp Ile Glu Leu
        275                 280                 285
Ala Gln Thr Leu Gln Ala Ala Pro Gly Glu Glu Glu Lys Val Glu
    290                 295                 300
Glu Val Pro His Pro Leu Asp Arg Asp Tyr Gln Leu Leu Arg Cys Gln
305                 310                 315                 320
Leu Gln Leu Leu Asp Ser Gly Glu Ser Glu Tyr Lys Ala Ile Gln Thr
                325                 330                 335
Tyr Leu Lys Gln Thr Gly Asn Ser Tyr Arg Cys Pro Asn Leu Arg His
            340                 345                 350
Val Trp Lys Val Asn Arg Glu Gly Glu Gly Asp Arg Phe Gln Ala His
        355                 360                 365
Ser Lys Leu Gly Asn Arg Arg Leu Leu Trp His Gly Thr Asn Val Ala
    370                 375                 380
Val Val Ala Ala Ile Leu Thr Ser Gly Leu Arg Ile Met Pro His Ser
385                 390                 395                 400
Gly Gly Arg Val Gly Lys Gly Ile Tyr Phe Ala Ser Glu Asn Ser Lys
                405                 410                 415
Ser Ala Gly Tyr Val Thr Thr Met His Cys Gly Gly His Gln Val Gly
            420                 425                 430
Tyr Met Phe Leu Gly Glu Val Ala Leu Gly Lys Glu His Ile Thr
        435                 440                 445
Ile Asp Asp Pro Ser Leu Lys Ser Pro Pro Gly Phe Asp Ser Val
    450                 455                 460
Ile Ala Arg Gly Gln Thr Glu Pro Asp Pro Ala Gln Asp Ile Glu Leu
465                 470                 475                 480
Glu Leu Asp Gly Gln Pro Val Val Pro Gln Gly Pro Pro Val Gln
                485                 490                 495
Cys Pro Ser Phe Lys Ser Ser Ser Phe Ser Gln Ser Glu Tyr Leu Ile
            500                 505                 510
Tyr Lys Glu Ser Gln Cys Arg Leu Arg Tyr Leu Leu Glu Ile His Leu
        515                 520                 525

<210> SEQ ID NO 11
<211> LENGTH: 18
<212> TYPE: PRT
<213> ORGANISM: Artificial Sequence
<220> FEATURE:
<223> OTHER INFORMATION: NAD+ binding domain
<220> FEATURE:
<221> NAME/KEY: VARIANT
<222> LOCATION: (2)..(6)
<223> OTHER INFORMATION: any amino acid; residues 3 to 6 may be present
      or absent
<220> FEATURE:
<221> NAME/KEY: VARIANT
<222> LOCATION: (7)..(7)
<223> OTHER INFORMATION: amino acid residue 7 is either Ser or Thr
<220> FEATURE:
<221> NAME/KEY: VARIANT
<222> LOCATION: (9)..(11)
<223> OTHER INFORMATION: any amino acid

<400> SEQUENCE: 11

Pro Xaa Xaa Xaa Xaa Xaa Xaa Gly Xaa Xaa Xaa Gly Lys Gly Ile Tyr
```

```
1               5                  10                 15
Phe Ala

<210> SEQ ID NO 12
<211> LENGTH: 25
<212> TYPE: PRT
<213> ORGANISM: Artificial Sequence
<220> FEATURE:
<223> OTHER INFORMATION: NAD+ binding domain
<220> FEATURE:
<221> NAME/KEY: VARIANT
<222> LOCATION: (1)..(1)
<223> OTHER INFORMATION: amino acid residue 1 is either Ser or Thr
<220> FEATURE:
<221> NAME/KEY: VARIANT
<222> LOCATION: (2)..(2)
<223> OTHER INFORMATION: may be any amino acid
<220> FEATURE:
<221> NAME/KEY: VARIANT
<222> LOCATION: (6)..(6)
<223> OTHER INFORMATION: amino acid residue 6 is either Ile or Val
<220> FEATURE:
<221> NAME/KEY: VARIANT
<222> LOCATION: (7)..(7)
<223> OTHER INFORMATION: may be any amino acid
<220> FEATURE:
<221> NAME/KEY: VARIANT
<222> LOCATION: (9)..(13)
<223> OTHER INFORMATION: may be any amino acid; 10-13 may be present or
      absent
<220> FEATURE:
<221> NAME/KEY: VARIANT
<222> LOCATION: (14)..(14)
<223> OTHER INFORMATION: amino acid residue 14 is either Ser or Thr
<220> FEATURE:
<221> NAME/KEY: VARIANT
<222> LOCATION: (16)..(18)
<223> OTHER INFORMATION: may be any amino acid

<400> SEQUENCE: 12

Xaa Xaa Gly Leu Arg Xaa Xaa Pro Xaa Xaa Xaa Xaa Xaa Gly Xaa
1               5                  10                 15

Xaa Xaa Gly Lys Gly Ile Tyr Phe Ala
            20                  25

<210> SEQ ID NO 13
<211> LENGTH: 49
<212> TYPE: PRT
<213> ORGANISM: Artificial Sequence
<220> FEATURE:
<223> OTHER INFORMATION: NAD+ binding domain
<220> FEATURE:
<221> NAME/KEY: VARIANT
<222> LOCATION: (6)..(6)
<223> OTHER INFORMATION: Ser or Thr
<220> FEATURE:
<221> NAME/KEY: VARIANT
<222> LOCATION: (7)..(13)
<223> OTHER INFORMATION: may be any amino acid
<220> FEATURE:
<221> NAME/KEY: VARIANT
<222> LOCATION: (16)..(16)
<223> OTHER INFORMATION: Ser or Thr
<220> FEATURE:
<221> NAME/KEY: VARIANT
<222> LOCATION: (17)..(17)
<223> OTHER INFORMATION: may be any amino acid
<220> FEATURE:
<221> NAME/KEY: VARIANT
<222> LOCATION: (21)..(21)
<223> OTHER INFORMATION: Ile or Val
<220> FEATURE:
<221> NAME/KEY: VARIANT
<222> LOCATION: (22)..(22)
```

```
<223> OTHER INFORMATION: may be any amino acid
<220> FEATURE:
<221> NAME/KEY: VARIANT
<222> LOCATION: (24)..(28)
<223> OTHER INFORMATION: may be any amino acid; residues 25-28 may be
      present or absent
<220> FEATURE:
<221> NAME/KEY: VARIANT
<222> LOCATION: (29)..(29)
<223> OTHER INFORMATION: Ser or Thr
<220> FEATURE:
<221> NAME/KEY: VARIANT
<222> LOCATION: (31)..(33)
<223> OTHER INFORMATION: may be any amino acid
<220> FEATURE:
<221> NAME/KEY: VARIANT
<222> LOCATION: (41)..(43)
<223> OTHER INFORMATION: may be any amino acid
<220> FEATURE:
<221> NAME/KEY: VARIANT
<222> LOCATION: (48)..(48)
<223> OTHER INFORMATION: may be any amino acid

<400> SEQUENCE: 13

Leu Leu Trp His Gly Xaa Xaa Xaa Xaa Xaa Xaa Xaa Ile Leu Xaa
1               5                   10                  15

Xaa Gly Leu Arg Xaa Xaa Pro Xaa Xaa Xaa Xaa Xaa Gly Xaa Xaa
            20                  25                  30

Xaa Gly Lys Gly Ile Tyr Phe Ala Xaa Xaa Xaa Ser Lys Ser Ala Xaa
        35                  40                  45

Tyr

<210> SEQ ID NO 14
<211> LENGTH: 22
<212> TYPE: PRT
<213> ORGANISM: Artificial Sequence
<220> FEATURE:
<223> OTHER INFORMATION: leucine zipper motif
<220> FEATURE:
<221> NAME/KEY: VARIANT
<222> LOCATION: (1)..(1)
<223> OTHER INFORMATION: Leu or Val
<220> FEATURE:
<221> NAME/KEY: VARIANT
<222> LOCATION: (2)..(7)
<223> OTHER INFORMATION: may be any amino acid
<220> FEATURE:
<221> NAME/KEY: VARIANT
<222> LOCATION: (9)..(14)
<223> OTHER INFORMATION: may be any amino acid
<220> FEATURE:
<221> NAME/KEY: VARIANT
<222> LOCATION: (16)..(21)
<223> OTHER INFORMATION: may be any amino acid

<400> SEQUENCE: 14

Xaa Xaa Xaa Xaa Xaa Xaa Xaa Leu Xaa Xaa Xaa Xaa Xaa Xaa Leu Xaa
1               5                   10                  15

Xaa Xaa Xaa Xaa Xaa Leu
            20

<210> SEQ ID NO 15
<211> LENGTH: 37
<212> TYPE: PRT
<213> ORGANISM: Artificial Sequence
<220> FEATURE:
<223> OTHER INFORMATION: part-sequence motif 1
<220> FEATURE:
<221> NAME/KEY: VARIANT
<222> LOCATION: (2)..(10)
<223> OTHER INFORMATION: may be any amino acid
```

```
<220> FEATURE:
<221> NAME/KEY: VARIANT
<222> LOCATION: (12)..(13)
<223> OTHER INFORMATION: may be any amino acid
<220> FEATURE:
<221> NAME/KEY: VARIANT
<222> LOCATION: (15)..(16)
<223> OTHER INFORMATION: may be any amino acid
<220> FEATURE:
<221> NAME/KEY: VARIANT
<222> LOCATION: (20)..(20)
<223> OTHER INFORMATION: may be any amino acid
<220> FEATURE:
<221> NAME/KEY: VARIANT
<222> LOCATION: (21)..(21)
<223> OTHER INFORMATION: Asp or Glu
<220> FEATURE:
<221> NAME/KEY: VARIANT
<222> LOCATION: (22)..(32)
<223> OTHER INFORMATION: may be any amino acid; residue 32 may be
      present or absent

<400> SEQUENCE: 15

Leu Xaa Xaa Xaa Xaa Xaa Xaa Xaa Xaa Asn Xaa Xaa Tyr Xaa Xaa
1               5                   10                  15

Gln Leu Leu Xaa Xaa Xaa Xaa Xaa Xaa Xaa Xaa Xaa Xaa Xaa
            20                  25                  30

Trp Gly Arg Val Gly
        35

<210> SEQ ID NO 16
<211> LENGTH: 29
<212> TYPE: PRT
<213> ORGANISM: Artificial Sequence
<220> FEATURE:
<223> OTHER INFORMATION: part-sequence motif 2
<220> FEATURE:
<221> NAME/KEY: VARIANT
<222> LOCATION: (2)..(4)
<223> OTHER INFORMATION: may be any amino acid
<220> FEATURE:
<221> NAME/KEY: VARIANT
<222> LOCATION: (6)..(6)
<223> OTHER INFORMATION: may be any amino acid
<220> FEATURE:
<221> NAME/KEY: VARIANT
<222> LOCATION: (8)..(11)
<223> OTHER INFORMATION: may be any amino acid
<220> FEATURE:
<221> NAME/KEY: VARIANT
<222> LOCATION: (14)..(14)
<223> OTHER INFORMATION: may be any amino acid
<220> FEATURE:
<221> NAME/KEY: VARIANT
<222> LOCATION: (16)..(16)
<223> OTHER INFORMATION: may be any amino acid
<220> FEATURE:
<221> NAME/KEY: VARIANT
<222> LOCATION: (18)..(22)
<223> OTHER INFORMATION: may be any amino acid
<220> FEATURE:
<221> NAME/KEY: VARIANT
<222> LOCATION: (24)..(26)
<223> OTHER INFORMATION: may be any amino acid
<220> FEATURE:
<221> NAME/KEY: VARIANT
<222> LOCATION: (28)..(28)
<223> OTHER INFORMATION: may be any amino acid

<400> SEQUENCE: 16

Ala Xaa Xaa Xaa Phe Xaa Lys Xaa Xaa Xaa Xaa Lys Thr Xaa Asn Xaa
1               5                   10                  15

Trp Xaa Xaa Xaa Xaa Xaa Phe Xaa Xaa Xaa Pro Xaa Lys
```

```
<210> SEQ ID NO 17
<211> LENGTH: 44
<212> TYPE: PRT
<213> ORGANISM: Artificial Sequence
<220> FEATURE:
<223> OTHER INFORMATION: part-sequence motif 3
<220> FEATURE:
<221> NAME/KEY: VARIANT
<222> LOCATION: (2)..(2)
<223> OTHER INFORMATION: may be any amino acid
<220> FEATURE:
<221> NAME/KEY: VARIANT
<222> LOCATION: (4)..(4)
<223> OTHER INFORMATION: Ile or Leu
<220> FEATURE:
<221> NAME/KEY: VARIANT
<222> LOCATION: (5)..(6)
<223> OTHER INFORMATION: may be any amino acid
<220> FEATURE:
<221> NAME/KEY: VARIANT
<222> LOCATION: (8)..(16)
<223> OTHER INFORMATION: may be any amino acid
<220> FEATURE:
<221> NAME/KEY: VARIANT
<222> LOCATION: (18)..(27)
<223> OTHER INFORMATION: may be any amino acid
<220> FEATURE:
<221> NAME/KEY: VARIANT
<222> LOCATION: (33)..(35)
<223> OTHER INFORMATION: may be any amino acid
<220> FEATURE:
<221> NAME/KEY: VARIANT
<222> LOCATION: (38)..(43)
<223> OTHER INFORMATION: may be any amino acid

<400> SEQUENCE: 17

Gln Xaa Leu Xaa Xaa Xaa Ile Xaa Xaa Xaa Xaa Xaa Xaa Xaa Xaa
1               5                   10                  15

Met Xaa Xaa Xaa Xaa Xaa Xaa Xaa Xaa Xaa Xaa Pro Leu Gly Lys Leu
            20                  25                  30

Xaa Xaa Xaa Gln Ile Xaa Xaa Xaa Xaa Xaa Xaa Leu
        35                  40

<210> SEQ ID NO 18
<211> LENGTH: 15
<212> TYPE: PRT
<213> ORGANISM: Artificial Sequence
<220> FEATURE:
<223> OTHER INFORMATION: part-sequence motif 4
<220> FEATURE:
<221> NAME/KEY: VARIANT
<222> LOCATION: (4)..(4)
<223> OTHER INFORMATION: may be any amino acid
<220> FEATURE:
<221> NAME/KEY: VARIANT
<222> LOCATION: (8)..(8)
<223> OTHER INFORMATION: may be any amino acid
<220> FEATURE:
<221> NAME/KEY: VARIANT
<222> LOCATION: (11)..(13)
<223> OTHER INFORMATION: may be any amino acid

<400> SEQUENCE: 18

Phe Tyr Thr Xaa Ile Pro His Xaa Phe Gly Xaa Xaa Xaa Pro Pro
1               5                   10                  15

<210> SEQ ID NO 19
<211> LENGTH: 17
<212> TYPE: PRT
<213> ORGANISM: Artificial Sequence
```

```
<220> FEATURE:
<223> OTHER INFORMATION: part-sequence motif 5
<220> FEATURE:
<221> NAME/KEY: VARIANT
<222> LOCATION: (2)..(4)
<223> OTHER INFORMATION: may be any amino acid
<220> FEATURE:
<221> NAME/KEY: VARIANT
<222> LOCATION: (6)..(7)
<223> OTHER INFORMATION: may be any amino acid
<220> FEATURE:
<221> NAME/KEY: VARIANT
<222> LOCATION: (9)..(9)
<223> OTHER INFORMATION: may be any amino acid
<220> FEATURE:
<221> NAME/KEY: VARIANT
<222> LOCATION: (13)..(13)
<223> OTHER INFORMATION: may be any amino acid
<220> FEATURE:
<221> NAME/KEY: VARIANT
<222> LOCATION: (15)..(16)
<223> OTHER INFORMATION: may be any amino acid

<400> SEQUENCE: 19

Lys Xaa Xaa Xaa Leu Xaa Xaa Leu Xaa Asp Ile Glu Xaa Ala Xaa Xaa
1               5                   10                  15

Leu

<210> SEQ ID NO 20
<211> LENGTH: 11
<212> TYPE: PRT
<213> ORGANISM: Artificial Sequence
<220> FEATURE:
<223> OTHER INFORMATION: part-sequence motif 6
<220> FEATURE:
<221> NAME/KEY: VARIANT
<222> LOCATION: (2)..(4)
<223> OTHER INFORMATION: may be any amino acid
<220> FEATURE:
<221> NAME/KEY: VARIANT
<222> LOCATION: (6)..(6)
<223> OTHER INFORMATION: may be any amino acid

<400> SEQUENCE: 20

Gly Xaa Xaa Xaa Leu Xaa Glu Val Ala Leu Gly
1               5                   10

<210> SEQ ID NO 21
<211> LENGTH: 28
<212> TYPE: PRT
<213> ORGANISM: Artificial Sequence
<220> FEATURE:
<223> OTHER INFORMATION: part-sequence motif 7
<220> FEATURE:
<221> NAME/KEY: VARIANT
<222> LOCATION: (2)..(3)
<223> OTHER INFORMATION: may be any amino acid
<220> FEATURE:
<221> NAME/KEY: VARIANT
<222> LOCATION: (5)..(8)
<223> OTHER INFORMATION: may be any amino acid
<220> FEATURE:
<221> NAME/KEY: VARIANT
<222> LOCATION: (10)..(12)
<223> OTHER INFORMATION: may be any amino acid
<220> FEATURE:
<221> NAME/KEY: VARIANT
<222> LOCATION: (14)..(22)
<223> OTHER INFORMATION: may be any amino acid; residues 21 and 22 may
      be present or absent
<220> FEATURE:
<221> NAME/KEY: VARIANT
<222> LOCATION: (24)..(24)
<223> OTHER INFORMATION: may be any amino acid
```

```
<220> FEATURE:
<221> NAME/KEY: VARIANT
<222> LOCATION: (26)..(27)
<223> OTHER INFORMATION: may be any amino acid

<400> SEQUENCE: 21

Gly Xaa Xaa Ser Xaa Xaa Xaa Gly Xaa Xaa Xaa Pro Xaa Xaa Xaa
1               5                   10                  15

Xaa Xaa Xaa Xaa Xaa Xaa Leu Xaa Gly Xaa Xaa Val
            20                  25

<210> SEQ ID NO 22
<211> LENGTH: 16
<212> TYPE: PRT
<213> ORGANISM: Artificial Sequence
<220> FEATURE:
<223> OTHER INFORMATION: part-sequence motif 8
<220> FEATURE:
<221> NAME/KEY: VARIANT
<222> LOCATION: (2)..(2)
<223> OTHER INFORMATION: Tyr or Phe
<220> FEATURE:
<221> NAME/KEY: VARIANT
<222> LOCATION: (3)..(4)
<223> OTHER INFORMATION: may be any amino acid
<220> FEATURE:
<221> NAME/KEY: VARIANT
<222> LOCATION: (6)..(8)
<223> OTHER INFORMATION: may be any amino acid
<220> FEATURE:
<221> NAME/KEY: VARIANT
<222> LOCATION: (10)..(13)
<223> OTHER INFORMATION: may be any amino acid

<400> SEQUENCE: 22

Glu Xaa Xaa Xaa Tyr Xaa Xaa Xaa Gln Xaa Xaa Xaa Xaa Tyr Leu Leu
1               5                   10                  15

<210> SEQ ID NO 23
<211> LENGTH: 20
<212> TYPE: PRT
<213> ORGANISM: Artificial Sequence
<220> FEATURE:
<223> OTHER INFORMATION: synthetic sequence for antibody production

<400> SEQUENCE: 23

Met Ala Ala Arg Arg Arg Arg Ser Thr Gly Gly Gly Arg Ala Arg Ala
1               5                   10                  15

Leu Asn Glu Ser
            20

<210> SEQ ID NO 24
<211> LENGTH: 20
<212> TYPE: PRT
<213> ORGANISM: Artificial Sequence
<220> FEATURE:
<223> OTHER INFORMATION: synthetic sequence for antibody production

<400> SEQUENCE: 24

Lys Thr Glu Leu Gln Ser Pro Glu His Pro Leu Asp Gln His Tyr Arg
1               5                   10                  15

Asn Leu His Cys
            20

<210> SEQ ID NO 25
<211> LENGTH: 21
<212> TYPE: PRT
<213> ORGANISM: Artificial Sequence
```

```
<220> FEATURE:
<223> OTHER INFORMATION: synthetic sequence for antibody production

<400> SEQUENCE: 25

Cys Lys Gly Arg Gln Ala Gly Arg Glu Glu Asp Pro Phe Arg Ser Thr
1               5                   10                  15
Ala Glu Ala Leu Lys
            20

<210> SEQ ID NO 26
<211> LENGTH: 20
<212> TYPE: PRT
<213> ORGANISM: Artificial Sequence
<220> FEATURE:
<223> OTHER INFORMATION: synthetic sequence for antibody production

<400> SEQUENCE: 26

Cys Lys Gln Gln Ile Ala Arg Gly Phe Glu Ala Leu Glu Ala Leu Glu
1               5                   10                  15
Glu Ala Leu Lys
            20

<210> SEQ ID NO 27
<211> LENGTH: 19
<212> TYPE: PRT
<213> ORGANISM: Artificial Sequence
<220> FEATURE:
<223> OTHER INFORMATION: synthetic sequence for antibody production

<400> SEQUENCE: 27

Lys Gln Gln Ile Ala Arg Gly Phe Glu Ala Leu Glu Ala Leu Glu Glu
1               5                   10                  15
Ala Leu Lys

<210> SEQ ID NO 28
<211> LENGTH: 19
<212> TYPE: PRT
<213> ORGANISM: Mus musculus

<400> SEQUENCE: 28

Lys Gln Gln Ile Ala Arg Gly Phe Glu Ala Leu Glu Ala Leu Glu Glu
1               5                   10                  15
Ala Met Lys

<210> SEQ ID NO 29
<211> LENGTH: 7
<212> TYPE: PRT
<213> ORGANISM: Artificial Sequence
<220> FEATURE:
<223> OTHER INFORMATION: NAD+ binding domain
<220> FEATURE:
<221> NAME/KEY: VARIANT
<222> LOCATION: (2)..(4)
<223> OTHER INFORMATION: may be any amino acid residue

<400> SEQUENCE: 29

Gly Xaa Xaa Xaa Gly Lys Gly
1               5

<210> SEQ ID NO 30
<211> LENGTH: 38
<212> TYPE: PRT
<213> ORGANISM: Artificial Sequence
<220> FEATURE:
<223> OTHER INFORMATION: PARP zinc finger sequence motif
```

-continued

```
<220> FEATURE:
<221> NAME/KEY: VARIANT
<222> LOCATION: (2)..(3)
<223> OTHER INFORMATION: may be any amino acid
<220> FEATURE:
<221> NAME/KEY: VARIANT
<222> LOCATION: (5)..(34)
<223> OTHER INFORMATION: may be any amino acid; residues 33 and 34 may
      be present or absent
<220> FEATURE:
<221> NAME/KEY: VARIANT
<222> LOCATION: (36)..(37)
<223> OTHER INFORMATION: may be any amino acid

<400> SEQUENCE: 30

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa His Xaa Xaa Cys
        35

<210> SEQ ID NO 31
<211> LENGTH: 10
<212> TYPE: PRT
<213> ORGANISM: Arabidopsis thaliana

<400> SEQUENCE: 31

Ala Ala Val Leu Asp Gln Trp Ile Pro Asp
1               5                   10

<210> SEQ ID NO 32
<211> LENGTH: 39
<212> TYPE: DNA
<213> ORGANISM: Homo sapiens
<220> FEATURE:
<221> NAME/KEY: CDS
<222> LOCATION: (1)..(39)

<400> SEQUENCE: 32 gta tgc cag gaa ggt cat ggg cca gca aaa ggg tct ctg          39
Gly Met Pro Gly Arg Ser Trp Ala Ser Lys Arg Val Ser
1               5                   10

<210> SEQ ID NO 33
<211> LENGTH: 13
<212> TYPE: PRT
<213> ORGANISM: Homo sapiens

<400> SEQUENCE: 33

Gly Met Pro Gly Arg Ser Trp Ala Ser Lys Arg Val Ser
1               5                   10

<210> SEQ ID NO 34
<211> LENGTH: 577
<212> TYPE: PRT
<213> ORGANISM: Artificial Sequence
<220> FEATURE:
<223> OTHER INFORMATION: sequence is hypothetical majority consensus
      sequence
<220> FEATURE:
<221> NAME/KEY: VARIANT
<222> LOCATION: (36)..(36)
<223> OTHER INFORMATION: may be any amino acid residue
<220> FEATURE:
<221> NAME/KEY: VARIANT
<222> LOCATION: (48)..(48)
<223> OTHER INFORMATION: may be any amino acid residue
<220> FEATURE:
```

```
<221> NAME/KEY: VARIANT
<222> LOCATION: (51)..(53)
<223> OTHER INFORMATION: may be any amino acid residue
<220> FEATURE:
<221> NAME/KEY: VARIANT
<222> LOCATION: (57)..(57)
<223> OTHER INFORMATION: may be any amino acid residue
<220> FEATURE:
<221> NAME/KEY: VARIANT
<222> LOCATION: (68)..(68)
<223> OTHER INFORMATION: may be any amino acid residue
<220> FEATURE:
<221> NAME/KEY: VARIANT
<222> LOCATION: (72)..(72)
<223> OTHER INFORMATION: may be any amino acid residue
<220> FEATURE:
<221> NAME/KEY: VARIANT
<222> LOCATION: (74)..(74)
<223> OTHER INFORMATION: may be any amino acid residue
<220> FEATURE:
<221> NAME/KEY: VARIANT
<222> LOCATION: (80)..(80)
<223> OTHER INFORMATION: may be any amino acid residue
<220> FEATURE:
<221> NAME/KEY: VARIANT
<222> LOCATION: (85)..(85)
<223> OTHER INFORMATION: may be any amino acid residue
<220> FEATURE:
<221> NAME/KEY: VARIANT
<222> LOCATION: (89)..(89)
<223> OTHER INFORMATION: may be any amino acid residue
<220> FEATURE:
<221> NAME/KEY: VARIANT
<222> LOCATION: (92)..(92)
<223> OTHER INFORMATION: may be any amino acid residue
<220> FEATURE:
<221> NAME/KEY: VARIANT
<222> LOCATION: (106)..(106)
<223> OTHER INFORMATION: may be any amino acid residue
<220> FEATURE:
<221> NAME/KEY: VARIANT
<222> LOCATION: (122)..(122)
<223> OTHER INFORMATION: may be any amino acid residue
<220> FEATURE:
<221> NAME/KEY: VARIANT
<222> LOCATION: (126)..(126)
<223> OTHER INFORMATION: may be any amino acid residue
<220> FEATURE:
<221> NAME/KEY: VARIANT
<222> LOCATION: (147)..(147)
<223> OTHER INFORMATION: may be any amino acid residue
<220> FEATURE:
<221> NAME/KEY: VARIANT
<222> LOCATION: (156)..(156)
<223> OTHER INFORMATION: may be any amino acid residue
<220> FEATURE:
<221> NAME/KEY: VARIANT
<222> LOCATION: (160)..(160)
<223> OTHER INFORMATION: may be any amino acid residue
<220> FEATURE:
<221> NAME/KEY: VARIANT
<222> LOCATION: (173)..(173)
<223> OTHER INFORMATION: may be any amino acid residue
<220> FEATURE:
<221> NAME/KEY: VARIANT
<222> LOCATION: (177)..(177)
<223> OTHER INFORMATION: may be any amino acid residue
<220> FEATURE:
<221> NAME/KEY: VARIANT
<222> LOCATION: (189)..(189)
<223> OTHER INFORMATION: may be any amino acid residue
<220> FEATURE:
<221> NAME/KEY: VARIANT
<222> LOCATION: (191)..(191)
<223> OTHER INFORMATION: may be any amino acid residue
<220> FEATURE:
<221> NAME/KEY: VARIANT
<222> LOCATION: (202)..(202)
<223> OTHER INFORMATION: may be any amino acid residue
```

```
<220> FEATURE:
<221> NAME/KEY: VARIANT
<222> LOCATION: (205)..(205)
<223> OTHER INFORMATION: may be any amino acid residue
<220> FEATURE:
<221> NAME/KEY: VARIANT
<222> LOCATION: (212)..(212)
<223> OTHER INFORMATION: may be any amino acid residue
<220> FEATURE:
<221> NAME/KEY: VARIANT
<222> LOCATION: (226)..(226)
<223> OTHER INFORMATION: may be any amino acid residue
<220> FEATURE:
<221> NAME/KEY: VARIANT
<222> LOCATION: (242)..(242)
<223> OTHER INFORMATION: may be any amino acid residue
<220> FEATURE:
<221> NAME/KEY: VARIANT
<222> LOCATION: (245)..(245)
<223> OTHER INFORMATION: may be any amino acid residue
<220> FEATURE:
<221> NAME/KEY: VARIANT
<222> LOCATION: (275)..(275)
<223> OTHER INFORMATION: may be any amino acid residue
<220> FEATURE:
<221> NAME/KEY: VARIANT
<222> LOCATION: (277)..(277)
<223> OTHER INFORMATION: may be any amino acid residue
<220> FEATURE:
<221> NAME/KEY: VARIANT
<222> LOCATION: (280)..(280)
<223> OTHER INFORMATION: may be any amino acid residue
<220> FEATURE:
<221> NAME/KEY: VARIANT
<222> LOCATION: (291)..(291)
<223> OTHER INFORMATION: may be any amino acid residue
<220> FEATURE:
<221> NAME/KEY: VARIANT
<222> LOCATION: (302)..(302)
<223> OTHER INFORMATION: may be any amino acid residue
<220> FEATURE:
<221> NAME/KEY: VARIANT
<222> LOCATION: (304)..(304)
<223> OTHER INFORMATION: may be any amino acid residue
<220> FEATURE:
<221> NAME/KEY: VARIANT
<222> LOCATION: (313)..(313)
<223> OTHER INFORMATION: may be any amino acid residue
<220> FEATURE:
<221> NAME/KEY: VARIANT
<222> LOCATION: (332)..(332)
<223> OTHER INFORMATION: may be any amino acid residue
<220> FEATURE:
<221> NAME/KEY: VARIANT
<222> LOCATION: (336)..(338)
<223> OTHER INFORMATION: may be any amino acid residue
<220> FEATURE:
<221> NAME/KEY: VARIANT
<222> LOCATION: (340)..(340)
<223> OTHER INFORMATION: may be any amino acid residue
<220> FEATURE:
<221> NAME/KEY: VARIANT
<222> LOCATION: (342)..(342)
<223> OTHER INFORMATION: may be any amino acid residue
<220> FEATURE:
<221> NAME/KEY: VARIANT
<222> LOCATION: (370)..(370)
<223> OTHER INFORMATION: may be any amino acid residue
<220> FEATURE:
<221> NAME/KEY: VARIANT
<222> LOCATION: (385)..(385)
<223> OTHER INFORMATION: may be any amino acid residue
<220> FEATURE:
<221> NAME/KEY: VARIANT
<222> LOCATION: (393)..(393)
<223> OTHER INFORMATION: may be any amino acid residue
<220> FEATURE:
<221> NAME/KEY: VARIANT
<222> LOCATION: (404)..(404)
```

```
<223> OTHER INFORMATION: may be any amino acid residue
<220> FEATURE:
<221> NAME/KEY: VARIANT
<222> LOCATION: (467)..(467)
<223> OTHER INFORMATION: may be any amino acid residue
<220> FEATURE:
<221> NAME/KEY: VARIANT
<222> LOCATION: (470)..(470)
<223> OTHER INFORMATION: may be any amino acid residue
<220> FEATURE:
<221> NAME/KEY: VARIANT
<222> LOCATION: (475)..(475)
<223> OTHER INFORMATION: may be any amino acid residue
<220> FEATURE:
<221> NAME/KEY: VARIANT
<222> LOCATION: (492)..(492)
<223> OTHER INFORMATION: may be any amino acid residue
<220> FEATURE:
<221> NAME/KEY: VARIANT
<222> LOCATION: (493)..(493)
<223> OTHER INFORMATION: may be any amino acid residue
<220> FEATURE:
<221> NAME/KEY: VARIANT
<222> LOCATION: (540)..(540)
<223> OTHER INFORMATION: may be any amino acid residue
<220> FEATURE:
<221> NAME/KEY: VARIANT
<222> LOCATION: (543)..(543)
<223> OTHER INFORMATION: may be any amino acid residue
<220> FEATURE:
<221> NAME/KEY: VARIANT
<222> LOCATION: (545)..(545)
<223> OTHER INFORMATION: may be any amino acid residue
<220> FEATURE:
<221> NAME/KEY: VARIANT
<222> LOCATION: (558)..(558)
<223> OTHER INFORMATION: may be any amino acid residue
<220> FEATURE:
<221> NAME/KEY: VARIANT
<222> LOCATION: (575)..(575)
<223> OTHER INFORMATION: may be any amino acid residue

<400> SEQUENCE: 34

Met Ala Gly Gly Leu Arg Pro Glu Arg Cys Glu Lys Gly Lys Arg Asp
1               5                   10                  15

Lys Asp Lys Leu Leu Lys Val Phe Ala Glu Cys Tyr Cys Gly Ala Pro
            20                  25                  30

Lys Arg Lys Xaa Trp Val Gln Thr Glu Gly Ser Glu Lys Lys Lys Xaa
        35                  40                  45

Arg Gln Xaa Xaa Xaa Glu Glu Asp Xaa Phe Arg Ser Thr Ala Glu Ala
    50                  55                  60

Leu Lys Ala Xaa Pro Ala Glu Xaa Arg Xaa Ile Arg Val Asp Pro Xaa
65                  70                  75                  80

Cys Pro Leu Ser Xaa Asn Pro Gly Xaa Gln Val Xaa Glu Asp Val Tyr
                85                  90                  95

Asp Cys Thr Leu Asn Gln Thr Asn Ile Xaa Asn Asn Asn Lys Phe
            100                 105                 110

Tyr Ile Ile Gln Leu Leu Glu Asp Asp Xaa Arg Phe Phe Xaa Cys Trp
        115                 120                 125

Asn Arg Trp Gly Arg Val Gly Glu Val Gly Gln Ser Lys Leu Asn His
    130                 135                 140

Phe Thr Xaa Leu Glu Asp Ala Lys Glu Asp Phe Xaa Lys Phe Xaa
145                 150                 155                 160

Glu Lys Glu Thr Lys Asn Asn Trp Glu Arg Asp Xaa Phe Val Lys
                165                 170                 175

Xaa Pro Gly Lys Tyr Thr Leu Leu Glu Val Asp Tyr Xaa Glu Xaa Glu
            180                 185                 190
```

Asp Glu Glu Ala Val Val Lys Ser Leu Xaa Val Asp Xaa Gly Pro Val
            195                 200                 205

Ser Thr Val Xaa Lys Arg Val Gln Pro Cys Ser Leu Asp Pro Ala Thr
210                 215                 220

Gln Xaa Leu Ile Thr Asn Ile Phe Ser Val Glu Met Phe Lys Asn Ala
225                 230                 235                 240

Met Xaa Leu Met Xaa Leu Asp Val Lys Lys Met Pro Leu Gly Lys Leu
            245                 250                 255

Ser Lys Gln Gln Ile Ala Ala Gly Phe Glu Ala Leu Glu Ala Leu Glu
            260                 265                 270

Glu Ala Xaa Lys Xaa Gly Thr Xaa Gly Gly Gln Ser Leu Glu Glu Leu
            275                 280                 285

Ser Ser Xaa Phe Tyr Thr Val Ile Pro His Asp Phe Gly Xaa Ser Xaa
            290                 295                 300

Pro Pro Leu Ile Asn Ser Pro Asp Xaa Leu Gln Ala Lys Lys Asp Met
305                 310                 315                 320

Leu Leu Val Leu Ala Asp Ile Glu Leu Ala Gln Xaa Leu Gln Ala Xaa
            325                 330                 335

Xaa Xaa Glu Xaa Ser Xaa Lys Val Glu Glu Val Pro His Pro Leu Asp
            340                 345                 350

Arg Asp Tyr Gln Leu Leu Lys Cys Gln Leu Gln Leu Leu Asp Ser Gly
            355                 360                 365

Ser Xaa Glu Tyr Lys Val Ile Gln Thr Tyr Leu Lys Gln Thr Gly Ala
            370                 375                 380

Xaa Thr His Cys Pro Tyr Thr Leu Xaa Asp Ile Phe Lys Val Glu Arg
385                 390                 395                 400

Glu Gly Glu Xaa Asp Arg Phe Gln Ala His Ser Lys Leu Gly Asn Arg
            405                 410                 415

Arg Leu Leu Trp His Gly Ser Asn Met Ala Val Val Ala Gly Ile Leu
            420                 425                 430

Ser Ser Gly Leu Arg Ile Ala Pro His Glu Ala Pro Ser Gly Gly Arg
            435                 440                 445

Val Gly Lys Gly Ile Tyr Phe Ala Ser Glu Asn Ser Lys Ser Ala Gly
            450                 455                 460

Tyr Val Xaa Thr Ser Xaa Cys Gly Gly His Xaa Val Gly Leu Met Leu
465                 470                 475                 480

Leu Gly Glu Val Ala Leu Gly Glu His Glu Leu Xaa Xaa Ala Asn Pro
            485                 490                 495

Ser Leu Lys Ser Leu Pro Pro Gly Lys Asp Ser Val Ile Gly Leu Gly
            500                 505                 510

Lys Thr Glu Pro Asp Pro Ala Gln Asp Ile Glu Leu Glu Leu Asp Gly
            515                 520                 525

Gln Gly Val Val Pro Leu Gly Pro Pro Val Xaa Cys Gly Xaa Phe
            530                 535                 540

Xaa Ser Ser Phe Ser Leu Tyr Ser Glu Tyr Leu Val Tyr Xaa Glu Ser
545                 550                 555                 560

Gln Val Arg Leu Arg Tyr Leu Leu Glu Val His Phe Asn Phe Xaa Leu
            565                 570                 575

Trp

<210> SEQ ID NO 35
<211> LENGTH: 1014
<212> TYPE: PRT

-continued

<213> ORGANISM: Homo sapiens

<400> SEQUENCE: 35

Met Ala Glu Ser Ser Asp Lys Leu Tyr Arg Val Glu Tyr Ala Lys Ser
1               5                   10                  15

Glu Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Lys Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
    370                 375                 380

Ser Ala Asp Lys Pro Leu Ser Asn Met Lys Ile Leu Thr Leu Gly Lys
385                 390                 395                 400

```
Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Met Glu Glu Val Lys Glu
        435                 440                 445

Ala Asn Ile Arg Val Val Ser Glu Asp Phe Leu Gln Asp Tyr Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Ala Pro Arg
                485                 490                 495

Gly Lys Ser Gly Ala Ala Leu Ser Lys Lys Ser Lys Gly Gln Val Lys
            500                 505                 510

Glu Gly Ile Asn Lys Ser Glu Lys Arg Met Lys Leu Thr Leu Lys
        515                 520                 525

Gly Gly Ala Ala Val Asp Pro Asp Ser Gly Leu Glu His Ser Ala His
    530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu His Pro Met Lys Leu Tyr Glu Glu Lys Thr Gly Asn
    610                 615                 620

Ala Trp His Ser Lys Asn Phe Thr Lys Tyr Pro Lys Lys Pro Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Pro Asp Val Glu Ser Met Lys Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
    770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Asn Ala Tyr Asp Leu Glu
```

```
                820                 825                 830
Val Ile Asp Ile Phe Lys Ile Glu Arg Glu Gly Glu Cys Gln Arg Tyr
            835                 840                 845

Lys Pro Pro Lys Gln Leu His Asn Arg Arg Leu Leu Trp His Gly Ser
850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Cys His Thr Ser Gln
            900                 905                 910

Gly Asp Pro Ile Gly Leu Ile Leu Leu Gly Glu Val Ala Leu Gly Asn
        915                 920                 925

Met Tyr Glu Leu Lys His Ala Ser His Ile Ser Lys Leu Pro Lys Gly
    930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Asn Asp Thr Ser Leu Leu Tyr Asn Glu Tyr Ile Val Tyr
            980                 985                 990

Asp Ile Ala Gln Val Asn Leu Lys  Tyr Leu Leu Lys Leu Lys Phe Asn
        995                 1000                1005

Phe Lys  Thr Ser Leu Trp
    1010

<210> SEQ ID NO 36
<211> LENGTH: 579
<212> TYPE: PRT
<213> ORGANISM: Artificial Sequence
<220> FEATURE:
<223> OTHER INFORMATION: Majority sequence from the alignment of human
      and murine PARPs
<220> FEATURE:
<221> NAME/KEY: VARIANT
<222> LOCATION: (36)..(36)
<223> OTHER INFORMATION: may be any amino acid
<220> FEATURE:
<221> NAME/KEY: VARIANT
<222> LOCATION: (48)..(48)
<223> OTHER INFORMATION: may be any amino acid
<220> FEATURE:
<221> NAME/KEY: VARIANT
<222> LOCATION: (51)..(53)
<223> OTHER INFORMATION: may be any amino acid
<220> FEATURE:
<221> NAME/KEY: VARIANT
<222> LOCATION: (57)..(57)
<223> OTHER INFORMATION: may be any amino acid
<220> FEATURE:
<221> NAME/KEY: VARIANT
<222> LOCATION: (68)..(68)
<223> OTHER INFORMATION: may be any amino acid
<220> FEATURE:
<221> NAME/KEY: VARIANT
<222> LOCATION: (72)..(72)
<223> OTHER INFORMATION: may be any amino acid
<220> FEATURE:
<221> NAME/KEY: VARIANT
<222> LOCATION: (74)..(74)
<223> OTHER INFORMATION: may be any amino acid
<220> FEATURE:
<221> NAME/KEY: VARIANT
<222> LOCATION: (80)..(80)
<223> OTHER INFORMATION: may be any amino acid
<220> FEATURE:
```

```
<221> NAME/KEY: VARIANT
<222> LOCATION: (85)..(85)
<223> OTHER INFORMATION: may be any amino acid
<220> FEATURE:
<221> NAME/KEY: VARIANT
<222> LOCATION: (89)..(89)
<223> OTHER INFORMATION: may be any amino acid
<220> FEATURE:
<221> NAME/KEY: VARIANT
<222> LOCATION: (92)..(92)
<223> OTHER INFORMATION: may be any amino acid
<220> FEATURE:
<221> NAME/KEY: VARIANT
<222> LOCATION: (106)..(106)
<223> OTHER INFORMATION: may be any amino acid
<220> FEATURE:
<221> NAME/KEY: VARIANT
<222> LOCATION: (122)..(122)
<223> OTHER INFORMATION: may be any amino acid
<220> FEATURE:
<221> NAME/KEY: VARIANT
<222> LOCATION: (126)..(126)
<223> OTHER INFORMATION: may be any amino acid
<220> FEATURE:
<221> NAME/KEY: VARIANT
<222> LOCATION: (147)..(147)
<223> OTHER INFORMATION: may be any amino acid
<220> FEATURE:
<221> NAME/KEY: VARIANT
<222> LOCATION: (156)..(156)
<223> OTHER INFORMATION: may be any amino acid
<220> FEATURE:
<221> NAME/KEY: VARIANT
<222> LOCATION: (160)..(160)
<223> OTHER INFORMATION: may be any amino acid
<220> FEATURE:
<221> NAME/KEY: VARIANT
<222> LOCATION: (172)..(172)
<223> OTHER INFORMATION: may be any amino acid
<220> FEATURE:
<221> NAME/KEY: VARIANT
<222> LOCATION: (176)..(176)
<223> OTHER INFORMATION: may be any amino acid
<220> FEATURE:
<221> NAME/KEY: VARIANT
<222> LOCATION: (188)..(188)
<223> OTHER INFORMATION: may be any amino acid
<220> FEATURE:
<221> NAME/KEY: VARIANT
<222> LOCATION: (190)..(190)
<223> OTHER INFORMATION: may be any amino acid
<220> FEATURE:
<221> NAME/KEY: VARIANT
<222> LOCATION: (201)..(201)
<223> OTHER INFORMATION: may be any amino acid
<220> FEATURE:
<221> NAME/KEY: VARIANT
<222> LOCATION: (204)..(204)
<223> OTHER INFORMATION: may be any amino acid
<220> FEATURE:
<221> NAME/KEY: VARIANT
<222> LOCATION: (211)..(211)
<223> OTHER INFORMATION: may be any amino acid
<220> FEATURE:
<221> NAME/KEY: VARIANT
<222> LOCATION: (225)..(225)
<223> OTHER INFORMATION: may be any amino acid
<220> FEATURE:
<221> NAME/KEY: VARIANT
<222> LOCATION: (241)..(241)
<223> OTHER INFORMATION: may be any amino acid
<220> FEATURE:
<221> NAME/KEY: VARIANT
<222> LOCATION: (244)..(244)
<223> OTHER INFORMATION: may be any amino acid
<220> FEATURE:
<221> NAME/KEY: VARIANT
<222> LOCATION: (274)..(274)
<223> OTHER INFORMATION: may be any amino acid
```

```
<220> FEATURE:
<221> NAME/KEY: VARIANT
<222> LOCATION: (276)..(276)
<223> OTHER INFORMATION: may be any amino acid
<220> FEATURE:
<221> NAME/KEY: VARIANT
<222> LOCATION: (279)..(279)
<223> OTHER INFORMATION: may be any amino acid
<220> FEATURE:
<221> NAME/KEY: VARIANT
<222> LOCATION: (290)..(290)
<223> OTHER INFORMATION: may be any amino acid
<220> FEATURE:
<221> NAME/KEY: VARIANT
<222> LOCATION: (301)..(301)
<223> OTHER INFORMATION: may be any amino acid
<220> FEATURE:
<221> NAME/KEY: VARIANT
<222> LOCATION: (303)..(303)
<223> OTHER INFORMATION: may be any amino acid
<220> FEATURE:
<221> NAME/KEY: VARIANT
<222> LOCATION: (312)..(312)
<223> OTHER INFORMATION: may be any amino acid
<220> FEATURE:
<221> NAME/KEY: VARIANT
<222> LOCATION: (331)..(331)
<223> OTHER INFORMATION: may be any amino acid
<220> FEATURE:
<221> NAME/KEY: VARIANT
<222> LOCATION: (335)..(337)
<223> OTHER INFORMATION: may be any amino acid
<220> FEATURE:
<221> NAME/KEY: VARIANT
<222> LOCATION: (339)..(339)
<223> OTHER INFORMATION: may be any amino acid
<220> FEATURE:
<221> NAME/KEY: VARIANT
<222> LOCATION: (341)..(341)
<223> OTHER INFORMATION: may be any amino acid
<220> FEATURE:
<221> NAME/KEY: VARIANT
<222> LOCATION: (369)..(369)
<223> OTHER INFORMATION: may be any amino acid
<220> FEATURE:
<221> NAME/KEY: VARIANT
<222> LOCATION: (384)..(384)
<223> OTHER INFORMATION: may be any amino acid
<220> FEATURE:
<221> NAME/KEY: VARIANT
<222> LOCATION: (392)..(392)
<223> OTHER INFORMATION: may be any amino acid
<220> FEATURE:
<221> NAME/KEY: VARIANT
<222> LOCATION: (403)..(403)
<223> OTHER INFORMATION: may be any amino acid
<220> FEATURE:
<221> NAME/KEY: VARIANT
<222> LOCATION: (466)..(466)
<223> OTHER INFORMATION: may be any amino acid
<220> FEATURE:
<221> NAME/KEY: VARIANT
<222> LOCATION: (469)..(469)
<223> OTHER INFORMATION: may be any amino acid
<220> FEATURE:
<221> NAME/KEY: VARIANT
<222> LOCATION: (474)..(474)
<223> OTHER INFORMATION: may be any amino acid
<220> FEATURE:
<221> NAME/KEY: VARIANT
<222> LOCATION: (487)..(487)
<223> OTHER INFORMATION: may be any amino acid
<220> FEATURE:
<221> NAME/KEY: VARIANT
<222> LOCATION: (492)..(493)
<223> OTHER INFORMATION: may be any amino acid
<220> FEATURE:
<221> NAME/KEY: VARIANT
<222> LOCATION: (540)..(540)
```

<220> FEATURE:
<221> NAME/KEY: VARIANT
<222> LOCATION: (543)..(543)
<223> OTHER INFORMATION: may be any amino acid
<220> FEATURE:
<221> NAME/KEY: VARIANT
<222> LOCATION: (545)..(545)
<223> OTHER INFORMATION: may be any amino acid
<220> FEATURE:
<221> NAME/KEY: VARIANT
<222> LOCATION: (548)..(548)
<223> OTHER INFORMATION: may be any amino acid
<220> FEATURE:
<221> NAME/KEY: VARIANT
<222> LOCATION: (559)..(559)
<223> OTHER INFORMATION: may be any amino acid
<220> FEATURE:
<221> NAME/KEY: VARIANT
<222> LOCATION: (576)..(577)
<223> OTHER INFORMATION: may be any amino acid

<400> SEQUENCE: 36

Met Ala Gly Gly Leu Arg Pro Glu Arg Cys Glu Lys Gly Lys Arg Asp
1               5                   10                  15

Lys Asp Lys Leu Leu Lys Val Phe Ala Glu Cys Tyr Cys Gly Ala Pro
            20                  25                  30

Lys Arg Lys Xaa Trp Val Gln Thr Glu Gly Ser Glu Lys Lys Lys Xaa
        35                  40                  45

Arg Gln Xaa Xaa Xaa Glu Glu Asp Xaa Phe Arg Ser Thr Ala Glu Ala
    50                  55                  60

Leu Lys Ala Xaa Pro Ala Glu Xaa Arg Xaa Ile Arg Val Asp Pro Xaa
65                  70                  75                  80

Cys Pro Leu Ser Xaa Asn Pro Gly Xaa Gln Val Xaa Glu Asp Val Tyr
                85                  90                  95

Asp Cys Thr Leu Asn Gln Thr Asn Ile Xaa Asn Asn Asn Lys Phe
            100                 105                 110

Tyr Ile Ile Gln Leu Leu Glu Asp Xaa Arg Phe Phe Xaa Cys Trp
            115                 120                 125

Asn Arg Trp Gly Arg Val Gly Glu Val Gly Gln Ser Lys Leu Asn His
130                 135                 140

Phe Thr Xaa Leu Glu Asp Ala Lys Glu Asp Phe Xaa Lys Lys Phe Xaa
145                 150                 155                 160

Glu Lys Thr Lys Asn Asn Trp Glu Glu Arg Asp Xaa Phe Val Lys Xaa
                165                 170                 175

Pro Gly Lys Tyr Thr Leu Leu Gly Val Asp Tyr Xaa Glu Xaa Glu Asp
            180                 185                 190

Glu Glu Ala Val Val Lys Ser Leu Xaa Val Asp Xaa Gly Pro Val Ser
        195                 200                 205

Thr Val Xaa Lys Arg Val Gln Pro Cys Ser Leu Asp Pro Ala Thr Gln
    210                 215                 220

Xaa Leu Ile Thr Asn Ile Phe Ser Val Glu Met Phe Lys Asn Ala Met
225                 230                 235                 240

Xaa Leu Met Xaa Leu Asp Val Lys Lys Met Pro Leu Gly Lys Leu Ser
                245                 250                 255

Lys Gln Gln Ile Ala Ala Gly Phe Glu Ala Leu Glu Ala Leu Glu Glu
            260                 265                 270

Ala Xaa Lys Xaa Gly Thr Xaa Gly Gln Ser Leu Glu Glu Leu Ser
        275                 280                 285

Ser Xaa Phe Tyr Thr Val Ile Pro His Asp Phe Gly Xaa Ser Xaa Pro

```
                290                 295                 300

Pro Leu Ile Asn Ser Pro Asp Xaa Leu Gln Ala Lys Lys Asp Met Leu
305                 310                 315                 320

Leu Val Leu Ala Asp Ile Glu Leu Ala Gln Xaa Leu Gln Ala Xaa Xaa
                325                 330                 335

Xaa Glu Xaa Ser Xaa Lys Val Glu Glu Val Pro His Pro Leu Asp Arg
                340                 345                 350

Asp Tyr Gln Leu Leu Lys Cys Gln Leu Gln Leu Leu Asp Ser Gly Ser
                355                 360                 365

Xaa Glu Tyr Lys Val Ile Gln Thr Tyr Leu Lys Gln Thr Gly Ala Xaa
                370                 375                 380

Thr His Cys Pro Tyr Thr Leu Xaa Asp Ile Phe Lys Val Glu Arg Glu
385                 390                 395                 400

Gly Glu Xaa Asp Arg Phe Gln Ala His Ser Lys Leu Gly Asn Arg Arg
                405                 410                 415

Leu Leu Trp His Gly Ser Asn Met Ala Val Val Ala Gly Ile Leu Ser
                420                 425                 430

Ser Gly Leu Arg Ile Ala Pro His Glu Ala Pro Ser Gly Gly Arg Val
                435                 440                 445

Gly Lys Gly Ile Tyr Phe Ala Ser Glu Asn Ser Lys Ser Ala Gly Tyr
                450                 455                 460

Val Xaa Thr Ser Xaa Cys Gly His Xaa Val Gly Leu Met Leu Leu
465                 470                 475                 480

Gly Glu Val Ala Leu Gly Xaa Glu His Glu Leu Xaa Xaa Ala Asn Pro
                485                 490                 495

Ser Leu Lys Ser Leu Pro Pro Gly Lys Asp Ser Val Ile Gly Leu Gly
                500                 505                 510

Lys Thr Glu Pro Asp Pro Ala Gln Asp Ile Glu Leu Gly Leu Asp Gly
                515                 520                 525

Gln Gly Val Val Val Pro Leu Gly Pro Pro Val Xaa Cys Gly Xaa Phe
                530                 535                 540

Xaa Ser Ser Xaa Phe Ser Leu Tyr Ser Glu Tyr Leu Val Tyr Xaa Glu
545                 550                 555                 560

Ser Gln Val Arg Leu Arg Tyr Leu Leu Glu Val His Phe Asn Phe Xaa
                565                 570                 575

Xaa Leu Trp

<210> SEQ ID NO 37
<211> LENGTH: 1014
<212> TYPE: PRT
<213> ORGANISM: Homo sapiens

<400> SEQUENCE: 37

Met Ala Glu Ser Ser Asp Lys Leu Tyr Arg Val Glu Tyr Ala Lys Ser
1               5                   10                  15

Glu Arg Ala Ser Cys Lys Lys Cys Ser Glu Ser Ile Pro Lys Asp Ser
                20                  25                  30

Leu Arg Met Ala Ile Met Val Gln Ser Pro Met Phe Asp Gly Lys Val
                35                  40                  45

Pro His Trp Tyr His Phe Ser Cys Phe Trp Lys Val Gly His Ser Ile
                50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
```

-continued

```
                    85                  90                  95
Lys Gly Gln Asp Gly Ile Gly Ser Lys Ala Glu Lys Thr Leu Gly Asp
                100                 105                 110

Phe Ala Ala Glu Tyr Ala Lys Ser Asn Arg Ser Thr Cys Lys Gly Cys
            115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
    195                 200                 205

Lys Gly Asp Lys Val Asp Gly Val Asp Glu Val Ala Lys Lys Lys Ser
210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
    275                 280                 285

Phe Gly Ala Leu Leu Pro Cys Glu Glu Cys Ser Gly Gln Leu Val Phe
290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
    355                 360                 365

Pro Pro Pro Ser Thr Ala Ser Ala Pro Ala Ala Val Asn Ser Ser Ala
370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
    435                 440                 445

Ala Asn Ile Arg Val Val Ser Glu Asp Phe Leu Gln Asp Val Ser Ala
450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510
```

```
Glu Gly Ile Asn Lys Ser Glu Lys Arg Met Lys Leu Thr Leu Lys
    515                 520                 525

Gly Gly Ala Ala Val Asp Pro Asp Ser Gly Leu Glu His Ser Ala His
    530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu His Phe Met Lys Leu Tyr Glu Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
    770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Asn Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
    850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Cys His Thr Ser Gln
            900                 905                 910

Gly Asp Pro Ile Gly Leu Ile Leu Leu Gly Glu Val Ala Leu Gly Asn
        915                 920                 925
```

```
Met Tyr Glu Leu Lys His Ala Ser His Ile Ser Lys Leu Pro Lys Gly
    930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
                965                 970                 975

Ser Gly Val Asn Asp Thr Ser Leu Leu Tyr Asn Glu Tyr Ile Val Tyr
            980                 985                 990

Asp Ile Ala Gln Val Asn Leu Lys Tyr Leu Leu Lys Leu Lys Phe Asn
        995                 1000                1005

Phe Lys Thr Ser Leu Trp
    1010
```

<210> SEQ ID NO 38
<211> LENGTH: 570
<212> TYPE: PRT
<213> ORGANISM: Homo sapiens

<400> SEQUENCE: 38

```
Met Ala Ala Arg Arg Arg Ser Thr Gly Gly Gly Arg Ala Arg Ala
1               5                   10                  15

Leu Asn Glu Ser Lys Arg Val Asn Asn Gly Asn Thr Ala Pro Glu Asp
                20                  25                  30

Ser Ser Pro Ala Lys Lys Thr Arg Arg Cys Gln Arg Gln Glu Ser Lys
            35                  40                  45

Lys Met Pro Val Ala Gly Gly Lys Ala Asn Lys Asp Arg Thr Glu Asp
50                  55                  60

Lys Gln Asp Glu Ser Val Lys Ala Leu Leu Lys Gly Lys Ala Pro
65                  70                  75                  80

Val Asp Pro Glu Cys Thr Ala Lys Val Gly Lys Ala His Val Tyr Cys
                85                  90                  95

Glu Gly Asn Asp Val Tyr Asp Val Met Leu Asn Gln Thr Asn Leu Gln
                100                 105                 110

Phe Asn Asn Asn Lys Tyr Tyr Leu Ile Gln Leu Leu Glu Asp Asp Ala
            115                 120                 125

Gln Arg Asn Phe Ser Val Trp Met Arg Trp Gly Arg Val Gly Lys Met
130                 135                 140

Gly Gln His Ser Leu Val Ala Cys Ser Gly Asn Leu Asn Lys Ala Lys
145                 150                 155                 160

Glu Ile Phe Gln Lys Lys Phe Leu Asp Lys Thr Lys Asn Asn Trp Glu
                165                 170                 175

Asp Arg Glu Lys Phe Glu Lys Val Pro Gly Lys Tyr Asp Met Leu Gln
            180                 185                 190

Met Asp Tyr Ala Thr Asn Thr Gln Asp Glu Glu Thr Lys Lys Glu
        195                 200                 205

Glu Ser Leu Lys Ser Pro Leu Lys Pro Glu Ser Gln Leu Asp Leu Arg
    210                 215                 220

Val Gln Glu Leu Ile Lys Leu Ile Cys Asn Val Gln Ala Met Glu Glu
225                 230                 235                 240

Met Met Met Glu Met Lys Tyr Asn Thr Lys Lys Ala Pro Leu Gly Lys
                245                 250                 255

Leu Thr Val Ala Gln Ile Lys Ala Gly Tyr Gln Ser Leu Lys Lys Ile
            260                 265                 270

Glu Asp Cys Ile Arg Ala Gly Gln His Gly Arg Ala Leu Met Glu Ala
        275                 280                 285
```

Cys Asn Glu Phe Tyr Thr Arg Ile Pro His Asp Phe Gly Leu Arg Thr
         290                 295                 300

Pro Pro Leu Ile Arg Thr Gln Lys Glu Leu Ser Glu Lys Ile Gln Leu
305                 310                 315                 320

Leu Glu Ala Leu Gly Asp Ile Glu Ile Ala Ile Lys Leu Val Lys Thr
                325                 330                 335

Glu Leu Gln Ser Pro Glu His Pro Leu Asp Gln His Tyr Arg Asn Leu
            340                 345                 350

His Cys Ala Leu Arg Pro Leu Asp His Glu Ser Tyr Glu Phe Lys Val
        355                 360                 365

Ile Ser Gln Tyr Leu Gln Ser Thr His Ala Pro Thr His Ser Asp Tyr
370                 375                 380

Thr Met Thr Leu Leu Asp Leu Phe Glu Val Glu Lys Asp Gly Glu Lys
385                 390                 395                 400

Glu Ala Phe Arg Glu Asp Leu His Asn Arg Met Leu Leu Trp His Gly
                405                 410                 415

Ser Arg Met Ser Asn Trp Val Gly Ile Leu Ser His Gly Leu Arg Ile
            420                 425                 430

Ala Pro Pro Glu Ala Pro Ile Thr Gly Tyr Met Phe Gly Lys Gly Ile
        435                 440                 445

Tyr Phe Ala Asp Met Ser Ser Lys Ser Ala Asn Tyr Cys Phe Ala Ser
450                 455                 460

Arg Leu Lys Asn Thr Gly Leu Leu Leu Leu Ser Glu Val Ala Leu Gly
465                 470                 475                 480

Gln Cys Asn Glu Leu Leu Glu Ala Asn Pro Lys Ala Glu Gly Leu Leu
                485                 490                 495

Gln Gly Lys His Ser Thr Lys Gly Leu Gly Lys Met Ala Pro Ser Ser
            500                 505                 510

Ala His Phe Val Thr Leu Asn Gly Ser Thr Val Pro Leu Gly Pro Ala
        515                 520                 525

Ser Asp Thr Gly Ile Leu Asn Pro Asp Gly Tyr Thr Leu Asn Tyr Asn
530                 535                 540

Glu Tyr Ile Val Tyr Asn Pro Asn Gln Val Arg Met Arg Tyr Leu Leu
545                 550                 555                 560

Lys Val Gln Phe Asn Phe Leu Gln Leu Trp
                565                 570

<210> SEQ ID NO 39
<211> LENGTH: 540
<212> TYPE: PRT
<213> ORGANISM: Homo sapiens

<400> SEQUENCE: 39

Met Ser Leu Leu Phe Leu Ala Met Ala Pro Lys Pro Lys Pro Trp Val
1               5                   10                  15

Gln Thr Glu Gly Pro Glu Lys Lys Lys Gly Arg Gln Ala Gly Arg Glu
                20                  25                  30

Glu Asp Pro Phe Arg Ser Thr Ala Glu Ala Leu Lys Ala Ile Pro Ala
            35                  40                  45

Glu Lys Arg Ile Ile Arg Val Asp Pro Thr Cys Pro Leu Ser Ser Asn
        50                  55                  60

Pro Gly Thr Gln Val Tyr Glu Asp Tyr Asn Cys Thr Leu Asn Gln Thr
65                  70                  75                  80

Asn Ile Glu Asn Asn Asn Asn Lys Phe Tyr Ile Ile Gln Leu Leu Gln

-continued

```
                    85                  90                  95
Asp Ser Asn Arg Phe Phe Thr Cys Trp Asn Arg Trp Gly Arg Val Gly
                100                 105                 110

Glu Val Gly Gln Ser Lys Ile Asn His Phe Thr Arg Leu Glu Asp Ala
                115                 120                 125

Lys Lys Asp Phe Glu Lys Lys Phe Arg Glu Lys Thr Lys Asn Asn Trp
130                 135                 140

Ala Glu Arg Asp His Phe Val Ser His Pro Gly Lys Tyr Thr Leu Ile
145                 150                 155                 160

Glu Val Gln Ala Glu Asp Glu Ala Gln Glu Ala Val Val Lys Val Asp
                165                 170                 175

Arg Gly Pro Val Arg Thr Val Thr Lys Arg Val Gln Pro Cys Ser Leu
                180                 185                 190

Asp Pro Ala Thr Gln Lys Leu Ile Thr Asn Ile Phe Ser Lys Glu Met
                195                 200                 205

Phe Lys Asn Thr Met Ala Leu Met Asp Leu Asp Val Lys Lys Met Pro
                210                 215                 220

Leu Gly Lys Leu Ser Lys Gln Gln Ile Ala Arg Gly Phe Glu Ala Leu
225                 230                 235                 240

Glu Ala Leu Glu Glu Ala Leu Lys Gly Pro Thr Asp Gly Gly Gln Ser
                245                 250                 255

Leu Glu Glu Leu Ser Ser His Phe Tyr Thr Val Ile Pro His Asn Phe
                260                 265                 270

Gly His Ser Gln Pro Pro Ile Asn Ser Pro Glu Leu Leu Gln Ala
                275                 280                 285

Lys Lys Asp Met Leu Leu Val Leu Ala Asp Ile Glu Leu Ala Gln Ala
                290                 295                 300

Leu Gln Ala Val Ser Glu Gln Glu Lys Thr Val Glu Glu Val Pro His
305                 310                 315                 320

Pro Leu Asp Arg Asp Tyr Gln Leu Leu Lys Cys Gln Leu Gln Leu Leu
                325                 330                 335

Asp Ser Gly Ala Pro Glu Tyr Lys Val Ile Gln Thr Tyr Leu Glu Gln
                340                 345                 350

Thr Gly Ser Asn His Arg Cys Pro Thr Leu Gln His Ile Trp Lys Val
                355                 360                 365

Asn Gln Glu Gly Glu Glu Asp Arg Phe Gln Ala His Ser Lys Leu Gly
                370                 375                 380

Asn Arg Lys Leu Leu Trp His Gly Thr Asn Met Ala Val Val Ala Ala
385                 390                 395                 400

Ile Leu Thr Ser Gly Leu Arg Ile Met Pro His Ser Gly Gly Arg Val
                405                 410                 415

Gly Lys Gly Ile Tyr Phe Ala Ser Glu Asn Ser Lys Ser Ala Gly Tyr
                420                 425                 430

Val Ile Gly Met Lys Cys Gly Ala His His Val Gly Tyr Met Phe Leu
                435                 440                 445

Gly Glu Val Ala Leu Gly Arg Glu His His Ile Asn Thr Asp Asn Pro
                450                 455                 460

Ser Leu Lys Ser Pro Pro Gly Phe Asp Ser Val Ile Ala Arg Gly
465                 470                 475                 480

His Thr Glu Pro Asp Pro Thr Gln Asp Thr Glu Leu Glu Leu Asp Gly
                485                 490                 495

Gln Gln Val Val Val Pro Gln Gly Gln Pro Val Pro Cys Pro Glu Phe
                500                 505                 510
```

```
Ser Ser Ser Thr Phe Ser Gln Ser Glu Tyr Leu Ile Tyr Gln Glu Ser
            515                 520                 525

Gln Cys Arg Leu Arg Tyr Leu Leu Glu Val His Leu
    530                 535                 540

<210> SEQ ID NO 40
<211> LENGTH: 533
<212> TYPE: PRT
<213> ORGANISM: Mus musculus

<400> SEQUENCE: 40

Met Ala Pro Lys Arg Lys Ala Ser Val Gln Thr Glu Gly Ser Lys Lys
1               5                   10                  15

Gln Arg Gln Gly Thr Glu Glu Asp Ser Phe Arg Ser Thr Ala Glu
            20                  25                  30

Ala Leu Arg Ala Ala Pro Ala Asp Asn Arg Val Ile Arg Val Asp Pro
            35                  40                  45

Ser Cys Pro Phe Ser Arg Asn Pro Gly Ile Gln Val His Glu Asp Tyr
    50                  55                  60

Asp Cys Thr Leu Asn Gln Thr Asn Ile Gly Asn Asn Asn Lys Phe
65                  70                  75                  80

Tyr Ile Ile Gln Leu Leu Glu Glu Gly Ser Arg Phe Cys Trp Asn
                85                  90                  95

Arg Trp Gly Arg Val Gly Glu Val Gly Gln Ser Lys Met Asn His Phe
                100                 105                 110

Thr Cys Leu Glu Asp Ala Lys Lys Asp Phe Lys Lys Phe Trp Glu
            115                 120                 125

Lys Thr Lys Asn Lys Trp Glu Glu Arg Asp Arg Phe Val Ala Gln Pro
130                 135                 140

Asn Lys Tyr Thr Leu Ile Glu Val Gln Gly Glu Ala Glu Ser Gln Glu
145                 150                 155                 160

Ala Val Val Lys Ala Leu Ser Pro Gln Val Asp Ser Gly Pro Val Arg
                165                 170                 175

Thr Val Val Lys Pro Cys Ser Leu Asp Pro Ala Thr Gln Asn Leu Ile
                180                 185                 190

Thr Asn Ile Phe Ser Lys Glu Met Phe Lys Asn Ala Met Thr Leu Met
            195                 200                 205

Asn Leu Asp Val Lys Lys Met Pro Leu Gly Lys Leu Thr Lys Gln Gln
            210                 215                 220

Ile Ala Arg Gly Phe Glu Ala Leu Glu Ala Leu Glu Glu Ala Met Lys
225                 230                 235                 240

Asn Pro Thr Gly Asp Gly Gln Ser Leu Glu Glu Leu Ser Ser Cys Phe
                245                 250                 255

Tyr Thr Val Ile Pro His Asn Phe Gly Arg Ser Arg Pro Pro Pro Ile
                260                 265                 270

Asn Ser Pro Asp Val Leu Gln Ala Lys Lys Asp Met Leu Leu Val Leu
            275                 280                 285

Ala Asp Ile Glu Leu Ala Gln Thr Leu Gln Ala Ala Pro Gly Glu Glu
            290                 295                 300

Glu Glu Lys Val Glu Val Pro His Pro Leu Asp Arg Asp Tyr Gln
305                 310                 315                 320

Leu Leu Arg Cys Gln Leu Gln Leu Leu Asp Ser Gly Glu Ser Glu Tyr
                325                 330                 335

Lys Ala Ile Gln Thr Tyr Leu Lys Gln Thr Gly Asn Ser Tyr Arg Cys
```

```
                        340              345              350
Pro Asn Leu Arg His Val Trp Lys Val Asn Arg Glu Gly Glu Gly Asp
    355              360              365

Arg Phe Gln Ala His Ser Lys Leu Gly Asn Arg Arg Leu Leu Trp His
    370              375              380

Gly Thr Asn Val Ala Val Val Ala Ala Ile Leu Thr Ser Gly Leu Arg
385              390              395              400

Ile Met Pro His Ser Gly Gly Arg Val Gly Lys Gly Ile Tyr Phe Ala
             405              410              415

Ser Glu Asn Ser Lys Ser Ala Gly Tyr Val Thr Thr Met His Cys Gly
             420              425              430

Gly His Gln Val Gly Tyr Met Phe Leu Gly Glu Val Ala Leu Gly Lys
             435              440              445

Glu His His Ile Thr Ile Asp Asp Pro Ser Leu Lys Ser Pro Pro Pro
    450              455              460

Gly Phe Asp Ser Val Ile Ala Arg Gly Gln Thr Glu Pro Asp Pro Ala
465              470              475              480

Gln Asp Ile Glu Leu Glu Leu Asp Gly Gln Pro Val Val Pro Gln
             485              490              495

Gly Pro Pro Val Gln Cys Pro Ser Phe Lys Ser Ser Ser Phe Ser Gln
             500              505              510

Ser Glu Tyr Leu Ile Tyr Lys Glu Ser Gln Cys Arg Leu Arg Tyr Leu
    515              520              525

Leu Glu Ile His Leu
    530
```

POLY(ADP-RIBOSE) POLYMERASE GENES

This is a continuation of U.S. patent application Ser. No. 09/701,586, filed on Nov. 30, 2000, now U.S. Pat. No. 7,754, 459, which is a U.S. national stage entry of International Patent Application No. PCT/EP1999/003889, filed on Jun. 4, 1999, the entire disclosure of each of which applications is herewith incorporated by reference. International Patent Application No. PCT/EP1999/003889 claims priority to German Patent Application No. 19908837.3, filed on Mar. 1, 1999, and German Patent Application No. 19825213.7, filed on Jun. 5, 1998.

BACKGROUND OF THE INVENTION

In 1966, Chambon and co-workers discovered a 116 kD enzyme which was characterized in detail in subsequent years and is now called PARP (EC 2.4.2.30) (poly(adenosine-5'-diphosphoribose) polymerase), PARS (poly(adenosine-5'-diphosphoribose) synthase) or ADPRT (adenosine-5'-diphosphoribose transferase). In the plant kingdom (*Arabidopsis thaliana*) a 72 kD (637 amino acids) PARP was found in 1995 (Lepiniec L. et al., FEBS Lett 1995; 364(2): 103-8). It was not clear whether this shorter form of PARP is a plant-specific individuality or an artefact ("splice" variant or the like). The 116 kD PARP enzyme has to date been unique in animals and in man in its activity, which is described below. It is referred to as PARP1 below to avoid ambiguity.

The primary physiological function of PARP 1 appears to be its involvement in a complex repair mechanism which cells have developed to repair DNA strand breaks. The primary cellular response to a DNA strand break appears moreover to consist of PARP1-catalyzed synthesis of poly(ADP-ribose) from $NAD^+$ (cf. De Murcia, G. et al. (1994) TIBS, 19, 172).

PARP 1 has a modular molecular structure. Three main functional elements have been identified to date: an N-terminal 46 kD DNA binding domain; a central 22 kD automodification domain to which poly(ADP-ribose) becomes attached, with the PARP 1 enzyme activity decreasing with increasing elongation; and a C-terminal 54 kD $NAD^5$ binding domain. A leucine zipper region has been found within the automodification domain, indicating possible protein-protein interactions, only in the PARP from *Drosophila*. All PARPs known to date are presumably active as homodimers.

The high degree of organization of the molecule is reflected in the strong conservation of the amino acid sequence. Thus, 62% conservation of the amino acid sequence has been found for PARP 1 from humans, mice, cattle and chickens. There are greater structural differences from the PARP from *Drosophila*. The individual domains themselves in turn have clusters of increased conservation. Thus, the DNA binding region contains two so-called zinc fingers as subdomains (comprising motifs of the type $CX_3CX_{28/30}HX_2C$), which are involved in the $Zn^{2+}$-dependent recognition of DNA single strand breaks or single-stranded DNA overhangs (e.g., at the chromosome ends, the telomeres). The C-terminal catalytic domain comprises a block of about 50 amino acids (residues 859-908), which is about 100% conserved among vertebrates (PARP "signature"). This block binds the natural substrate NAD* and thus governs the synthesis of poly(ADP-ribose) (cf. de Murcia, loc. cit.). The $GX_3GKG$ motif in particular is characteristic of PARPs in this block.

The beneficial function described above contrasts with a pathological one in numerous diseases (stroke, myocardial infarct, sepsis etc.). PARP is involved in cell death resulting from ischemia of the brain (Choi, D. W., (1997) Nature Medicine, 3, 10, 1073), of the myocardium (Zingarelli, B., et al (1997), Cardiovascular Research, 36, 205) and of the eye (Lam, T. T. (1997), Res. Comm. in Molecular Pathology and Pharmacology, 95, 3, 241).

PARP activation induced by inflammatory mediators has also been observed in septic shock (Szabo, C., et al. (1997), Journal of Clinical Investigation, 100, 3, 723). In these cases, activation of PARP is accompanied by extensive consumption of $NAD^+$. Since four moles of ATP are consumed for the biosynthesis of one mole of $NAD^+$, the cellular energy supply decreases drastically. The consequence is cell death.

PARP1 inhibitors described in the abovementioned specialist literature are nicotinamide and 3-aminobenzamide. 3,4-Di-hydro-5-[4-(1-piperidinyl)butoxyl-1(2H)-isoquinolone is disclosed by Takahashi, K., et al (1997), Journal of Cerebral Blood Flow and Metabolism 17, 1137. Further inhibitors are described, for example, in Banasik, M., et al. (1992) J. Biol. Chem., 267, 3, 1569 and Griffin, R. J., et al. (1995), Anti-Cancer Drug Design, 10, 507.

High molecular weight binding partners described for human PARP1 include the base excision repair (BER) protein XRCC1 (X-ray repair cross-complementing 1) which binds via a zinc finger motif and a BRCT (BRCA1 C-terminus) module (amino acids 372-524) (Masson, M., et al., (1998) Molecular and Cellular Biology, 18, 6, 3563).

BRIEF SUMMARY OF THE INVENTION

The present invention relates to novel poly(ADP-ribose) polymerase (PARP) genes and to the proteins derived therefrom; antibodies with specificity for the novel proteins; pharmaceutical and gene therapy compositions which comprise products according to the invention; methods for the analytical determination of the proteins and nucleic acids according to the invention; methods for identifying effectors or binding partners of the proteins according to the invention; methods for determining the activity of such effectors and use thereof for the diagnosis or therapy of pathological states.

It is an object of the present invention, because of the diverse physiological and pathological functions of PARP, to provide novel PARP homologs. The reason for this is that the provision of homologous PARPs would be particularly important for developing novel targets for drugs, and novel drugs, in order to improve diagnosis and/or therapy of pathological states in which PARP, PARP homologs or substances derived therefrom are involved.

BRIEF DESCRIPTION OF THE DRAWINGS

The present invention will now be described in more detail with reference to the appended figures. These show:

In FIG. 2 Northern blots with various human tissues to illustrate the tissue distribution of PARP2 and PARP3 molecules according to the invention. Lane 1: brain; lane 2: heart; lane 3: skeletal muscle; lane 4: colon; lane 5: thymus; lane 6: spleen; lane 7: kidney; lane 8: liver; lane 9: intestine; lane 10:

Figure 1:
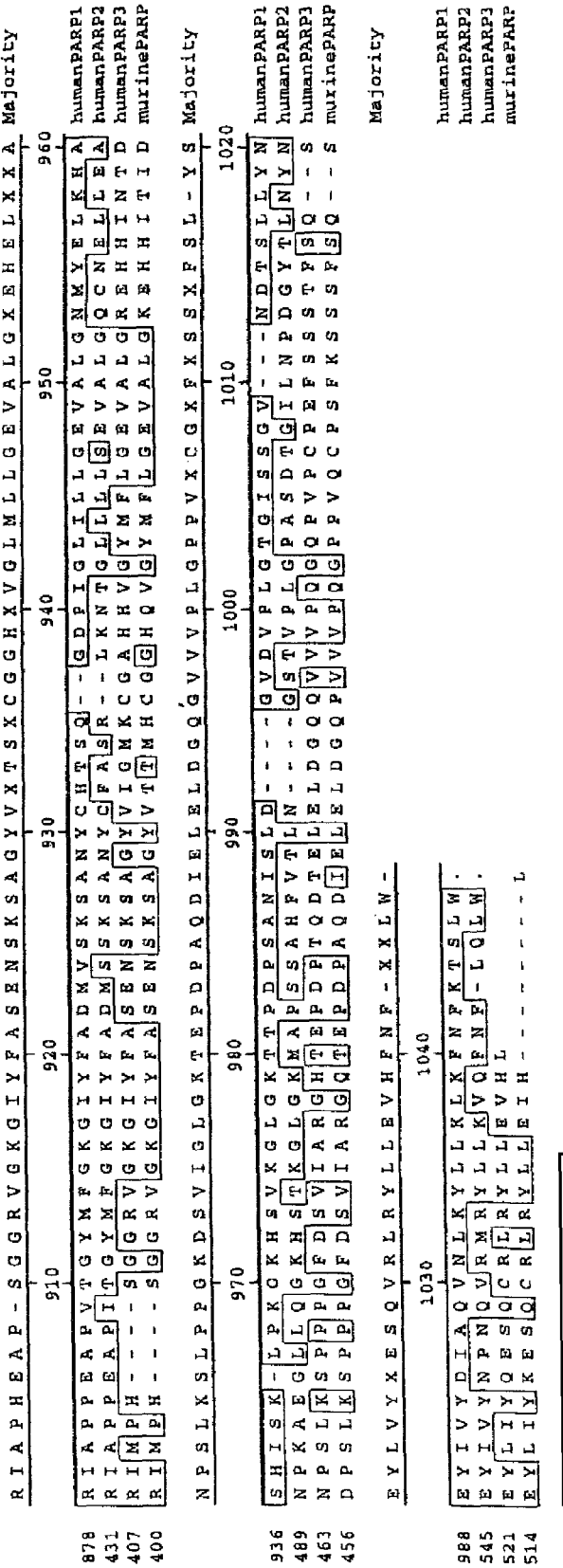
In FIG. 1 a sequence alignment of human PARP (human PARP1) and two PARPs preferred according to the invention (human PARP2, human PARP3, murine PARP3). Sequence agreements between human PARP1 and human PARP2, human PARP3 or murine PARP3 are depicted within frames. The majority sequence is indicated over the alignment. The zinc finger motifs of human PARP1 are located in the sequence sections corresponding to amino acid residues 21 to 56 and 125 to 162.

placenta; lane 11: lung; lane 12: peripheral blood leukocytes; the respective position of the size standard (kb) is indicated.

In FIG. 3 a Northern blot with further various human tissues to illustrate the tissue distribution of the PARP3 molecule according to the invention. Lane 1: heart; lane 2: brain; lane 3: placenta; lane 4: lung; lane 5: liver; lane 6: skeletal muscle; lane 7: kidney; lane 8: pancreas; the respective position of the size standard (kb) is indicated.

In FIG. 4 a Western blot with various human tissues to illustrate the tissue distribution of the PARP3 molecule according to the invention at the protein level. Lane 1: heart; lane 2: lung; lane 3: liver; lane 4: spleen; lane 5: kidney; lane 6: colon; lane 7: muscle; lane 8: brain; the respective position of the size standard (kD) is indicated.

Figure 5:
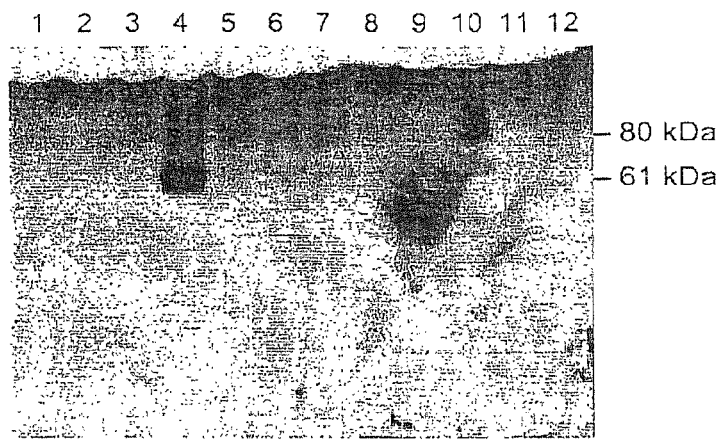

In FIG. 5 a Western blot with various human tissues to illustrate the tissue distribution of the PARP3 molecule according to the invention. Lane 1: frontal cortex; lane 2: posterior cortex; lane 3: cerebellum; lane 4: hippocampus; lane 5: olfactory bulb; lane 6: striatum; lane 7: thalamus; lane 8: midbrain; lane 9: entorhinal cortex; lane 10: pons; lane 11: medulla; lane 12: spinal cord.

Figure 6:
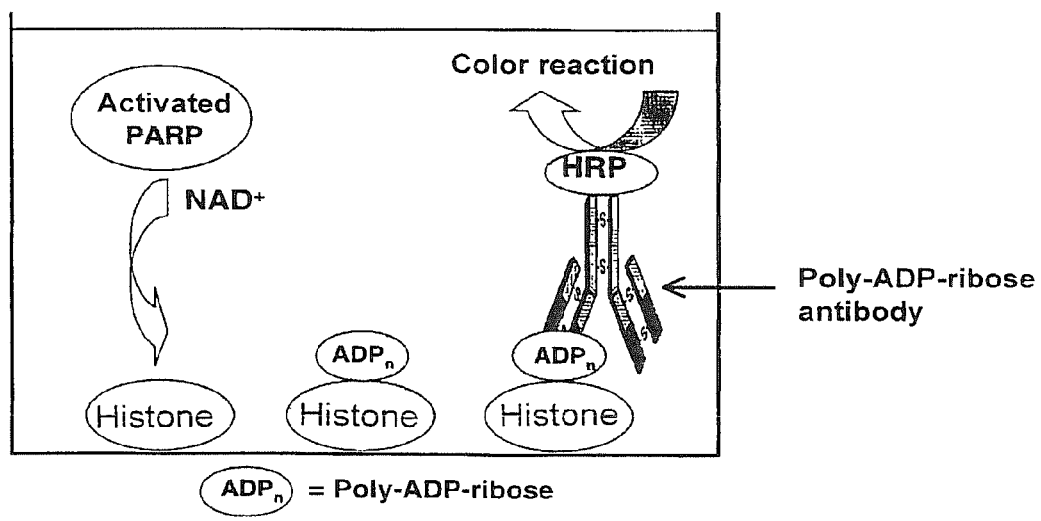

In FIG. 6 a diagrammatic representation of the PARP assay (ELISA)

Figure 7:
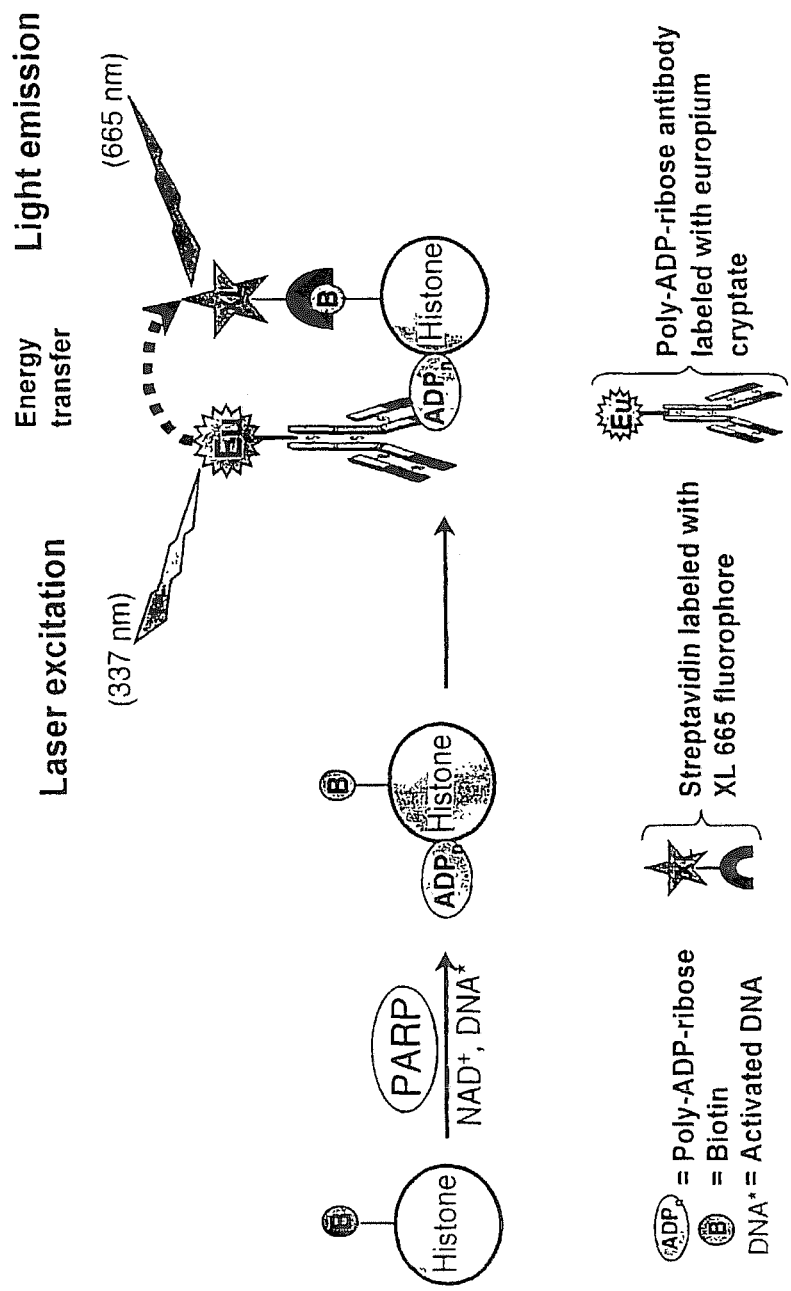

In FIG. 7 a diagrammatic representation of the PARP assay (HTRF)

DETAILED DESCRIPTION OF THE INVENTION

We have found that this object is achieved by providing PARP homologs, preferably derived from human and non-human mammals, having an amino acid sequence which has
a) a functional $NAD^+$ binding domain, i.e., a PARP "signature" sequence having the characteristic $GX_3GKG$ motif; and
b) especially in the N-terminal sequence region, i.e., in the region of the first 200, such as, for example, in the region of the first 100, N-terminal amino acids, no PARP zinc finger sequence motifs of the general formula $CX_2CX_mHX_2C$ in which
   m is an integral value from 28 or 30, and the X radicals are, independently of one another, any amino acid;
and the functional equivalents thereof.

Since the PARP molecules according to the invention represent in particular functional homologs, they naturally also have a poly(ADP-ribose)-synthesizing activity. The NAD binding domain essentially corresponds to this activity and is localized to the C terminus.

Thus an essential characteristic of the PARPs according to the invention is the presence of a functional $NAD^+$ binding domain (PARP signature) which is located in the C-terminal region of the amino acid sequence (i.e., approximately in the region of the last 400, such as, for example, the last 350 or 300, C-terminal amino acids), in combination with an N-terminal sequence having no zinc finger motifs. Since the zinc finger motifs in known PARPs presumably contribute to recognition of the DNA breakages, it is to be assumed that the proteins according to the invention do not interact with DNA or do so in another way. It has been demonstrated by appropriate biochemical tests that the PARP2 according to the invention can be activated by 'activated DNA' (i.e., DNA after limited DNaseI digestion). It can be concluded from this further that the PARP2 according to the invention has DNA binding properties. However, the mechanism of the DNA binding and enzyme activation differs between the PARPs according to the invention and PARP1. Its DNA binding and enzyme activation is, as mentioned, mediated by a characteristic zinc finger motif. No such motifs are present in the PARPs according to the invention. Presumably these properties are mediated by positively charged amino acids in the N-terminal region of the PARPs according to the invention. Since the 'activated DNA' (i.e., for example DNA after limited treatment with DNaseI) has a large number of defects (single strand breaks, single strand gaps, single-stranded overhangs, double strand breaks etc.), it is possible that although PARP1 and the PARPs according to the invention are activated by the same 'activated DNA', it is by a different subpopulation of defects (e.g., single strand gaps instead of single strand breaks).

The functional $NAD^+$ binding domain (i.e., catalytic domain) binds the substrate for poly-(ADP-ribose) synthesis. Consistent with known PARPs, the sequence motif $GX^1X^2X^3GKG$, in which G is glycine, K is lysine, and $X^1$, $X^2$ and $X^3$ are, independently of one another, any amino acid, is present in particular. However, as shown, surprisingly, by comparison of the amino acid sequences of the NAD binding domains of PARP molecules according to the invention with previously disclosed human PARP1, the sequences according to the invention differ markedly from the known sequence for the $NAD^+$ binding domain.

A group of PARP molecules which is preferred according to the invention preferably has the following general sequence motif in the catalytic domain in common:

```
                                              (SEQ ID NO: 11)
PX_n(S/T)GX_3GKGIYFA,
in particular
                                              (SEQ ID NO: 12)
(S/T)XGLR(I/V)XPX_n(S/T)GX_3GKGIYFA,
preferably
                                              (SEQ ID NO: 13)
LLWHG(S/T)X_7IL(S/T)XGLR(I/V)XPX_n(S/T)GX_3GKGIYFAX_3
SKSAXY
``` in which (S/T) describes the alternative occupation of this sequence position by S or T, (I/V) describes the alternative occupation of this sequence position by I or V, and n is an integral value from 1 to 5, and the X radicals are, independently of one another, any amino acid. The last motif is also referred to as the "PARP signature" motif.

The automodification domain is preferably likewise present in the PARPs according to the invention. It can be located, for example, in the region from about 100 to 200 amino acids in front of the N-terminal end of the NAD binding domain.

PARP homologs according to the invention may additionally comprise, N-terminally of the $NAD^+$ binding domain (i.e., about 30 to about 80 amino acids closer to the N terminus), a leucine zipper-like sequence motif of the general formula $(L/V)X_6LX_6LX_6L$           (SEQ ID NO: 14)

in which
(L/V) represents the alternative occupation of this sequence position by L or V, and the X radicals are, independently of one another, any amino acid. The leucine zipper motifs observed according to the invention differ distinctly in position from those described for PARP from *Drosophila*. Leucine zippers may lead to homodimers (two PARP molecules) or heterodimers (one PARP molecule with a binding partner differing therefrom).

The PARP homologs according to the invention preferably additionally comprise, N-terminally of the abovementioned leucine zipper-like sequence motifs, i.e., about 10 to 250 amino acid residues closer to the N terminus, at least another one of the following part-sequence motifs:

$LX_9NX_2YX_2QLLX(D/E)X_bWGRVG$, (motif 1; SEQ ID NO: 15)

$AX_3FXKX_4KTXNXWX_5FX_3PXK$, (motif 2; SEQ ID NO: 16)

$QXL(I/L)X_2IX_9MX_{10}PLGKLX_3QIX_6L$, (motif 3; SEQ ID NO: 17)

$FYTXIPHXFGX_3PP$, (motif 4; SEQ ID NO: 18)
and $KX_3LX_2LXDIEXAX_2L$, (motif 5; SEQ ID NO: 19)

in which (D/E) describes the alternative occupation of this sequence position by D or E, (I/L) describes the alternative occupation of this sequence position by I or L, b is the integral value 10 or 11, and the X radicals are, independently of one another, any amino acid. It is most preferred for these motifs 1 to 5 all to be present in the stated sequence, with motif 1 being closest to the N terminus.

The abovementioned PARP signature motif is followed in the proteins according to the invention by at least another one of the following motifs:

| | |
|---|---|
| $GX_3LXEVALG$ | (motif 6; SEQ ID NO: 20) |
| $GX_2SX_4GX_3PX_aLXGX_2V$ and | (motif 7; SEQ ID NO: 21) |
| $E(Y/F)X_2YX_3QX_4YLL$ | (motif 8; SEQ ID NO: 22) | in which (Y/F) describes the alternative occupation of this sequence position by Y or F, a is equal to 7 to 9 and X is in each case any amino acid. It is most preferred for the three C-terminal motifs all to be present and in the stated sequence, with motif 8 being closest to the C terminus.

A preferred PARP structure according to the invention may be described schematically as follows:
Motifs 1 to 5/PARP signature/motifs 6 to 8 or
motifs 1 to 5/leucine zipper/PARP signature/motifs 6 to 8
it being possible for further amino acid residues, such as, for example, up to 40, to be arranged between the individual motifs and for further amino acid residues, such as, for example, up to 80, to be arranged at the N terminus and/or at the C terminus.

PARP homologs which are particularly preferred according to the invention are the proteins human PARP2, human PARP3, mouse PARP3 and the functional equivalents thereof. The protein referred to as human PARP2 comprises 570 amino acids (cf. SEQ ID NO:2). The protein referred to as human PARP3 possibly exists in two forms. Type 1 comprises 533 amino acids (SEQ ID NO:4) and type 2 comprises 540 amino acids (SEQ ID NO:6). The forms may arise through different initiation of translation. The protein referred to as mouse PARP3 exists in two forms which differ from one another by a deletion of 5 amino acids (15 bp). Type 1 comprises 533 amino acids (SEQ ID NO: 8) and type 2 comprises 528 amino acids (SEQ ID NO:10). The PARP-homologs of the present invention differ in their sequences significantly over said PARP protein of *Arabidopsis thaliana* (see above). For example, PARP2 and PARP3 do not comprise the plant PARP specific peptide sequence AAVLDQWIPD, corresponding to amino acid residues 143 to 152 of the *Arabidopsis* protein.

The invention further relates to the binding partners for the PARP homologs according to the invention. These binding partners are preferably selected from a) antibodies and fragments such as, for example, Fv, Fab, F(ab$^1$)$_2$, thereof
b) protein-like compounds which interact, for example via the above leucine zipper region or another sequence section, with PARP, and
c) low molecular weight effectors which modulate a biological PARP function such as, for example, the catalytic PARP activity, i.e., NAD$^+$-consuming ADP ribosylation, or the binding to an activator protein or to DNA.

The invention further relates to nucleic acids comprising a) a nucleotide sequence coding for at least one PARP homolog according to the invention, or the complementary nucleotide sequence thereof;
b) a nucleotide sequence which hybridizes with a sequence as specified in a), preferably under stringent conditions; or
c) nucleotide sequences which are derived from the nucleotide sequences defined in a) and b) through the degeneracy of the genetic code.

Nucleic acids which are suitable according to the invention comprise in particular at least one of the partial sequences which code for the abovementioned amino acid sequence motifs.

Nucleic acids which are preferred according to the invention comprise nucleotide sequences as shown in SEQ ID NO: 1 and 3, and, in particular, partial sequences thereof which are characteristic of PARP homologs according to the invention, such as, for example, nucleotide sequences comprising a) nucleotides +3 to +1715 shown in SEQ ID NO:1;
b) nucleotides +242 to +1843 shown in SEQ ID NO:3;
c) nucleotides +221 to +1843 shown in SEQ ID NO:5;
d) nucleotides +112 to +1710 shown in SEQ ID NO:7; or
e) nucleotides +1 to +1584 shown in SEQ ID NO:9
or partial sequences of a), b), c), d) and e) which code for the abovementioned characteristic amino acid sequence motifs of the PARP homologs according to the invention.

The invention further relates to expression cassettes which comprise at least one of the above-described nucleotide sequences according to the invention under the genetic control of regulatory nucleotide sequences. These can be used to prepare recombinant vectors according to the invention, such as, for example, viral vectors or plasmids, which comprise at least one expression cassette according to the invention.

Recombinant microorganisms according to the invention are transformed with at least one of the abovementioned vectors.

The invention also relates to transgenic mammals transfected with a vector according to the invention.

The invention further relates to an in vitro detection method, which can be carried out homogeneously or heterogeneously, for PARP inhibitors, which comprises a) incubating an unsupported or supported poly-ADP-ribosylatable target with a reaction mixture comprising
  a1) a PARP homolog according to the invention;
  a2) a PARP activator; and
  a3) a PARP inhibitor or an analyte in which at least one PARP inhibitor is suspected;

b) carrying out the polyADP ribosylation reaction; and
c) determining the polyADP ribosylation of the target qualitatively or quantitatively.

The detection method is preferably carried out by preincubating the PARP homolog with the PARP activator and the PARP inhibitor or an analyte in which at least one PARP inhibitor is suspected, for example for about 1-30 minutes, before carrying out the poly-ADP ribosylation reaction.

After activation by DNA with single strand breaks (referred to as "activated DNA" according to the invention), PARP poly-ADP ribosylates a large number of nuclear proteins in the presence of NAD. These proteins include, on the one hand, PARP itself, but also histones etc.

The poly-ADP-ribosylatable target preferably used in the detection method is a histone protein in its native form or a poly-ADP-ribosylatable equivalent derived therefrom. A histone preparation supplied by Sigma (SIGMA, catalogue No. H-7755; histone type II-AS from calf thymus, Luck, J. M., et al., J. Biol. Chem., 233, 1407 (1958), Satake K., et al., J. Biol. Chem., 235, 2801 (1960)) was used by way of example. It is possible in principle to use all types of proteins or parts thereof amenable to poly-ADP-ribosylation by PARP. These are preferably nuclear proteins, e.g., histones, DNA polymerase, telomerase or PARP itself. Synthetic peptides derived from the corresponding proteins can also act as target.

In the ELISA according to the invention it is possible to use amounts of histones in the range from about 0.1 µg/well to about 100 µg/well, preferably about 1 µg/well to about 10 µg/well. The amounts of the PARP enzyme are in a range from about 0.2 pmol/well to about 2 nmol/well, preferably from about 2 pmol/well to about 200 pmol/well, the reaction mixture comprising in each case 100 µg/well. Reductions to smaller wells and correspondingly smaller reaction volumes are possible.

In the HTRF assay according to the invention, identical amounts of PARP are employed, and the amount of histone or modified hi-stones is in the range from about 2 ng/well to about 25 µg/well,
preferably about 25 ng/well to about 2.5 µg/well, the reaction mixture comprising in each case 50 ml/well. Reductions to smaller wells and correspondingly smaller reaction volumes are possible.

The PARP activator used according to the invention is preferably activated DNA.

Various types of damaged DNA can function as activator. DNA damage can be produced by digestion with DNases or other DNA-modifying enzymes (e.g., restriction endonucleases), by irradiation or other physical methods or chemical treatment of the DNA. It is further possible to simulate the DNA damage situation in a targeted manner using synthetic oligonucleotides. In the assays indicated by way of example, activated DNA from calf thymus was employed (Sigma, product No. D4522; CAS: 91080-16-9, prepared by the method of Aposhian and Kornberg using calf thymus DNA (SIGMA D-1501) and deoxyribonuclease type I (D-4263). Aposhian H. V. and Kornberg A., J. Biol. Chem., 237, 519 (1962)). The activated DNA was used in a concentration range from 0.1 to 1000 µg/ml, preferably from 1 to 100 µg/ml, in the reaction step.

The polyADP ribosylation reaction is started in the method according to the invention by adding $NAD^+$. The NAD concentrations were in a range from about 0.1 µM to about 10 mM, preferably in a range from about 10 µM to about 1 mM.

In the variant of the above method which can be carried out heterogeneously, the polyADP ribosylation of the supported target is determined using anti-poly(ADP-ribose) antibodies. To do this, the reaction mixture is separated from the supported target, washed and incubated with the antibody. This antibody can itself be labeled. However, as an alternative for detecting bound anti-poly(ADP-ribose) antibody a labeled secondary antibody or a corresponding labeled antibody fragment may be applied. Suitable labels are, for example, radiolabeling, chromophore- or fluoro-phore-labeling, biotinylation, chemiluminescence labeling, labeling with paramagnetic material or, in particular, enzyme labels, e.g., with horseradish peroxidase. Appropriate detection techniques are generally known to the skilled worker.

In the variant of the above process which can be carried out homogeneously, the unsupported target is labeled with an acceptor fluorophore. The target preferably used in this case is biotinylated histone, the acceptor fluorophore being coupled via avidin or streptavidin to the biotin groups of the histone. Particularly suitable as acceptor fluorophore are phycobiliproteins (e.g., phycocyanins, phycoerythrins), e.g., R-phycocyanin (R-PC), allophycocyanin
(APC), R-phycoerythrin (R-PE), C-phycocyanin (C-PC), B-phycoerythrin (B-PE) or their combinations with one another or with fluorescent dyes such as Cy5, Cy7 or Texas Red (Tandem system) (Thammapalerd, N. et al., Southeast Asian Journal of Tropical Medicine & Public Health, 27(2): 297-303 (1996); Kronick, M. N. et al., Clinical Chemistry, 29(9), 1582-1586 (1986); Hicks, J. M., Human Pathology, 15(2), 112-116 (1984)). The dye XL665 used in the examples is a crosslinked allophycocyanin (Glazer, A. N., Rev. Microbiol., 36, 173-198 (1982); Kronick, M. N., J. Imm. Meth., 92, 1-13 (1986); MacColl, R. et al., Phycobiliproteins, CRC Press, Inc., Boca Raton, Fla. (1987); MacColl, R. et al., Arch. Biochem. Biophys., 208(1), 42-48 (1981)).

It is additionally preferred in the homogeneous method to deter-mine the polyADP ribosylation of the unsupported target using anti-poly(ADP-ribose) antibody which is labeled with a donor fluorophore which is able to transfer energy to the acceptor fluorophore when donor and acceptor are close in space owing to binding of the labeled antibody to the polyADP-ribosylated histone. A europium cryptate is preferably used as donor fluorophore for the anti-poly(ADP-ribose) antibody.

Besides the europium cryptate used, other compounds are also possible as potential donor molecules. This may entail, on the one hand, modification of the cryptate cage. Replacement of the europium by other rare earth metals such as terbium is also conceivable. It is crucial that the fluorescence has a long duration to guarantee the time delay (Lopez, E. et al., Clin. Chem. 39/2, 196-201 (1993); U.S. Pat. No. 5,534, 622).

The detection methods described above are based on the principle that there is a correlation between the PARP activity and the amount of ADP-ribose polymers formed on the histones. The assay described herein makes it possible to quantify the ADP-ribose polymers using specific antibodies in the form of an ELISA and an HTRF (homogenous time-resolved fluorescence) assay. Specific embodiments of these two assays are described in detail in the following examples.

The developed HTRF (homogeneous time-resolved fluorescence) assay system measures the formation of poly(ADP-ribose) on histones using specific antibodies. In contrast to the ELISA, this assay is carried out in homogeneous phase without separation and washing steps. This makes a higher sample throughput and a smaller susceptibility to errors possible. HTRF is based on the fluorescence resonance energy transfer (FRET) between two fluorophores. In a FRET assay, an excited donor fluorophore can transfer its energy to an acceptor fluorophore when the two are close to one another in space. In HTRF technology, the donor fluorophore is a europium cryptate [(Eu)K] and the acceptor is XL665, a stabilized allophycocyanin. The europium cryptate is based on studies by Jean Marie Lehn (Strasbourg) (Lopez, E. et al., Clin. Chem. 39/2, 196-201 (1993); U.S. Pat. No. 5,534,622).

In a homogeneous assay, all the components are also present during the measurement. Whereas this has advantages for carrying out the assay (rapidity, complexity), it is necessary to preclude interference by assay components (inherent fluorescence, quenching by dyes etc.). HTRF precludes such interference by time-delayed measurement at two wavelengths (665 nm, 620 nm). The HTRF has a very long decay time and time-delayed measurement is therefore possible. There is no longer any interference from short-lived background fluorescence (e.g., from assay components or inhibitors of the substance library). In addition, measurement is always carried out at two wavelengths in order to compensate for quench effects of colored substances. HTRF assays can be carried out, for example, in 96- or 384-well microtiter plate format and are evaluated using a discovery HTRF microplate analyzer (Canberra Packard).

Also provided according to the invention are the following in vitro screening methods for binding partners for PARP, in particular for a PARP homolog according to the invention.

A first variant is carried out by
a1) immobilizing at least one PARP homolog on a support;
b1) contacting the immobilized PARP homolog with an analyte in which at least one binding partner is suspected; and
c1) determining, where appropriate after an incubation period, analyte constituents bound to the immobilized PARP homolog.

A second variant entails
a2) immobilizing on a support an analyte which comprises at least one possible binding partner for the PARP homolog;
b2) contacting the immobilized analyte with at least one PARP homolog for which a binding partner is sought; and
c2) examining the immobilized analyte, where appropriate after an incubation period, for binding of the PARP homolog.

The invention also relates to a method for the qualitative or quantitative determination of a nucleic acid encoding a PARP homolog, which comprises
a) incubating a biological sample with a defined amount of an exogenous nucleic acid according to the invention (e.g., with a length of about 20 to 500 bases or longer), hybridizing, preferably under stringent conditions, determining the hybridizing nucleic acids and, where appropriate, comparing with a standard; or
b) incubating a biological sample with a defined amount of oligonucleotide primer pairs with specificity for a PARP homolog-encoding nucleic acid, amplifying the nucleic acid, determining the amplification product and, where appropriate, comparing with a standard.

The invention further relates to a method for the qualitative or quantitative determination of a PARP homolog according to the invention, which comprises
a) incubating a biological sample with at least one binding partner specific for a PARP homolog,
b) detecting the binding partner/PARP complex and, where appropriate,
c) comparing the result with a standard.

The binding partner in this case is preferably an anti-PARP antibody or a binding fragment thereof, which carries a detectable label where appropriate.

The determination methods according to the invention for PARP, in particular for PARP homologs and for the coding nucleic acid sequences thereof, are suitable and advantageous for diagnosing sepsis- or ischemia-related tissue damage, in particular strokes, myocardial infarcts, diabetes or septic shock.

The invention further comprises a method for determining the efficacy of PARP effectors, which comprises
a) incubating a PARP homolog according to the invention with an analyte which comprises an effector of a physiological or pathological PARP activity; removing the effector again where appropriate; and
b) determining the activity of the PARP homolog, where appropriate after adding substrates or cosubstrates.

The invention further relates to gene therapy compositions which comprise in a vehicle acceptable for gene therapy a nucleic acid construct which
a) comprises an antisense nucleic acid against a coding nucleic acid according to the invention; or
b) a ribozyme against a noncoding nucleic acid according to the invention; or
c) codes for a specific PARP inhibitor.

The invention further relates to pharmaceutical compositions comprising, in a pharmaceutically acceptable vehicle, at least one PARP protein according to the invention, at least one PARP binding partner according to the invention or at least one coding nucleotide sequence according to the invention.

Finally, the invention relates to the use of binding partners of a PARP homolog for the diagnosis or therapy of pathological states in the development and/or progress of which at least one PARP protein, in particular a PARP homolog according to the invention, or a polypeptide derived therefrom, is involved. The binding partner used can be, for example, a low molecular weight binding partner whose molecular weight can be, for example, less than about 2000 dalton or less than about 1000 dalton.

The invention additionally relates to the use of PARP binding partners for the diagnosis or therapy of pathological states mediated by an energy deficit. An energy deficit for the purpose of the present invention is, in particular, a cellular energy deficit which is to be observed in the unwell patient systemically or in individual body regions, organs or organ regions, or tissues or tissue regions. This is characterized by an NAD and/or ATP depletion going beyond (above or below) the physiological range of variation of the NAD and/or ATP level and mediated preferably by a protein with PARP activity, in particular a PARP homolog according to the invention, or a polypeptide derived therefrom.

"Energy deficit-mediated disorders" for the purpose of the invention additionally comprise those in which tissue damage is attributable to cell death resulting from necrosis or apoptosis. The methods according to the invention are suitable for treating and preventing tissue damage resulting from cell damage due to apoptosis or necrosis; damage to nerve tissue due to ischemias and/or reperfusion; neurological disorders; neurodegenerative disorders; vascular stroke; for treating and preventing cardiovascular disorders; for treating other disorders or conditions such as, for example, age-related macular degeneration, AIDS or other immunodeficiency disorders; arthritis; atherosclerosis; cachexia; cancer; degenerative disorders of the skeletal muscles; diabetes; cranial trauma; inflammatory disorders of the gastrointestinal tract such as, for example, Crohn's disease; muscular dystrophy; osteoarthritis; osteoporosis; chronic and/or acute pain; kidney failure; retinal ischemia; septic shock (such as, for example, endotoxin shock); aging of the skin or aging in general; general manifestations of aging. The methods according to the invention can additionally be employed for extending the life and the proliferative capacity of body cells and for sensitizing tumor cells in connection with irradiation therapy.

The invention particularly relates to the use of a PARP binding partner as defined above for the diagnosis or therapy (acute or prophylactic) of pathological states mediated by energy deficits and selected from neurodegenerative disorders, or tissue damage caused by sepsis or ischemia, in particular of neurotoxic disturbances, strokes, myocardial infarcts, damage during or after infarct lysis (e.g., with TPA, Reteplase or mechanically with laser or Rotablator) and of microinfarcts during and after heart valve replacement, aneurysm resections and heart transplants, trauma to the head and spinal cord, infarcts of the kidney (acute kidney failure, acute renal insufficiency or damage during and after kidney transplant), damages of skeletal muscle, infarcts of the liver (liver failure, damage during or after a liver trans-plant), peripheral neuropathies, AIDS dementia, septic shock, diabetes, neurodegenerative disorders occurring after ischemia, trauma (craniocerebral trauma), massive bleeding, subarachnoid hemorrhages and stroke, as well as neurodegenerative disorders like Alzheimer's disease, multi-infarct dementia, Huntington's disease, Parkinson's disease, amyotrophic lateral sclerosis, epilepsy, especially of generalized epileptic seizures such as petit mal and tonoclonic seizures and partial epileptic seizures, such as temporal lobe, and complex partial seizures, kidney failure, also in the chemotherapy of tumors and prevention of meta-stasis and for the treatment of inflammations and rheumatic disorders, e.g., of rheumatoid arthritis; further for the treatment of revascularization of critically narrowed coronary arteries and critically narrowed peripheral arteries, e.g., leg arteries.

"Ischemia" comprises for the purposes of the invention a localized undersupply of oxygen to a tissue, caused by blockage of arterial blood flow. Global ischemia occurs when the blood flow to the entire brain is interrupted for a limited period. This may be caused, for example, by cardiac arrest. Focal ischemia occurs when part of the brain is cut off from its normal blood supply. Focal ischemia may be caused by thromboembolic closure of a blood vessel, by cerebral trauma, edemas or brain tumor. Even transient ischemias can lead to wide ranging neuronal damage. Although damage to "nerve tissue" may occur days or weeks after the start of the ischemia, some permanent damage (e.g., necrotic cell death) occurs in the first few minutes after interruption of the blood supply. This damage is caused, for example, by the neurotoxicity of glutamate and follows secondary reperfusion, such as, for example, release of free radicals (e.g., oxygen free radicals, NO free radicals). Ischemias may likewise occur in other organs and tissues such as, for example, in the heart (myocardial infarct and other cardiovascular disorders caused by occlusion of the coronary arteries) or in the eye (ischemia of the retina).

The invention additionally relates to the use of an effective therapeutic amount of a PARP binding partner for influencing neuronal activity. "Neuronal activity" for the purposes of the invention may consist of stimulation of damaged neurons, promotion of neuronal regeneration or treatment of neuronal disorders.

"Neuronal damage" for the purposes of the invention comprises every type of damage to "nerve tissue" and every physical or mental impairment or death resulting from this damage. The cause of the damage may be, for example, metabolic, toxic, chemical or thermal in nature and includes by way of example ischemias, hypoxias, trauma, cerebrovascular damage, operations, pressure, hemorrhages, irradiation, vasospasms, neurodegenerative disorders, infections, epilepsy, perception disorders, disturbances of glutamate metabolism and the secondary effects caused thereby.

"Nerve tissue" for the purposes of the invention comprises the various components forming the nervous system, consisting of, inter alis, neurons, glia cells, astrocytes, Schwann cells, the vascular system inside and for supplying, the CNS, brain, brain stem, spinal cord, peripheral nervous system etc.

"Neuroprotective" for the purposes of the invention comprises the reduction, the cessation, the slowing down or the improvement of neuronal damage and the protection, the restoration and the regeneration of nerve tissue which was exposed to neuronal damage.

"Prevention of neurodegenerative disorders" includes the possibility of preventing, slowing down and improving neurodegenerative disorders in people for whom such a disorder has been diagnosed or who are included in appropriate risk groups for these neurode-generative disorders. Treatments for people already suffering from symptoms of these disorders are likewise meant.

"Treatment" for the purposes of the invention comprises
(i) preventing a disorder, a disturbance or a condition in people with a predisposition thereto;
(ii) preventing a disorder, a disturbance or a condition by slowing down its advance; and
(iii) improving a disorder, a disturbance or a condition.

Examples of "neurological disorders" may include neuralgias (trigeminal, glossopharyngeal), myasthenia gravis, muscular dystrophies, amyorophic lateral sclerosis (ALS), progressive muscular atrophy, peripheral neuropathies caused by poisoning (e.g., lead poisoning), Guillain-Barré syndrome, Huntington's disease, Alzheimer's disease, Parkinson's disease, or plexus disorders. The methods according to the invention are preferably suitable for treating neurological disorders selected from peripheral neuropathies caused by physical injury or illness; cranial trauma such as, for example, traumatic brain injury; physical damage to the spinal cord; stroke associated with brain damage, such as vascular stroke in conjunction with hypoxia and brain damage, and cerebral reperfusion damage; demyelinating disorders (myelopathies, Alzheimer's disease, Parkinson's disease, Huntington's disease, amyotrophic lateral sclerosis).

The methods according to the invention can additionally be used for treating cardiovascular disorders. "Cardiovascular disorders" for the purposes of the invention comprise those which cause ischemias or are caused by ischemias or ischemia/reperfusion of the heart. Examples are coronary vessel disorders (for example atherosclerosis), angina pectoris, myocardial infarct, cardiovascular damage due to cardiac arrest or bypass operation.

The methods according to the invention can be used for treating cancer or for sensitizing cancer cells for irradiation therapy. The term "cancer" is to be understood in the widest sense. Modulators of the proteins according to the invention can be used as "anti-cancer therapy agents". For example, the methods can be used for treating types of cancer or tumor cells, such as ACTH-producing tumors, acute lymphatic or lymphoblastic leukemia; acute or chronic lymphocytic leukemia; acute nonlymphocytic leukemia; bladder cancer; brain tumors; breast cancer; cervical carcinoma; chronic myelocytic leukemia; bowel cancer; T-zone lymphoma; endometriosis; esophageal cancer; gall bladder cancer; Ewing's sarcoma; head and neck cancer; cancer of the tongue; Hodgkin's lymphoma; Kaposi's sarcoma; renal cancer; liver cancer; lung cancer; mesothelioma; multiple myeloma; neuroblastoma; non-Hodgkin lymphoma; osteosarcoma; ovarian carcinoma; glioblastoma; mammary carcinoma; cervical carcinoma; prostate cancer; pancreas-tic cancer; penis cancer; retinoblastoma; skin cancer; stomach cancer; thyroid cancer; uterine carcinoma; vaginal carcinoma; Wilm's tumor; or trophoblastoma.

"Radiosensitizer" or "irradiation sensitizer" for the purposes of the invention relates to molecules which increase the sensitivity of the cells in the body to irradiation with electromagnetic radiation (for example X-rays) or speed up this irradiation treatment. Irradiation sensitizers increase the sensitivity of cancer cells to the toxic effects of the electromagnetic radiation. Those disclosed in the literature include mitomycin C, 5-bromo-deoxyuridine and metronidazole. It is possible to use radiation with wavelengths in the range from $10^{-20}$ to 10 meters, preferably gamma rays ($10^{-20}$ to $10^{-13}$ m), X-rays ($10^{-1}$ 1 to $10^{-9}$ m), ultraviolet radiation (10 nm to 400 nm), visible light (400 nm to 700 nm), infrared radiation (700 nm to 1 mm) and microwave radiation (1 mm to 30 cm).

Disorders which can be treated by such a therapy are, in particular, neoplastic disorders, benign or malignant tumors and cancer. The treatment of other disorders using electromagnetic radiation is likewise possible.

The present invention will now be described in more detail with reference to the appended figures. These show:

In FIG. 1 a sequence alignment of human PARP (human PARP1) and two PARPs preferred according to the invention (human PARP2, human PARP3, murine PARP3). Sequence agreements between human PARP1 and human PARP2, human PARP3 or murine PARP3 are depicted within frames. The majority sequence is indicated over the alignment. The zinc finger motifs of human PARP1 are located in the sequence sections corresponding to amino acid residues 21 to 56 and 125 to 162;

In FIG. 2 Northern blots with various human tissues to illustrate the tissue distribution of PARP2 and PARP3 molecules according to the invention. Lane 1: brain; lane 2: heart; lane 3: skeletal muscle; lane 4: colon; lane 5: thymus; lane 6: spleen; lane 7: kidney; lane 8: liver; lane 9: intestine; lane 10: placenta; lane 11: lung; lane 12: peripheral blood leukocytes; the respective position of the size standard (kb) is indicated.

In FIG. 3 a Northern blot with further various human tissues to illustrate the tissue distribution of the PARP3 molecule according to the invention. Lane 1: heart; lane 2: brain; lane 3: placenta; lane 4: lung; lane 5: liver; lane 6: skeletal muscle; lane 7: kidney; lane 8: pancreas; the respective position of the size standard (kb) is indicated.

In FIG. 4 a Western blot with various human tissues to illustrate the tissue distribution of the PARP3 molecule according to the invention at the protein level. Lane 1: heart; lane 2: lung; lane 3: liver; lane 4: spleen; lane 5: kidney; lane 6: colon; lane 7: muscle; lane 8: brain; the respective position of the size standard (kD) is indicated.

In FIG. 5 a Western blot with various human tissues to illustrate the tissue distribution of the PARP3 molecule according to the invention. Lane 1: frontal cortex; lane 2: posterior cortex; lane 3: cerebellum; lane 4: hippocampus; lane 5: olfactory bulb; lane 6: striatum; lane 7: thalamus; lane 8: midbrain; lane 9: entorhinal cortex; lane 10: pons; lane 11: medulla; lane 12: spinal cord.

In FIG. 6 a diagrammatic representation of the PARP assay (ELISA)

In FIG. 7 a diagrammatic representation of the PARP assay (HTRF)

Further preferred embodiments of the invention are described in the following sections.

PARP Homologs and Functional Equivalents

Unless stated otherwise, for the purposes of the present description amino acid sequences are indicated starting with the N terminus. If the one-letter code is used for amino acids, then G is glycine, A is alanine, V is valine, L is leucine, I is isoleucine, S is serine, T is threonine, D is aspartic acid, N is asparagine, E is glutamic acid, Q is glutamine, W is tryptophan, H is histidine, R is arginine, P is proline, K is lysine, Y is tyrosine, F is phenylalanine, C is cysteine and M is methionine.

The present invention is not confined to the PARP homologs specifically described above. On the contrary, those homologs which are functional equivalents thereof are also embraced. Functional equivalents comprise both natural, such as, for example, species-specific or organ-specific, and artificially produced variants of the proteins specifically described herein. Functional equivalents according to the invention differ by addition, substitution, inversion, insertion and/or deletion of one or more amino acid residues of human PARP2 (SEQ ID NO:2), human PARP3 (SEQ ID NO: 4 and 6) and mouse PARP3 (SEQ ID:B and 10), there being at least retention of the NAD-binding function of the protein mediated by a functional catalytic C-terminal domain. Likewise, the poly(ADP-ribose)-producing catalytic activity should preferably be retained. Functional equivalents also comprise where appropriate those variants in which the region similar to the leucine zipper is essentially retained.

It is moreover possible, for example, starting from the sequence for human PARP2 or human PARP3 to replace certain amino acids by those with similar physicochemical properties (bulk, basicity, hydrophobicity, etc.). It is possible, for example, for arginine residues to be replaced by lysine residues, valine residues by isoleucine residues or aspartic acid residues by glutamic acid residues. However, it is also possible for one or more amino acids to be exchanged in sequence, added or deleted, or several of these measures can be combined together. The proteins which have been modified in this way from the human PARP2 or human PARP3 sequence have at least 60%, preferably at least 75%, very particularly preferably at least 85%, homology with the starting sequence, calculated using the algorithm of Pearson and Lipman, Proc. Natl. Acad. Sci. (USA) 85(8), 1988, 2444-2448.

The following homologies have been determined at the amino acid level and DNA level between human PARP1, 2 and 3 (FastA program, Pearson and Lipman, loc. cit.):
Amino Acid Homologies:

|  | Percent identity | Percent identity in PARP signature |
| --- | --- | --- |
| PARP1/PARP2 | 41.97% (517) | 86% (50) |
| PARP1/PARP3 | 33.81% (565) | 53.1% (49) |
| PARP2/PARP3 | 35.20% (537) | 53:1% (49) |

Numbers in parentheses indicate the number of overlapping amino acids.
DNA Homologies:

|  | Percent identity in the ORF | Percent identity in PARP signature |
| --- | --- | --- |
| PARP1/PARP2 | 60.81% (467) | 77.851; (149) |
| PARP1/PARP3 | 58.81% (420) | 59.02% (61) |
| PARP2/PARP3 | 60.22% (269) | 86.36% (22) |

Numbers in parentheses indicate the number of overlapping nucleotides.

The polypeptides according to the invention can be classified as homologous poly(ADP-ribose) polymerases on the basis of the great similarity in the region of the catalytic domain.

It is also essential to the invention that the novel PARP homologs do not have conventional zinc finger motifs. This means that these enzymes are not necessarily involved in DNA repair or are so in a way which differs from PARP1, but are still able to carry out their pathological mechanism (NAD consumption and thus energy consumption due to ATP consumption). The strong protein expression, particularly of PARP3, observable in the Western blot suggests a significant role in the NAD consumption. This is particularly important for drug development. Potential novel inhibitors of the polymerases according to the invention can thus inhibit the pathological functions without having adverse effects on the desired physiological properties. This was impossible with inhibitors against the PARPs known to date since there was always also inhibition of the DNA repair function. The potentially mutagenic effect of known PARP inhibitors is thus easy to understand. It is also conceivable to design PARP inhibitors so. that they efficiently inhibit all PARP homologs with high affinity. In this case, a potentiated effect is conceivable where appropriate.

The PARP homolog which is preferred according to the invention and is shown in SEQ ID NO:2 (human PARP2) can advantageously be isolated from human brain, heart, skeletal muscle, kidney and liver. The expression of human PARP2 in other tissues or organs is distinctly weaker.

The PARP homolog which is preferred according to the invention and is shown in SEQ ID NO: 4 and 6 (human PARP3) can advantageously be isolated from human brain (in this case very preferentially from the hippocampus), heart, skeletal muscle, liver or kidney. The expression of human PARP3 in other tissues or organs, such as muscle or liver, is distinctly weaker.

The skilled worker familiar with protein isolation will make use of the combination of preparative methodologies which is most suitable in each case for isolating natural PARPs according to the invention from tissues or recombinantly prepared PARPs according to the invention from cell cultures. Suitable standard preparative methods are described, for example, in Cooper, T. G., Biochemische Arbeitsmethoden, published by Walter de Gruyter, Berlin, New York or in Scopes, R. Protein Purification, Springer Verlag, New York, Heidelberg, Berlin.

The invention additionally relates to PARP2 and PARP3 homologs which, although they can be isolated from other eukaryotic species, i.e., invertebrates or vertebrates, especially other mammals such as, for example, mice, rats, cats, dogs, pigs, sheep, cattle, horses or monkeys, or from other organs such as, for example the myocardium, have the essential structural and functional properties predetermined by the PARPs according to the invention.

In particular, the human PARP2 which can be isolated from human brain, and its functional equivalents, are preferred agents for developing inhibitors of neurodegenerative diseases as for example stroke. This is because it can be assumed that drug development based on PARP2 as indicator makes it possible to develop inhibitors which are optimized for use in the human brain. However, it cannot be ruled out that inhibitors developed on the basis of PARP2 can also be employed for treating PARP-mediated pathological states in other organs, too (see tissue distribution of the proteins according to the invention).

PARP2 and presumably PARP3 are also, similar to PARP1, activated by damaged DNA, although by a presumably different mechanism. Significance in DNA repair is conceivable. Blockade of the PARPs according to the invention would also be beneficial in indications such as cancer (e.g., in the radiosensitization of tumor patients).

Another essential biological property of PARPs according to the invention and their functional equivalents is to be seen in their ability to bind an interacting partner. Human PARP2 and 3 differ from previously disclosed PARPs from higher eukaryotes such as, in particular, mammals by having potential so-called leucine zipper motifs. This is a typical motif for protein-protein interactions. It is possible that these motifs permit modulation of PARP activity by an interacting partner. This additional structural element thus also provides a possible starting point for development of PARE, effectors such as, for example, inhibitors.

The invention thus further relates to proteins which interact with PARP2 and/or 3, preferably those which bring about their activation or inactivation.

The invention further relates to proteins which still have the abovementioned ligand-binding activity and which can be prepared starting from the specifically disclosed amino acid sequences by targeted modifications.

It is possible, starting from the peptide sequence of the proteins according to the invention, to generate synthetic peptides which are employed, singly or in combination, as antigens for producing polyclonal or monoclonal antibodies. It is also possible to employ the PARP protein or fragments thereof for generating antibodies. The invention thus also relates to peptide fragments of PARP proteins according to the invention which comprise characteristic partial sequences, in particular those oligo- or polypeptides which comprise at least one of the abovementioned sequence motifs. Fragments of this type can be obtained, for example, by proteolytic digestion of PARE, proteins or by chemical synthesis of peptides.

Novel Specific PARP2 and PARP3 Binding Partners

Active and preferably selective inhibitors against the proteins according to the invention were developed using the specific assay systems described above for binding partners for PARP2 and PARP3. These inhibitors optionally are also active vis a vis PARP1.

Inhibitors provided according to the invention have a strong inhibitory activity on PARP2. The $K_i$ values may in this case be less than about 1000 nM, such as less than about 700 nM, less than about 200 nM or less than about 30 nM, e.g., about 1 to 20 nM.

Inhibitors according to the invention may also have a surprising selectivity for PARP2. This is shown by the $K_i(PARP1)$ $K_i(PARP2)$ ratio for such inhibitors according to the invention which is,
for example, greater than 3 or greater than 5, as for example greater than 10 or greater than 20.

An example which should be mentioned is 4-(N-(4-hydroxyphe-nyl)aminomethyl)-(2H)-dihydrophthalazine-1-one. The preparation of this and other analogous compounds may be performed according to Puodzhyunas et al., Pharm. Chem. J. 1973, 7, 566 or Mazkanowa et al., Zh. Obshch. Khim., 1958, 28, 2798, or Mohamed et al., Ind. J. Chem. B., 1994, 33, 769 each incorporated by reference.

The above identified compound shows a $K_i$ value of 113 nM for PARP2 and is eight times more selective for PARP2 than for PARP3.

Nucleic Acids Coding for PARP Homologs:

Unless stated otherwise, nucleotide sequences are indicated in the present description from the 5' to the 3' direction.

The invention further relates to nucleic acid sequences which code for the abovementioned proteins, in particular for those having the amino acid sequence depicted in SEQ ID NO: 2, 4, 6, B and 10, but without being restricted thereto. Nucleic acid sequences which can be used according to the invention also comprise allelic variants which, as described above for the amino acid sequences, are obtainable by deletion, inversion, insertion, addition and/or substitution of nucleotides, preferably of nucleotides shown in SEQ ID NO: 1, 3, 7 and 9, but with essential retention of the biological properties and the biological activity of the corresponding gene product. Nucleotide sequences which can be used are obtained, for example, by nucleotide substitutions causing silent (without alteration of the amino acid sequence) or conservative amino acid changes (exchange of amino acids of the same size, charge, polarity or solubility).

Nucleic acid sequences according to the invention also embrace functional equivalents of the genes, such as eukaryotic homologs for example from invertebrates such as *Caenorhabditis* or *Drosophila*, or vertebrates, preferably from the mammals described above. Preferred genes are those from vertebrates which code for a gene product which has the properties essential to the invention as described above.

The nucleic acids according to the invention can be obtained in a conventional way by various routes:

For example, a genomic or a cDNA library can be screened for DNA which codes for a PARP molecule or a part thereof. For example, a cDNA library obtained from human brain, heart or kidney can be screened with a suitable probe such as, for example, a labeled single-stranded DNA fragment which corresponds to a partial sequence of suitable length selected from SEQ ID NO: 1 or 3, or sequence complementary thereto. For this purpose, it is possible, for example, for the DNA fragments of the library which have been transferred into a suitable cloning vector to be, after transformation into a bacterium, plated out on agar plates. The clones can then be transferred to nitrocellulose filters and, after denaturation of the DNA, hybridized with the labeled probe. Positive clones are then isolated and characterized.

The DNA coding for PARP homologs according to the invention or partial fragments can also be synthesized chemically starting from the sequence information contained in the present application. For example, it is possible for this purpose for oligonucleotides with a length of about 100 bases to be synthesized and sequentially ligated in a manner known per se by, for example, providing suitable terminal restriction cleavage sites.

The nucleotide sequences according to the invention can also be prepared with the aid of the polymerase chain reaction (PCR). For this, a target DNA such as, for example, DNA from a suitable full-length clone is hybridized with a pair of synthetic oligonucleotide primers which have a length of about 15 bases and which bind to opposite ends of the target DNA. The sequence section lying between them is then filled in with DNA polymerase. Repetition of this cycle many times allows the target DNA to be amplified (cf. White et al. (1989), Trends Genet. 5, 185).

The nucleic acid sequences according to the invention are also to be understood to include truncated sequences, single-stranded DNA or RNA of the coding and noncoding, complementary DNA sequence, mRNA sequences and cDNAs derived therefrom.

The invention further embraces nucleotide sequences hybridizing with the above sequences under stringent conditions. Stringent hybridization conditions for the purpose of the present invention exist when the hybridizing sequences have a homology of about 70 to 100%, such as, for example about 80 to 1000 or 90 to 1000 (preferably in an amino acid section of at least about 40, such as, for example, about 50, 100, 150, 200, 400 or 500 amino acids).

Stringent conditions for the screening of DNA, in particular cDNA banks, exist, for example, when the hybridization mixture is washed with 0.1×SSC buffer (20×SSC buffer=3M NaCl, 0.3M sodium citrate, pH 7.0) and 0.1% SDS at a temperature of about 60° C.

Northern blot analyses are analyses are washed under stringent conditions with 0.1×SSC, 0.1% SDS at a temperature of about 65° C., for example.

Nucleic Acid Derivatives and Expression Constructs:

The nucleic acid sequences are also to be understood to include derivatives such as, for example, promoter variants or alternative splicing variants. The promoters operatively linked upstream of the nucleotide sequences according to the invention may moreover be modified by nucleotide addition(s) or substitution(s), inversion(s), insertion(s) and/or deletion(s), but without impairing the functionality or activity of the promoters. The promoters can also have their activity increased by modifying their sequence, or be completely replaced by more effective promoters even from heterologous organisms. The promoter variants described above are used to prepare expression cassettes according to the invention.

Specific examples of human PARP2 splicing variants which may be mentioned are:

Variant human PARP2a: Deletion of base pairs 766 to 904 (cf. SEQ ID NO:1). This leads to a frame shift with a new stop codon ("TAA" corresponding to nucleotides 922 to 924 in SEQ ID NO:1). Variant human PARP2b: Insertion of 5'-gta tgc cag gaa ggt cat ggg cca gca aaa ggg tct ctg-3' after nucleotide 204 (SEQ ID NO:1). This extends the amino acid sequence by the insertion: GMPGRSWASKRVS Nucleic acid derivatives also mean variants whose nucleotide sequences in the region from −1 to −1000 in front of the start codon have been modified so that gene expression and/or protein expression is increased.

Besides the nucleotide sequence described above, the nucleic acid constructs which can be used according to the invention comprise in functional, operative linkage one or more other regulatory sequences, such as promoters, amplification signals, enhancers, polyadenylation sequences, origins of replication, reporter genes, selectable marker genes and the like. This linkage may, depending on the desired use, lead to an increase or decrease in gene expression.

In addition to the novel regulatory sequences, it is possible for the natural regulatory sequence still to be present in front of the actual structural genes. This natural regulation can, where appropriate, be switched off by genetic modification, and the expression of the genes increased or decreased. However, the gene construct may also have a simpler structure, that is to say no additional regulatory signals are inserted in front of the structural genes, and the natural promoter with its regulation is not deleted. Instead, the natural regulatory sequence is mutated in such a way that regulation no longer takes place, and gene expression is enhanced or diminished. It is also possible to insert additional advantageous regulatory elements at the 3' end of the nucleic acid sequences. The nucleic acid sequences can be present in one or more copies in the gene construct.

Advantageous regulatory sequences for the expression method according to the invention are, for example, present in promoters such as cos, tac, trp, tet, trp-tet, lpp, lac, lpp-lac, lacIq,
T7, T5, T3, gal, trc, ara, SP6, 1-PR or the 1-PL promoter, which are advantageously used in Gram-negative bacteria. Other advantageous regulatory sequences are present, for example, in the Gram-positive promoters amy and SPO2, in the yeast promoters ADC1, MFa, AC, P-60, CYC1, GAPDH or in the plant promoters CaMV/35S, SSU, OCS, lib4, usp, STLS1, B33, nos or in the ubiquitin or phaseolin promoter.

It is possible in principle to use all natural promoters with their regulatory sequences. It is also possible and advantageous to use synthetic promoters.

Said regulatory sequences are intended to make specific expression of the nucleic acid sequences and protein expression possible. This may mean, for example, depending on the host organism that the gene is expressed or overexpressed only after induction, or that it is immediately expressed and/or overexpressed.

The regulatory sequences or factors may moreover preferably have a positive influence on, and thus increase or decrease, the expression. Thus, enhancement of the regulatory elements may advantageously take place at the level of transcription by using strong transcription signals such as promoters and/or enhancers.

However, it is also possible to enhance translation by, for example, improving the stability of the mRNA.

Enhancers mean, for example, DNA sequences which bring about increased expression via an improved interaction between RNA polymerase and DNA.

The recombinant nucleic acid construct or gene construct is, for expression in a suitable host organism, advantageously inserted into a host-specific vector which makes optimal expression of the genes in the host possible. Vectors are well known to the skilled worker and are to be found, for example, in "Cloning Vectors" (Pouwels P. H. et al., Ed., Elsevier, Amsterdam-New York-Oxford, 1985). Apart from plasmids, vectors also mean all other vectors known to the skilled worker, such as, for example, phages, viruses, such as SV40, CMV, baculovirus and adenovirus, transposons, IS elements, phasmids, cosmids, and linear or circular DNA. These vectors may undergo autonomous replication in the host organism or chromosomal replication.

Expression of the Constructs:

The recombinant constructs according to the invention described above are advantageously introduced into a suitable host system and are expressed. Cloning and transfection methods familiar to the skilled worker are preferably used in order to bring about expression of said nucleic acids in the particular expression system. Suitable systems are described, for example, in Current Protocols in Molecular Biology, F. Ausubel et al., ed., Wiley Interscience, New York 1997.

Suitable host organisms are in principle all organisms which make it possible to express the nucleic acids according to the invention, their allelic variants, their functional equivalents or derivatives or the recombinant nucleic acid construct. Host organisms mean, for example, bacteria, fungi, yeasts, plant or animal cells. Preferred organisms are bacteria such as those of the genera *Escherichia*, such as, for example, *Escherichia coli, Streptomyces, Bacillus* or *Pseudomonas*, eukaryotic microorganisms such as *Saccharomyces cerevisiae, Aspergillus*, higher eukaryotic cells from animals or plants, for example Sf9 or CHO cells.

The gene product can also, if required, be expressed in transgenic organisms such as transgenic animals such as, in particular, mice, sheep, or transgenic plants. The transgenic organisms may also be so-called knock-out animals or plants in which the corresponding endogenous gene has been switched off, such as, for example, by mutation or partial or complete deletion.

The combination of the host organisms and the vectors appropriate for the organisms, such as plasmids, viruses or phages, such as, for example, plasmids with the RNA polymerase/promoter system, phages λ, μ or other temperate phages or transposons and/or other advantageous regulatory sequences forms an expression system. The term expression systems preferably means, for example, a combination of mammalian cells such as CHO cells, and vectors, such as pcDNA3neo vector, which are suitable for mammalian cells.

As described above, the gene product can also be expressed advantageously in transgenic animals, e.g., mice, sheep, or transgenic plants. It is likewise possible to program cell-free translation systems with the RNA derived from the nucleic acid.

The gene product can also be expressed in the form of therapeutically or diagnostically suitable fragments. To isolate the recombinant protein it is possible and advantageous to use vector systems or oligonucleotides which extend the cDNA by certain nucleotide sequences and thus code for modified polypeptides which serve to simplify purification. Suitable modifications of this type are, for example, so-called tags which act as anchors, such as, for example, the modification known as the hexa-histidine anchor, or epitopes which can be recognized as antigens by antibodies (described, for example, in Harlow, E and Lane, D., 1988, Antibodies: A Laboratory Manual. Cold Spring Harbor (N.Y.) Press). These anchors can be used to attach the proteins to a solid support such as, for example, a polymer matrix, which can, for example, be packed into a chromatography column, or to a microtiter plate or to another support.

These anchors can also at the same time be used to recognize the proteins. It is also possible to use for recognition of the proteins conventional markers such as fluorescent dyes, enzyme markers which form a detectable reaction product after reaction with a substrate, or radioactive markers, alone or in combination with the anchors for derivatizing the proteins.

Production of Antibodies:

Anti-PARP2 antibodies are produced in a manner familiar to the skilled worker. Antibodies mean both polyclonal, monoclonal, human or humanized antibodies or fragments thereof, single chain antibodies or also synthetic antibodies, likewise antibody fragments such as Fv, Fab and F(ab$^1$)$_2$. Suitable production methods are described, for example, in Campbell, A. M., Monoclonal Antibody Technology, (1987) Elsevier Verlag, Amsterdam, New York, Oxford and in Breitling, F. and Dübel, S., Rekombinante Antikörper (1997), Spektrum Akademischer Verlag, Heidelberg.

Further Use of the Coding Sequence:

The present cDNA additionally provides the basis for cloning the genomic sequence of the novel PARP genes. This also includes the relevant regulatory or promoter sequence, which is available, for example, by sequencing the region located 5' upstream of the cDNA according to the invention or located in the introns of the genes. The cDNA sequence information is also the basis for producing antisense molecules or ribozymes with the aid of known methods (cf. Jones, J. T. and Sallenger, B. A. (1997) Nat. Biotechnol. 15, 902; Nellen, W. and Lichtenstein, C. (1993) TIBS, 18, 419). The genomic DNA can likewise be used to produce the gene constructs described above.

Another possibility of using the nucleotide sequence or parts thereof is to generate transgenic animals. Transgenic overexpression or genetic knock-out of the sequence information in suitable animal models may provide further valuable information about the (patho)physiology of the novel genes.

Therapeutic Applications:

In situations where there is a prevailing deficiency of a protein according to the invention it is possible to employ several methods for replacement. On the one hand, the protein, natural or recombinant, can be administered directly or by gene therapy in the form of its coding nucleic acid (DNA or RNA). It is possible to use any suitable vectors for this, for example both viral and non-viral vehicles. Suitable methods are described, for example, by Strauss and Barranger in Concepts in Gene Therapy (1997), Walter de Gruyter, publisher. Another alternative is provided by stimulation of the endogenous gene by suitable agents.

It is also possible to block the turnover or the inactivation of PARPs according to the invention, for example by proteases. Finally, inhibitors or agonists of PARPs according to the invention can be employed.

In situations where a PARP is present in excess or is overactivated, various types of inhibitors can be employed. This inhibition can be achieved both by antisense molecules, ribozymes, oligonucleotides or antibodies, and by low molecular weight compounds.

The active substances according to the invention, i.e., PARP proteins, nucleic acids and PARP binding partners such as, for example, antibodies or modulators, can be administered either as single therapeutic active substances or as mixtures with other therapeutic active substances. They can be administered as such, but in general they are administered in the form of pharmaceutical compositions, i.e., as mixtures of the active substance(s) with at least one suitable pharmaceutical carrier or diluent. The active substances or compositions can be administered in any way suitable for the particular therapeutic purpose, e.g., orally or parenterally.

The nature of the pharmaceutical composition and of the pharmaceutical carrier or diluent depends on the required mode of administration. Oral compositions can be, for example, in the form of tablets or capsules and may contain customary excipients such as binders (e.g., sirup, acacia, gelatin, sorbitol, tragacanth or polyvinylpyrrolidone), bulking agents (e.g., lactose, sugar, corn starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid products may be in the form of aqueous or oily suspensions, solutions, emulsions, sirups, elixirs or sprays etc. or may be in the form of dry powders for reconstitution with water or another suitable carrier. Liquid products of these types may contain conventional additives, for example suspending agents, flavorings, diluents or emulsifiers. It is possible to employ for parenteral administration solutions or suspensions with conventional pharmaceutical carriers. Parenteral administration of active substances according to the invention advantageously takes place using a liquid pharmaceutical composition which can be administered parenterally, in particular intravenously. This preferably contains an effective amount of at least one active substance, preferably in dissolved form, in a pharmaceutically acceptable carrier suitable for this purpose. Examples of pharmaceutical carriers suitable for this purpose are, in particular, aqueous solutions such as, for example, physiological saline, phosphate-buffered saline, Ringer's solution, Ringer's lactate solution and the like. The composition may moreover contain further additions such as antioxidants, chelating agents or antimicrobial agents.

The choice in each case of the dosage of the active substances according to the invention and the particular dosage schedule are subject to a decision of the treating physician. The latter will select a suitable dose and an appropriate dosage schedule depending on the chosen route of administration, on the efficacy of the medicine in each case, on the nature and severity of the disorder to be treated, and on the condition of the patient and his response to the therapy. Thus, for example, the pharmacologically active substances can be administered to a mammal (human or animal) in doses of about 0.5 mg to about 100 mg per kg of body weight and day. They can be administered in a single dose or in several doses.

Nontherapeutic Applications:

The nucleic acids according to the invention, such as, for example, cDNA, the genomic DNA, the promoter, and the polypeptide, and partial fragments thereof, can also be used in recombinant or nonrecombinant form for developing various test systems.

For example, it is possible to establish a test system which is suitable for measuring the activity of the promoter or of the protein in the presence of a test substance. The methods of measurement in this case are preferably simple ones, e.g., colorimetric, luminometric, fluorimetric, immunological or radioactive, and allow preferably a large number of test substances to be measured rapidly. Tests of this type are suitable and advantageous for so-called high-throughput screening. These test systems allow test substances to be assessed for their binding to or their agonism, antagonism or inhibition of proteins according to the invention.

Determination of the amount, activity and distribution of the proteins according to the invention or their underlying mRNA in the human body can be used for the diagnosis, for the determination of the predisposition and for the monitoring of certain diseases. Likewise, the sequence of the cDNA and the genomic sequence may provide information about genetic causes of and predispositions to certain diseases. It is possible to use for this purpose both DNA/RNA probes and antibodies of a wide variety of types. The nucleotide sequences according to the invention or parts thereof can further be used in the form of suitable probes for detecting point mutations, deletions or insertions.

The proteins according to the invention can further be used to identify and isolate their natural ligands or interacting partners. The proteins according to the invention can additionally be used to identify and isolate artificial or synthetic ligands. For this purpose, the recombinantly prepared or purified natural protein can be derivatized in such a way that it has modifications which permit linkage to support materials. Proteins bound in this way can be incubated with various analytes, such as, for example, protein extracts or peptide libraries or other sources of ligands. Specifically bound peptides, proteins or low molecular weight, non-proteinogenous substances can be isolated and characterized in this way. Non-proteinogenous substances mean, for example, low molecular weight chemical substances which may originate, for example, from classical drug synthesis or from so-called substance libraries which have been synthesized combinatorially.

The protein extracts used are derived, for example, from homogenates of plants or parts of plants, microorganisms, human or animal tissues or organs.

Ligands or interacting partners can also be identified by methods like the yeast two-hybrid system (Fields, S, and Song, O. (1989) Nature, 340, 245). The expression banks which can be employed in this case may be derived, for example, from human tissues such as, for example, brain, heart, kidney etc.

The nucleic acid sequences according to the invention and the proteins encoded by them can be employed for developing reagents, agonists and antagonists or inhibitors for the diagnosis and therapy of chronic and acute diseases associated with the expression or activation of one of the protein sequences according to the invention, such as, for example, with increased or decreased expression thereof. The reagents, agonists, antagonists or inhibitors developed can subsequently be used to produce pharmaceutical preparations for the treatment or diagnosis of disorders. Examples of possible diseases in this connection are those of the brain, of the peripheral nervous system, of the cardiovascular system or of the eye, of septic shock, of rheumatoid arthritis, diabetes, acute kidney failure, or of cancer.

The relevance of the proteins according to the invention for said indications was verified using specific inhibitors in relevant animal models.

The invention is now illustrated in detail with reference to the following examples.

Example 1

Isolation of the PARP2 and PARP3 cDNA

The present cDNA sequences were found for the first time on sequence analysis of cDNA clones of a cDNA library from human brain (Human Brain 5'Stretch Plus cDNA Library, # HL3002a, Clontech). The mouse PARP3 clones were isolated from a "lambda triplex mouse brain cDNA library" (Clontech order No. ML5004t). The sequences of these clones are described in SEQ ID NO:1, 3, 7 and 9.

Example 2

Expression of PARP2 and PARP3 in Human Tissues

The expression of human PARP2 and human PARP3 was investigated in twelve different human tissues by Northern blot analysis. A Human Multiple Tissue Northern Blot (MTN∩) supplied by Clontech (#7760-1 and #7780-1) was hybridized for this purpose with an RNA probe. The probe was produced by in vitro transcription of the corresponding cDNA of human PARP2 and human PARP3 in the presence of digoxigenin-labeled nucleotides in accordance with the manufacturer's method (BOEHRINGER MANNHEIM DIG Easy Hyb order No. 1603 558, DIG Easy Hyb method for RNA:RNA hybridization). The protocol was modified to carry out the prehybridization: 2×1 h with addition of herring sperm DNA (10 mg/ml of hybridization solution). Hybridization then took place overnight with addition of herring sperm DNA (10 mg/ml of hybridization solution). The bands were detected using the CDP-Star protocol (BOEHRINGER MANNHEIM CDP-Star™ order No. 1685 627).

After stringent washing, the transcript of PARP2 was mainly detected in human brain, heart, skeletal muscle, kidney and liver. The transcript size of about 1.9 kb corresponds to the length of the cDNA determined (1.85 kb) (cf. FIG. 2(A)).

In other tissues or organs, human PARP2 expression is considerably weaker.

After stringent washing, the transcript of PARP3 was mainly detected in heart, brain, kidney, skeletal muscle and liver. Expression in other tissues (placenta, lung, pancreas) is distinctly weaker (cf. FIG. 2(B)). There are at least 2 transcripts for human PARP3, which can presumably be explained by different polyadenylation sites or alternative splicing. Their size (about 2.2 kb and 2.5 kb respectively) corresponds to the length of the cDNA determined (2.3 kb). Washing was carried out with 0.2×SSC/0.2% SDS at room temperature for 2×15 minutes and then with 0.1×SSC/0.1% SDS at 65° C. for 2×15 minutes (prepared from 20×SSC: 3M NaCl, 0.3M sodium citrate, pH 7.0).

Example 3

Production of Antibodies

Specific antibodies against the proteins according to the invention were produced. These were used inter alia for analyzing the tissue distribution at the protein level of PARP2 and PARP3 by immunoblot (Western blot) analysis. Examples of the production of such antibodies are indicated below.

The following peptides were prepared by synthesis in the manner familiar to the skilled worker for the antibody production. In some cases, a cysteine residue was attached to the N or C terminals of the sequences in order to facilitate coupling to KLH (keyhole limpet hemocyanin).

```
PARP-2:
        (amino acids 1-20; SEQ ID NO: 23)
NH2-MAARRRRSTGGGRARALNES-CO2H (amino acids 335-353; SEQ ID NO: 24)
NH2-KTELQSPEHPLDQHYRNLHC-CO2H PARP-3:
        (amino acids 25-44 SEQ ID NO: 25)
NH2-CKGRQAGREEDPFRSTAEALK-CO2H (amino acids 230-248; SEQ ID NO: 26)
NH2-CKQQIARGFEALEALEEALK-CO2H
```

The production of an anti-PARP3 antibody is described as a representative example.

For human PARP3, polyclonal antibodies were raised in rabbits using a synthetic peptide having the peptide sequence H$_2$N-KQQIARGFEALEALEEALK-CO$_2$H (SEQ ID NO: 27) (amino acids 230-248 of the human PARP3 protein sequence). The corresponding mouse sequence differs in this region only by one amino acid (H$_2$N-KQQIARGFEALEALEEAMKCO$_2$H; SEQ ID NO: 28). A cysteine was also attached to the N terminus in order to make it possible for the protein to couple to KLH.

Rabbits were immunized a total of five times, at intervals of 7-14 days, with the KLH-peptide conjugate. The antiserum obtained was affinity-purified using the antigen. The specific IgG fraction was isolated from the serum using the respective peptides which, for this purpose, were initially immobilized on an affinity column in the manner familiar to the skilled worker. The respective antiserum was loaded onto this affinity column, and nonspecifically sorbed proteins were eluted with buffer. The specifically bound IgG fraction was eluted with 0.2 M glycine/HCl buffer pH 2.2. The pH was immediately increased using a 1M TRIS/HCl buffer pH 7.5. The eluate containing the IgG fraction was mixed 1:1 (volume) with saturated ammonium sulfate solution and incubated at +4° C. for 30 min to complete the precipitation. The resulting precipitate was centrifuged at 10,000 g and, after removal of the supernatant, dissolved in the minimum amount of PBS/TBS. The resulting solution was then dialyzed against PBS/TBS in the ratio 1:100 (volume). The antibodies were adjusted to a concentration of about 100 μg of IgG/ml. The PARP3 antibodies purified in this way had high specificity for PARP3. Whereas mouse PARP3 was recognized well, there was no observable cross-reaction with PARP1 or PARP2.

Example 4

Analysis of the Tissue Distribution by Immunoblot

Western Blot

The tissue distribution at the protein level was also investigated for PARP2 and PARP3 by immunoblot (Western blot) analysis.

Preparation of the Mouse Tissues for Protein Gels:

Tissues or cells were homogenized using a Potter or Ultra-Turrax. For this, 0.5 g of tissue (or cells) was incubated in 5 ml of buffer (10 mM Tris-HCl pH 7.5, 1 mM EDTA, 6 mM $MgCl_2$), one tablet of protease inhibitor cocktail (Boehringer Mannheim, order No.: 1836153) and benzonase (purity grade I, MERCK) at 37° C. for 30 min. Tissue samples from mice were produced for heart, lung, liver, spleen, kidney, intestine, muscle, brain and for human embryonic kidney cells (HEK293, human embryonal kidney).

Protein Gels:

The NuPAGE system supplied by NOVEX was used according to the instructions for protein gels. Polyacrylamide gels (NuPAGE 4-12% BisTris, NOVEX NP 0321), running buffer (MES-Running Buffer, NOVEX NP 0002), antioxidant (NOVEX NP 0005), protein size standard (Multi Mark Multi Colored Standard, NOVEX LC 5725), sample buffer (NuPAGE LDS Sample Buffer (4×), NOVEX NP 0007) were used. The gels were run for 45 minutes at a voltage of 200 V.

Western Blot:

Western blots were carried out using the NOVEX system in accordance with instructions. A nitrocellulose membrane (Nitrocellulose Pore size 45 µm, NOVEX LC 2001) was used. The transfer took 1 hour at a current of 200 mA. The transfer buffer consisted of 50 ml of transfer buffer concentrate (NOVEX NP 0006), 1 ml of antioxidant (NOVEX NP 0002), 100 ml of analytical grade methanol and 849 ml of double-distilled water.

Besides the blots produced in this way, also used were premade blots, for example from Chemicon (mouse brain blot, Chemicon, catalog No.: NS 106 with the tissues 1. frontal cortex, 2. posterior cortex, 3. cerebellum, 4. hippocampus, 5. olfactory bulb, 6. striatum, 7. thalamus, 8. mid brain, 9. entorhinal cortex, 10. pons, 11. medulla, 12. spinal cord).

Antibody Reaction with PARP3:

The Western blots were blocked in TEST (TBS+0.3% Tween 20) with 55, dry milk powder for at least 2 hours (TBS: 100 mM Tris pH 7.5, 200 mM NaCl). The antibody reaction with the primary antibody (dilution 1:1000) took place in TBST with 5% dry milk powder (see above) at room temperature for at least 2 hours or at 4° C. overnight, with gentle agitation (vertical rotator). This was followed by washing three times in TBST for 5 minutes. Incubation with the secondary antibody (anti-rabbit IgG, peroxidase-coupled, SIGMA A-6154, dilution 1:2000) took place in TBST with 5% dry milk powder for 1 hour. This was followed by washing three times for 5 minutes each time as above. The subsequent detection was based on chemiluminescence using the SUPER BLAZE kit (Pierce, Signal BLAZE Chemiluminescent Substrate 34095) as stated by the manufacturer. The "Lumi-Film" (Chemiluminescent Detection Film, Boehringer order No: 1666916) was used. The films were developed for about 2 min (X-ray developer concentrate, ADEFO-Chemie GmbH), hydrated, fixed for about 4 min (Acidofix B5 g/l/AGFA), hydrated and then dried.

Example 5

Preparation of the Enzymes

For comparison, human PARP1 was expressed recombinantly in the baculovirus system in the manner familiar to the skilled worker and partially purified as described (Shah et al., Analytical Biochemistry 1995, 227, 1-13). Bovine PARP1 in a purity of 30-50%; (c=0.22 mg/ml, spec. activity 170 nmol of ADP-ribose/min/mg of total protein at 25° C.) was purchased from BIOMOL (order No. SE-165). Human and mouse PARP2 and PARP3 were expressed recombinantly in the baculovirus system (Bac-to-Bac system, BRL LifeScience). For this purpose, the appropriate cDNAs were cloned to the pFASTBAC-1 vector. Preparation of recombinant baculovirus DNA by recombination in *E. coli* was followed by transfection of insect cells (Sf9 or High-Five) with the appropriate recombinant baculovirus DNAs. Expression of the corresponding proteins was verified by Western blot analysis. Virus strains were amplified in the manner familiar to the skilled worker. Larger amounts of recombinant proteins were obtained by infecting 500 ml of insect cell culture ($2\times10^6$ cells/ml) with viruses in an MOI (multiplicity of infection; ratio of viruses to cells) of 5-10 and incubating for 3 to 4 days. The insect cells were then pelleted by centrifugation, and the proteins were purified from the pellet.

The purification took place by classical methods of protein purification familiar to the skilled worker, detecting the enzymes with appropriate specific antibodies. In some cases, the proteins were also affinity-purified on a 3-aminobenzamide affinity column as described (Burtscher et al., Anal Biochem 1986, 152:285-290). The purity was >90%.

Example 6

Assay Systems for Determining the Activity of PARP2 and PARP3 and the Inhibitory Action of Effectors on PARP1, PARP2 and PARP3 a) Production of Antibodies Against Poly(ADP-Ribose)

It is possible to use poly(ADP-ribose) as antigen for generating anti-poly(ADP-ribose) antibodies. The production of anti-poly(ADP-ribose) antibodies is described in the literature (Kanai Y et al. (1974) Biochem Biophys Res Comm 59:1, 300-306; Kawamaitsu H et al. (1984) Biochemistry 23, 3771-3777; Kanai Y et al. (1978) Immunology 34, 501-508).

The following were used, inter alia: anti-poly(ADP-ribose) antibodies (polyclonal antiserum, rabbits), BIOMOL; order No. SA-276, anti-poly(ADP-ribose) antibodies (monoclonal, mouse; clone 10H; hybridoma supernatant, affinity-purified).

The antisera or monoclonal antibodies obtained from hybridoma supernatant were purified by protein A affinity chromatography in the manner familiar to the skilled worker.

b) ELISA

Materials:

ELISA color reagent: TMB mix, SIGMA T-8540

A 96-well microtiter plate (FALCON Micro-Test III™ Flexible Assay Plate, #3912) was coated with histones (SIGMA, H-7755). Histones were for this purpose dissolved in carbonate buffer (0.05M $Na_2HCO_3$; pH 9.4) in a concentration of 50 µg/ml. The individual wells of the microtiter plate were each incubated with 150 µl of this histone solution at room temperature for at least 2 hours or at 4° C. overnight. The wells are then blocked by adding 150 µl of a 1% BSA solution (SIGMA, A-7888) in carbonate buffer at room temperature for 2 hours. This is followed by three washing steps with washing buffer (0.05% Tween10 in 1×PBS; PBS (Phosphate buffered saline; Gibco, order No. 10010): 0.21 g/l $KH_2PO_4$, 9 g/l NaCl, 0.726 g/l $Na_2HPO_4$ $7H_2O$, pH 7.4). Washing steps were all carried out in a microtiter plate washer ("Columbus" microtiter plate washer, SLT-Labinstruments, Austria).

Required for the enzyme reaction were an enzyme reaction solution and a substrate solution, in each case as a premix. The absolute amount of these solutions depended on the intended number of assay wells.

Composition of the Enzyme Reaction Solution Per Well:

4 µl of PARP reaction buffer (1M Tris-HCl pH 8.0, 100 mM $MgCl_2$, 10 mM DTT)

20 ng of PARP1 (human or bovine) or 8 ng PARP2 (human or mouse)
4 μl of activated DNA (1 mg/ml; SIGMA, D-4522)
H$_2$O ad 40 μl Composition of the Substrate Solution Per Well:
5 μl of PARP reaction buffer (10×)
0.8 μl of NAD solution (10 mM, SIGMA N-1511)
44 μl H$_2$O Inhibitors were dissolved in ix PARP reaction buffer. DMSO, which was occasionally used to dissolve inhibitors in higher concentrations, was no problem up to a final concentration of 2%. For the enzyme reaction, 40 μl of the enzyme reaction solution were introduced into each well and incubated with 10 μl of inhibitor solution for 10 minutes. The enzyme reaction was then started by adding 50 μl of substrate solution per well. The reaction was carried out at room temperature for 30 minutes and then stopped by washing three times with washing buffer.

The primary antibodies employed were specific anti-poly (ADP-ribose) antibodies in a dilution of 1:5000. Dilution took place in antibody buffer (1% BSA in PBS; 0.05% Tween20). The incubation time for the primary antibodies was one hour at room temperature. After subsequently washing three times with washing buffer, incubation was carried out with the secondary antibody (anti-mouse IgG, Fab fragments, peroxidase-coupled, Boehringer Mannheim, order No. 1500.686; anti-rabbit IgG, peroxidase-coupled, SIGMA, order No. A-6154) in a dilution of 1:10,000 in antibody buffer at room temperature for one hour. Washing three times with washing buffer was followed by the color reaction using 100 μl of color reagent (TMB mix, SIGMA) per well at room temperature for about 15 min. The color reaction was stopped by adding 100 μl of 2M H$_2$SO$_4$. This was followed by immediate measurement in an ELISA plate reader (EAR340AT "Easy Reader", SLT-Labinstruments, Austria) (450 nm versus 620 nm). The measurement principle is depicted diagrammatically in FIG. 6.

Various concentrations were used to construct a dose-effect plot to determine the $K_i$ value of an inhibitor. Values are obtained in triplicate for a particular inhibitor concentration. Arithmetic means are determined using Microsoft© Excel. The IC50 is determined using the Microcal© Origin Software (Vers. 5.0) ("Sigmoidal Fit"). Conversion of the IC$_{50}$ value is calculated in this way into $K_i$ values took place by using "calibration inhibitors".

The "calibration inhibitors" were also measured in each analysis. The $K_i$ values of the "calibration inhibitors" were determined in the same assay system by analysis of the Dixon diagram in the manner familiar to the skilled worker.

b) HTRF (Homogenous Time-Resolved Fluorescence) Assay

In the HTRF PARP assay according to the invention, histones, as target proteins for modification by PARP, are labeled indirectly with an XL665 fluorophore. The anti poly(ADP ribose) antibody is directly labeled with a europium cryptate (anti-PAR-cryptate). If the XL665 fluorophore is in the direct vicinity in space, which is ensured by binding to the poly (ADP-ribose) on the histone, then energy transfer is possible. The emission at 665 nm is thus directly proportional to the amount of bound antibody, which in turn is equivalent to the amount of poly(ADP-ribose). The measured signal thus corresponds to the PARP activity. The measurement principle is depicted diagrammatically in FIG. 7. The materials used are identical to those used in the ELISA (see above) unless expressly indicated.

Histones were dissolved in a concentration of 3 mg/ml in Hepes buffer (50 mM, pH=7.5). Biotinylation took place with sulfo-NHS-LC-biotin (Pierce, #21335T). A molar ratio of 4 biotin molecules per histone was used. The incubation time was 90 minutes (RT). The biotinylated histones were then purified on a G25 SF HR10/10 column (Pharmacia, 17-0591-01) in Hepes buffer (50 mM, pH=7.0) in order to remove excess biotinylation reagent. The anti-poly(ADP-ribose) antibody was labeled with europium cryptate using bifunctional coupling reagents (Lopez, E. et al., Clin. Chem. 39(2), 196-201 (1993); U.S. Pat. No. 5,534,622).

Purification took place on a G25SF HR10/30 column. A molar ratio of 3.1 cryptates per antibody was achieved. The yield was 256. The conjugates were stored at −80° C. in the presence of 0.196 BSA in phosphate buffer (0.1M, pH=7).

For the enzyme reaction, the following were pipetted into each well:
10 μl of PARP solution in PARP HTRF reaction buffer (50 mM TrisHCl pH 8.0, 10 mM MgC$_2$, 1 mM DTT) with 20 ng of PARP1 (human or bovine) or 8 ng of PARP2 (human or mouse)
10 μl of activated DNA in PARP HTRF reaction buffer (50 μg/ml)
10 μl of biotinylated histones in PARP HTRF reaction buffer (1.25 μM)
10 μl of inhibitor in PARP HTRF reaction buffer These reagents were incubated for 2 minutes before the reaction was started by adding
10 μl of NAD solution in PARP HTRF reaction buffer (41 μM/ml). The reaction time was 30 minutes at room temperature.

The reaction was then stopped by adding
10 μl of PARP inhibitor (25 μM, $K_i$=10 nM) in "Revelation" buffer (100 mM Tris-HCl pH 7.2, 0.2M KF, 0.05% BSA).

The following were then added:
10 μl of EDTA solution (SIGMA, E-7889, 0.5M in H$_2$O)
100 μl of Sa-XL665 (Packard Instruments) in "Revelation" buffer (15-31.25 nM)
50 μl of anti-PAR cryptate in "Revelation" buffer (1.6-3.3 nM).

Measurement was then possible after 30 minutes (up to 4 hours). The measurement took place in a "discovery HTRF microplate analyzer" (Canberra Packard Instruments). The $K_i$ values were calculated as described for the ELISA.

Example 7

Test Systems for Determining the Therapeutic Efficacy of PARP Inhibitors

Novel PARP inhibitors can have their therapeutic efficacy checked in relevant pharmacological models. Examples of some suitable models are listed in Table 1.

| Disorder | Model | Literature |
| --- | --- | --- |
| Neurodegenerative disorders (stroke, Parkinson's, etc.) | NMDA excitotoxicity in mice or rats | See below for description |

-continued

| Disorder | Model | Literature |
| --- | --- | --- |
| Stroke | Permanent MCAO ("middle cerebral arterial occlusion") | Tokime, T. et al., J. Cereb. Blood Flow Metab., 18(9): 991-7, 1998. Guegan, C., Brain Research. Molecular Brain Research, 55(1): 133-40, 1998. |
| | Transient, focal MCAO in rats or mice | Eliasson M J L et al., Nat Med 1997, 3: 1089-1095. Endres, M et al., J Cereb Blood Flow Metab 1997, 17: 1143-1151. Takahashi K et al., J Cereb Blood Flow Metab 1997, 17: 1137-1142. |
| Parkinson's disease | MPTP (1-methyl-4-phenyl-1,2,3,6-tetrahydropyridine) toxicity in mice/rats | Cosi C, et al., Brain Res., 1998 809(1): 58-67. Cosi C, et al., Brain Res., 1996 729(2): 264-9. |
| Myocardial infarct | Coronary vessel occlusion in rats, pigs or rabbits | Richard V, et al., Br. J. Pharmacal 1994, 113, 869-876. Thiemermann C, et al., Proc Natl Acad Sci USA. 1997, 94(2): 679-83. Zingarelli B, et al., Cardiovasc Res. 1997, 36(2): 205-15. |
| | Langendorf heart model in rats or rabbits | See below for description |
| Septic shock | Endotoxin shock in rats | Szabo C, et al., J Clin Invest, 1997, 100(3): 723-35. |
| | Zymosan- or carrageenan-induced multiple organ failure in rats or mice | Szabo C, et al. J Exp Med. 1997, 186(7): 1041-9. Cuzzocrea S, et al. Eur J Pharmacol. 1998, 342(1): 67-76. |
| Rheumatoid arthritis | Adjuvant- or collagen-induced arthritis in rats or mice | Szabo C, et al., Proc Natl Acad Sci USA. 1998, 95(7): 3867-72. |
| Diabetes | Streptozotocin- and alloxan-induced or obesity-associated | Uchgata Y et al., Diabetes 1983, 32: 316-318. Masiello P et al., Diabetologia 1985, 28: 683-686. Shimabukuro M et al., J Clin Invest 1997, 100: 290-295. |
| Cancer | In vitro model; see below | Schlicker et al., 1999, 75(1), 91-100. | a) NMDA Excitotoxicity Model

Glutamate is the most important excitory neurotransmitter in the brain. Under normal conditions, glutamate is secreted into the synaptic cleft and stimulates the post-synaptic glutamate receptors, specifically the glutamate receptors of the "NMDA" and "AMPA" types. This stimulation plays a significant part in numerous functions of the brain, including learning, memory and motor control.

Under the conditions of acute and chronic neurodegeneration (e.g., stroke), however, there is a great increase in the presynaptic glutamate secretion, resulting in excessive stimulation of the receptors. This leads to death of the cells stimulated in this way. These increased glutamate activities occur in a number of neurological disorders or psychological disturbances and lead to states of overexcitation or toxic effects in the central nervous system (CNS) but also in the peripheral nervous system. Thus, glutamate is involved in a large number of neurodegenerative disorders, in particular neurotoxic disturbances following hypoxia, anoxia, ischemia and after lesions like those occurring after stroke and trauma, and stroke, Alzheimer's disease, Huntington's disease, amyotrophic lateral sclerosis (ALS; "Lou Gehring's disease"), cranial trauma, spinal cord trauma, peripheral neuropathies, AIDS dementia and Parkinson's disease. Another disease in which glutamate receptors are important is epilepsy (cf. Brain Res Bull 1998; 46(4):281-309, Eur Neuropsychopharmacol 1998, 8(2):141-52.).

Glutamate effects are mediated through various receptors. One of these receptors is called the NMDA (N-methyl-D-aspartate) receptor after a specific agonist (Arzneim. Forschung 1990, 40, 511-514; TIPS, 1990, 11, 334-338; Drugs of the Future 1989, 14, 1059-1071). N-Methyl-D-aspartate is a strong agonist of a particular class of glutamate receptors ("NMDA" type). Stimulation of the NMDA receptor leads to influx of calcium into the cell and the generation of free radicals. The free radicals lead to DNA damage and activation of PARP. PARP in turn causes cell death through depletion of high-energy phosphates (NAD and ATP) in the cell. This explains the toxicity of NMDA. Treatment of animals with NMDA can therefore be regarded as a model of the above-mentioned disorders in which excitotoxicity is involved.

Because of the importance of glutamate receptors in neurodegeneration, many pharmacological approaches to date have been directed at specific blocking of precisely these receptors. However, because of their importance in normal stimulus conduction, these approaches have proved to be problematic (side effects). In addition, stimulation of the receptors is an event which takes place very rapidly so that administration of the receptors often comes too late ("time window" problem). Thus there is a great need for novel principles of action and inhibitors of NMDA-related neurotoxicity.

Protection against cerebral overexcitation by excitatory amino acids (NMDA antagonism in mice) can be regarded as adequate proof of the activity of a pharmacological effector of PARP in disorders based on excitotoxicity. Intracerebral administration of excitatory amino acids (EAA) induces such massive overexcitation that it leads within a short time to convulsions and death of the animals (mice).

In the present case there was unilateral intracerebroventricular administration of 10 µl of a 0.035% strength aqueous NMDA solution 120 minutes after intraperitoneal (i.p.) administration of the test substance. These symptoms can be inhibited by systemic, e.g., intraperitoneal, administration of centrally acting drugs. Since excessive activation of EAA receptors in the central nervous system plays an important part in the pathogenesis of various neurological disorders, information can be gained from the detected EAA antagonism in vivo about possible therapeutic utilizability of the substances for such CNS disorders. An ED50 at which 50% of the animals are, due to preceding i.p. administration of the measured substance, free of symptoms with a fixed dose of NMDA was determined as a measure of the activity of the substances.

b) Langendorf Heart Model (Model for Myocardial Infarct)

Male Sprague-Dawley rats (bodyweight 300-400 g; origin Janvier, Le Genest-St-Isle, France) were used for the test. The rats were treated orally by gavage with the active substance or placebo (volume: 5 ml/kg). 50 minutes later, heparin is administered intraperitoneally (Liquemin N Roche, 125 IU/animal in 0.5 ml). The animals are anesthetized with Inactin® T133 (thiobetabarbital sodium 10%), fixed on the operating table, tracheotomized and ventilated with a "Harvard ventilatory pump" (40 beats/min, 4.5 ml/beat). Thoracotomy was followed by immediate catheterization of the aorta, removal of the heart and immediate retrograde perfusion. The hearts were perfused with a constant pressure of 75 mmHg, which is achieved using a "Gilson Miniplus 2 perfusion pump". Composition of the perfusate (mmol/l): NaCl 118, KCl 4.7, $CaCl_2 \times 2 H_2O$ 2.52, $MgSO_4 \times 7 H_2O$ 1.64, $NaHCO_3$ 24.88, $KH_2PO_4$ 1.18, glucose 11. The temperature is kept at 37° C. throughout the experiment. Functional parameters were continuously recorded using a "Gould 4-channel recorder". Measurements were made of the left-ventricular pressure (LVP; mmHg), LVEDP (mmHg), enzyme release (creatine kinase, mU/ml/g), coronary flow rate (ml/min), HR (pulse rate, $min^{-1}$). The left-ventricular pressure was measured using a liquid-filled latex balloon and a Statham23 Db pressure transducer. The volume of the balloon was initially adjusted to reach an LVEDP (left-ventricular end-diastolic pressure) of about 12 mmHg. The $dP/dt_{max}$ (maximum pumping force) is derived from the pressure signal using a differentiator module. The heart rate was calculated from the pressure signal. The flow rate was determined using a drop counter (BMT Messtechnik GmbH Berlin). After an equilibration time of 20 minutes, the hearts were subjected to a 30-minute global ischemia by stopping the perfusate supply while keeping the temperature at 37° C. During the following 60-minute reperfusion period, samples of the perfusate were taken after 3, 5, 10, 15, 30, 45 and 60 min for analysis of creatine kinase (CK) activity. Means and standard deviations for the measured parameters were analyzed statistically (Dunnett test). The significance limit was p=0.05.

The experiment on rabbit hearts was carried out similarly. Male white New Zealand rabbits (obtained from: Interfauna) were used. The hearts were prepared as described above for the rat model. The perfusion pressure was set at a maximum of 60 mmHg and the flow rate at about 25 ml/min. The equilibration time was about 30 min. The substance was administered by infusion directly upstream of the heart. 15 min after starting the infusion, a 30-minute global ischemia was caused by stopping the flow while maintaining the temperature of the heart. A 30-minute reperfusion followed. Perfusate was taken for investigation of CK activity before administration of the substance, after 15 min and at various times (5, 10, 15, 20, 30 min) during the reperfusion. The following parameters were measured: LVP (mmHg), LVEDP, LVdP/dt, PP (mmHg), HR (pulse rate; beats/min), CK activity (U/min/g heart weight).

c) Animal Model for Acute Kidney Failure

The protective effect of intravenous administration of PARP inhibitors (4 days) on the kidney function of rats with postischemic acute kidney failure was investigated.

Male Sprague-Dawley rats (about 330 g at the start of the experiments; breeder: Charles River) were used. 10-15 animals were employed per experimental group. Administration of active substance/placebo took place continuously with an osmotic micropump into the femoral vein. Orbital blood was taken (1.5 ml of whole blood) under inhalation anesthesia with enflurane (Ethrane Abbot, Wiesbaden).

After the initial measurements (blood sample) and determination of the amount of urine excreted in 24 h, the rats were anesthetized ("Nembutal", pentobarbital sodium, Sanofi CEVA; 50 mg/kg i.p., volume injected 1.0 ml/kg) and fastened on a heatable operating table (37° C.). 125 IU/kg heparin (Liquemin N, Roche) were administered i.v. into the caudal vein. The abdominal cavity was opened and the right kidney was exposed. The branching-off renal artery was exposed and clamped off superiorly using bulldog clamps (Diefenbach 38 mm). The left renal artery was likewise exposed and clamped off (superiorly, about half way to the kidney). During the operation, an osmotic micropump was implanted into the femoral vein. The intestine was reinserted and the fluid loss was compensated with luke-warm 0.9% NaCl. The animals were covered with a moist cloth and kept warm under red light. After 40 min, the appearance of the kidneys was recorded, and the clamps were removed, first the right then the left. The intestine was put back and 2 drops of antibiotic (Tardomyocel, Bayer) were added. The abdominal wall was closed with sterile cat gut (Ethicon No. 4) and treated once more with 1 drop of antibiotic. The epidermis was sutured with sterile Ethibond Exel (Ethicon) No. 3/0, and the suture was sprayed with Nebacetin N (Yamanouchi) wound spray. A tenth of a daily dose of drug/placebo is given as i.v. bolus.

Samples and blood were taken for investigating biochemical parameters in the serum and urine: Na, K, creatinine, protein (only in urine), on days 1, 2 and 4 of the experiment. In addition, the feed and water consumption, bodyweight and urine volume were recorded. After 14 days, the animals were sacrificed and the kidneys were assessed.

The assessment excluded all animals which died of an infarct during the experiment or showed an infarct at necropsy on day 14. The creatinine clearance and the fractional sodium excretion were calculated as kidney function parameters, comparing treated animals with control and sham.

d) In Vitro Model for Radiosensitization (Tumor Therapy)

MCF-7-cells (human breast carcinoma) were cultivated in Dulbecco's modified Eagle's medium with 10% heat-inactivated FCS and 2 mM L-glutamine. Cells were seeded out overnight in cell densities of 100, 1000 or 10,000 cells per well in a 6-well plate and then exposed to ionizing radiation with a dose in the range from 0 to 10 Gy ($^{137}$Cs, Shepard Mark, model I-6BA, dose rate 3.28 Gy/min). 10 days after the irradiation, the experiment was assessed, counting colonies with fifty cells as positive.

e) Stroke Model (Focal Cerebral Ischemia; MCA (Middle Cerebral Artery) Occlusion on a Rat)

A focal ischemia was performed by means of cauterisation of the right distal MCA on Sprague-Dawley or Long-Evans rats. The rats may be treated before or after the beginning of the MCA occlusion with modulators of the proteins of the invention. As a rule, doses of 1-10 mg/kg are chosen (bolus application), optionally followed by a continuous infusion of 0.5-5 mg/kg/h.

The rats are anesthetised with halothane in a mixture of 70% nitrogen and 30% oxygen (4% at initial phase and 0.8-1.2% during the operation). The body temperature was permanently measured rectally and was kept constant at 37.5° C.±0.5° C. by means of a controllable heating blanket. Moreover, arterial blood pressure, arterial pH, ($Pa(O_2)$ and $Pa(CO_2)$ were optionally measured by means of a tail vein catheder. Thereafter, the focal iscehmia was carried out using the method of Chen et al. (Stroke 17: 738-743; 1986) or Liu et al. (Am. J. Physiol. 256: H589-593; 1989) by means of continuous cauterisation of the distal part of the right MCA. When the operation was terminated, the animals were kept in a warm environment for a further 24 hours. Then they were killed with the use of $CO_2$ and decapitated. Their brains were taken, shock-frozen (dry ice or liquid nitrogen) and stored at −80° C. The brains were cut into 0.02 mm thick slices and every 20th cut was used for the subsequent analysis. The corresponding cuts are stained with cresyl violet (Nissl staining). Alternatively, TTC (2,3,4-triphenyltetrazoliumchloride) may be used for staining. The infarct volume may then be analysed under a microscope. For exact quantification, a computer-based image analyzing software may be used (J. Cereb. Clood Flow Metabol. 10:290-293; 1990).

f) Septic Shock

Groups of 10 male C57/BL mice (body weight 18-20 g) are treated with LPS (lipopolysaccharide, from *E. coli*, $LD_{100}$ 20 mg/animal i.v.) plus galactosamine (20 mg/animal i.v.). The substance to be tested is applied i.p. or i.v. during three succeeding days (e.g., 1-10 mg/kg), with the first dose being administered 30 minutes after the LPS treatment. The death rate is determined every 12 hours. Alternatively, the substance may also be applied in several doses spread over the days.

g) Determination of Altered Gene Expression in Aging Cells

The aging of cells is simulated by changing the cell culture media from the complete medium with a reduced serum concentration and thereafter is analysed by means of quantitative PCR or Northern Blotting (Linskens et al., Nucleic Acids Res. 1995, 23(16):3244-51). As typical markers for the aging of the skin for example collagen or elastin may be used. Human fibroblasts or fibroblast cell lines are used which simulate the aging of the skin. Modulators of the proteins of the invention are added to the medium and their effect on the changing of the gene expression is observed. An increased production of elastin in cells with a reduced aging process caused by means of said modulators may be observed.

We claim:

1. An isolated and purified nucleic acid consisting of a nucleotide sequence selected from the group consisting of nucleotides +3 to +1715 of SEQ ID NO:1, nucleotides +242 to +1843 of SEQ ID NO:3, nucleotides +221 to +1843 of SEQ ID NO:5, nucleotides +112 to +1710 of SEQ ID NO:7, and nucleotides +1 to +1584 of SEQ ID NO:9,
wherein the nucleic acid codes for a poly(ADP-ribose) polymerase (PARP) that has poly(ADP-ribose)-synthesizing activity and no zinc finger motifs.

2. An expression cassette comprising, under the genetic control of at least one regulatory nucleotide sequence, at least one nucleic acid comprising a nucleotide sequence selected from the group consisting of nucleotides +3 to +1715 of SEQ ID NO:1, nucleotides +242 to +1843 of SEQ ID NO:3, nucleotides +221 to +1843 of SEQ ID NO:5, nucleotides +112 to +1710 of SEQ ID NO:7, and nucleotides +1 to +1584 of SEQ ID NO:9,
wherein the nucleic acid codes for a poly(ADP-ribose) polymerase (PARP) that has poly(ADP-ribose)-synthesizing activity and no zinc finger motifs.

3. A recombinant vector comprising at least one expression cassette as claimed in claim 2.

4. A recombinant microorganism comprising at least one recombinant vector as claimed in claim 3.

* * * * *